United States Patent
Saenko et al.

(10) Patent No.: US 7,211,559 B2
(45) Date of Patent: May 1, 2007

(54) FACTOR VIII COMPOSITIONS AND METHODS

(75) Inventors: Evgueni L. Saenko, Gaithersburg, MD (US); Andrey G. Sarafanov, Rockville, MD (US); Natalya M. Ananyeva, Derwood, MD (US)

(73) Assignee: University of Maryland, Baltimore, Baltimore, MD (US)

( * ) Notice: Subject to any disclaimer, the term of this patent is extended or adjusted under 35 U.S.C. 154(b) by 0 days.

(21) Appl. No.: 10/968,286

(22) Filed: Oct. 20, 2004

(65) Prior Publication Data

US 2005/0100990 A1    May 12, 2005

Related U.S. Application Data

(60) Provisional application No. 60/515,638, filed on Oct. 31, 2003.

(51) Int. Cl.
A61K 35/14 (2006.01)
A61K 38/00 (2006.01)

(52) U.S. Cl. .................. 514/2; 530/380; 530/383

(58) Field of Classification Search ............ None
See application file for complete search history.

(56) References Cited

U.S. PATENT DOCUMENTS

| | | |
|---|---|---|
| 4,757,006 A | 7/1988 | Toole, Jr. et al. |
| 4,868,112 A | 9/1989 | Toole, Jr. |
| 4,965,199 A | 10/1990 | Capon et al. |
| 5,004,803 A | 4/1991 | Kaufman et al. |
| 5,364,771 A | 11/1994 | Lollar et al. |
| 5,583,209 A | 12/1996 | Lollar et al. |
| 5,650,391 A | 7/1997 | Schwartz et al. |
| 5,663,060 A | 9/1997 | Lollar et al. |
| 5,681,746 A | 10/1997 | Bodner et al. |
| 5,744,446 A | 4/1998 | Lollar et al. |
| 5,859,204 A | 1/1999 | Lollar |
| 5,888,974 A | 3/1999 | Lollar et al. |
| 6,083,905 A | 7/2000 | Voorberg et al. |
| 6,180,371 B1 | 1/2001 | Lollar |
| 6,376,463 B1 | 4/2002 | Lollar |
| 6,458,563 B1 | 10/2002 | Lollar |
| 2003/0068785 A1 | 4/2003 | Lollar |
| 2003/0166536 A1 | 9/2003 | Lollar |
| 2004/0248785 A1 | 12/2004 | Saenko et al. |

FOREIGN PATENT DOCUMENTS

| | | |
|---|---|---|
| CA | 2205824 | 5/1997 |
| EP | 0 808 901 A2 | 11/1997 |
| WO | WO 87/04187 | 7/1987 |
| WO | WO 88/03558 | 5/1988 |
| WO | WO 88/08035 | 10/1988 |
| WO | WO 93/20093 | 10/1993 |
| WO | WO 94/11503 | 5/1994 |
| WO | WO 95/18827 | 7/1995 |
| WO | WO 97/03195 | 1/1997 |
| WO | WO 97/49725 | 12/1997 |
| WO | WO 00/27425 | 5/2000 |
| WO | WO 00/28021 | 5/2000 |
| WO | WO 00/71714 A2 | 11/2000 |
| WO | WO 02/060951 A2 | 8/2002 |

OTHER PUBLICATIONS

Church, W.R., et al., "Coagulation factors V and VIII and ceruloplasmin constitute a family of structurally related proteins," *Proc. Natl. Acad. Sci. USA 81*:6934-6937, National Academy of Sciences (1984).

Fass, D.N., et al., "Monoclonal Antibodies to Porcine Factor VIII Coagulant and Their Use in the Isolation of Active Coagulant Protein," *Blood 59*:594-600, Grune & Stratton (1982).

Gitschier, J., et al., "Characterization of the human factor VIII gene," *Nature 312*:326-330, Macmillan Publishers (1984).

Herz, J., et al., "Surface location and high affinity for calcium of a 500-kd liver membrane protein closely related to the LDL-receptor suggest a physiological role as lipoprotein receptor," *EMBO J. 7*:4119-4127, IRL Press Ltd. (1988).

Ho, G., et al., "Receptor-mediated Endocytosis of Coagulation Factor Xa Requires Cell Surface-bound Tissue Factor Pathway Inhibitor," *J. Biol. Chem. 271*:9497-9502, The American Society for Biochemistry and Molecular Biology, Inc. (1996).

Knauer, M.F., et al., "Identification of a Binding Site in Protease Nexin I (PN1) Required for the Receptor Mediated Internalization of PN1-Thrombin Complexes," *J. Biol. Chem. 272*:12261-12264, The American Society for Biochemistry and Molecular Biology, Inc. (1997).

Kounnas, M.Z., et al., "Cellular Internalization and Degradation of Antithrombin III-Thrombin, Heparin Cofactor II-Thrombin, and $\alpha_1$-Antitrypsin-Trypsin Complexes Is Mediated by the Low Density Lipoprotein Receptor-related Protein," *J. Biol. Chem. 271*:6523-6529, The American Society for Biochemistry and Molecular Biology (1996).

Mikhailenko, I., et al., "Cellular Internalization and Degradation of Thrombospondin-1 Is Mediated by the Amino-terminal Heparin Binding Domain (HBD)," *J. Biol. Chem. 272*:6784-6791, The American Society for Biochemistry and Molecular Biology, (1997).

Moestrup, S.K., et al., "Distribution of the $\alpha_2$-macroglobulin receptor/low density lipoprotein receptor-related protein in human tissues," *Cell Tissue Res. 269*:375-382, Springer-Verlag (1992).

Moestrup, S.K., et al., "$\alpha_2$-Macroglobulin-Proteinase Complexes, Plasminogen Activator Inhibitor Type-1-Plasminogen Activator Complexes, and Receptor-associated Protein Bind to a Region of the ÿ2-Macroglobulin Receptor Containing a Cluster of Eight Complement-type Repeats," *J. Biol. Chem. 268*:13691-13696, The American Society for Biochemistry and Molecular Biology (1993).

(Continued)

Primary Examiner—Nashaat T. Nashed
Assistant Examiner—Holly Schnizer
(74) Attorney, Agent, or Firm—Sughrue Mion, PLLC

(57) ABSTRACT

The present invention provides methods of increasing the half-life and/or specific activity of factor VIII. More specifically, the invention provides methods of increasing the half-life and/or specific activity of factor VIII by substituting one or more amino acids in the A2 domain. It further provides methods for producing such factor VIII mutants. The invention also provides polynucleotides encoding the mutant factor VIII, and methods of treating hemophilia using the polypeptides and polynucleotides of the invention.

12 Claims, 29 Drawing Sheets

OTHER PUBLICATIONS

Moestrup, S.K., "The $\alpha_2$-macroglobulin receptor and epithelial glycoprotein-330: two giant receptors mediating endocytosis of multiple ligands," *Biochim. et Biophys. Acta.* 1197:197-213, Elsevier Science B.V. (1994).

Narita, M., et al., "The Low-Density Lipoprotein Receptor-Related Protein (LRP) Mediates Clearance of Coagulation Factor Xa In Vivo," *Blood* 91:555-560, W.B. Saunders Company (1998).

Nykjaer, A., et al., "Purified $\alpha_2$-Macroglobulin Receptor/LDL Receptor-related Protein Binds Urokinase Plasminogen Activator Inhibitor Type-1 Complex," *J. Biol. Chem.* 267:14543-14546, The American Society for Biochemistry and Molecular Biology (1992).

Orth, K., et al., "Complexes of tissue-type plasminogen activator and its serpin inhibitor plasminogen-activator inhibitor type 1 are internalized by means of the low density lipoprotein receptor-related protein/$\alpha_2$-macroglobulin receptor," *Proc. Natl. Acad. Sci. USA* 89:7422-7426, National Academy of Sciences (1992).

Saenko, E.L., et al., "Role of the Low Density Lipoprotein-related Protein Receptor in Mediation of Factor VIII Catabolism," *J. Biol. Chem.* 274:37685-37692, The American Society for Biochemistry and Molecular Biology (1999).

Strickland, D.K., et al., "Sequence Identity between the $\alpha_2$-Macroglobulin Receptor and Low Density Lipoprotein Receptor-related Protein Suggests That This Molecule Is a Multifunctional Receptor," *J. Biol. Chem.* 265: 17401-17404, The American Society for Biochemistry and Molecular Biology (1990).

Strickland, D.K., et al., "LDL receptor-related protein: a multiligand receptor for lipoprotein and preteinase catabolism," *FASEB J.* 9:890-898, Federation of American Societies for Experimental Biology (1995).

Toole, J.J., et al., "Molecular cloning of a cDNA encoding human antihaemophilic factor," *Nature* 312:342-347, Macmillan Publishers (1984).

Toole, J.J., et al., "A large region (≈95 kDa) of human factor VIII is dispensable for in vitro procoagulant activity," *Proc. Natl. Acad. Sci. USA* 83:5939-5942, National Academy of Sciences (1986).

Vehar, G.A., et al., "Structure of human factor VIII," *Nature* 312:337-342, Macmillan Publishers (1984).

Warshawsky, I., et al., "The low density lipoprotein receptor-related protein mediates the cellular degradation of tissue factor pathway inhibitor," *Proc. Natl. Acad. Sci. USA* 91:6664-6668, National Academy of Sciences (1994).

Williams, S.E., et al., "A Novel Mechanism for Controlling the Activity of $\alpha_2$-Macroglobulin Receptor/Low Density Lipoprotein Receptor-related Protein," *J. Biol. Chem.* 267:9035-9040, The American Society for Biochemistry and Molecular Biology (1992).

Wood, W.I., et al., "Expression of active human factor VIII from recombinant DNA clones," *Nature* 312:330-337, Macmillan Publishers (1984).

Yakhyaev, A., et al., "Cellular uptake and degradation of the thrombin activated factor VIII fragments," *Blood* 90:31a, Abstract No. 126, W.B. Saunders Company (1997).

Dialog File 351, Accession No. 11425054, Derwent WPI English language abstract for EP 0 808 901 A2 (Document AM2).

Dialog File 351, Accession No. 13204439, Derwent WPI English language abstract for WO 00/27425 (Document AN2).

Dialog File 351, Accession No. 13204665, Derwent WPI English language abstract for WO 00/28021 (Document AO2).

NCBI Entrez, GenBank Report, Accession No. M63959, from Striekland, D.K., et al., (1993).

NCBI Entrez, GenBank Report, Accession No. X01179, from Wood, W.I., et al., (1993).

NCBI Entrez, GenBank Report, Accession No. CAA25619, from Wood, W.I., et al., (1993).

Ananyeva, N.M, et al., "Catabolism of the Coagulation Factor VIII. Can We Prolong Lifetime of fVIII in Circulation?" *Trends Cardio. Med.* 11:251-257, Elsevier Science Inc (2001).

Barenholz, Y., et al., "A Simple Method for the Preparation of Homogenous Phospholipid Vesicles," *Biochem.* 16:2806-2810, American Chemical Society (1977).

Barrow, R.T., et al., "Inhibition by Heparin of the Human Blood Coagulation Intrinsic Pathway Factor X Activator," *J. Biol. Chem.* 269:26796-26800, The American Society for Biochemistry and Molecular Biology, Inc. (1994).

Barrow, R.T., et al., "Inhibition by Heparin of Thrombin-catalyzed Activation of the Factor VIII-von Willebrand Factor Complex," *J. Biol. Chem.* 269:593-598, The American Society for Biochemistry and Molecular Biology, Inc. (1994).

Baruch, D., et al., "Binding of Heparin Fractions to von Willebrand Factor: Effect of Molecular Weight and Affinity for Antithrombin III," *Thromb. Haemost.* 71:141-146, F.K. Schattauer Verlagsgesellschaft mbH (1994).

Bovenschen, N., et al., "Elevated plasma factor VIII in a mouse model of low-density lipoprotein receptor-related protein deficiency," *Blood* 101:3933-3939, The American Society of Hematology (May 2003).

Bützow, R., et al., "A 60-kD Protein Mediates the Binding of Transforming Growth Factor-$\beta$ to Cell Surface and Extracellular Matrix Proteoglycans," *J. Cell. Biol.* 122:721-727, The Rockefeller University Press (1993).

Celie, P.H.N., et al., "Substitution of Arg$^{527}$ and Arg$^{531}$ in factor VIII associated with mild haemophilia A: characterization in terms of subunit interaction and cofactor function," *Br. J. Haematol* 106:792-800, Blackwell Science Ltd. (1999).

Chappell, D.A., et al., "The Low Density Lipoprotein Receptor-related Protein/$\alpha_2$-Macroglobulin Receptor Binds and Mediates Catabolism of Bovine Milk Lipoprotein Lipase," *J. Biol. Chem.* 267:25764-25767, The American Society for Biochemistry and Molecular Biology, Inc. (1992).

Chen, W.-J., et al., "NPXY, a Sequence Often Found in Cytoplasmic Tails, Is Required for Coated Pit-mediated Internalization of the Low Density Lipoprotein Receptor," *J. Biol. Chem.* 265:3116-3123, The American Society for Biochemistry and Molecular Biology, Inc. (1990).

Crisp, R.J., et al., "Roles of the Heparin and Low Density Lipid Receptor-related Protein-binding Sites of Protease Nexin 1 (PN1) in Urokinase-PN1 Complex Catabolism," *J. Biol. Chem.* 275:19628-19637, The American Society for Biochemistry and Molecular Biology, Inc. (2000).

Dazzi, F., et al., "High incidence of anti-FVIII antibodies against non-coagulant epitopes in haemophilia A patients: a possible role for the half-life of transfused FVIII," *Br. J. Haematol.* 93:688-693, Blackwell Science Ltd. (1996).

Fay, P.J., and Scandella, D., "Human Inhibitor Antibodies Specific for the Factor VIII A2 Domain Disrupt the Interaction between the Subunit and Factor IXa," *J. Biol. Chem.* 274:29826-29830, The American Society for Biochemistry and Molecular Biology, Inc. (1999).

Fay, P.J., et al., "Factor VIIIa A2 Subunit Residues 558-565 Represent a Factor IXa Interactive Site," *J. Biol. Chem.* 269:20522-20527, The American Society for Biochemistry and Molecular Biology, Inc. (1994).

Fay, P.J., and Koshibu, K., "The A2 Subunit of Factor VIIIa Modulates the Active Site of Factor IXa," *J. Biol. Chem.* 273:19049-19054, The American Society for Biochemistry and Molecular Biology, Inc. (1998).

Gilbert, G.E., et al., "Four Hydrophobic Amino Acids of the Factor VIII C2 Domain Are Constituents of Both the Membrane-binding and von Willebrand Factor-binding Motifs," *J. Biol. Chem.* 277:6374-6381, The American Society for Biochemistry and Molecular Biology, Inc. (Feb. 2002).

Herz, J., et al., "LDL Receptor-Related Protein Internalizes and Degrades uPA-PAI-1 Complexes and Is Essential for Embryo Implantation," *Cell* 71:411-421, Cell Press (1992).

Ji, Z.-S., et al., "Secretion-Capture Role for Apolipoprotein E in Remnant Lipoprotein Metabolism Involving Cell Surface Heparan Sulfate Proteoglycans," *J. Biol. Chem.* 269:2764-2772, The American Society for Biochemistry and Molecular Biology, Inc. (1994).

Kamikubo, Y.-I., et al., "The Clearance of Proteoglycan-Associated Human Recombinant Tissue, Factor Pathway Inhibitor (H-RTFPI) in Rabbits: A Complex Formation of H-RTFPI with Factor Xa Promotes a Clearance Rate of H-RTFPI," *Thromb. Res.* 83:161-173, Elsevier Science Ltd. (1996).

Knauer, M.F., et al., "The Efficient Catabolism of Thrombin-Protease Nexin 1 Complexes Is a Synergistic Mechanism That Requires Both the LDL Receptor-related Protein and Cell Surface Heparins," *J. Biol. Chem.* 272:29039-29045, The American Society for Biochemistry and Molecular Biology, Inc. (1997).

Knauer, M.F., et al., "Analysis of a Structural Determinant in Thrombin-Protease Nexin 1 Complexes That Mediates Clearance by the Low Density Lipoprotein Receptor-related Protein," *J. Biol. Chem.* 274:275-281, The American Society for Biochemistry and Molecular Biology, Inc. (1999).

Lander, A.D., "Proteoglycans: Master Regulators of Molecular Encounter?" *Matrix Biol.* 17:465-472, Gustav Fischer Verlag (1998).

Lenting, P.J., et al., "The Light Chain Factor VIII Comprises a Binding Site for Low Density Lipoprotein Receptor-related Protein," *J. Biol. Chem.* 274:23734-23739, The American Society for Biochemistry and Molecular Biology, Inc. (1999).

Lenting, P.J., et al., "Cellular Uptake of Activated Factor IX But Not Factor IX Zymogen Involves LDL-Receptor Related Protein," *Blood* 94:455a(Abstract #2026), The American Society of Hematology (1999).

Lollar, P., et al., "Factor VIII and Factor VIIIa," *Methods Enzymol.* 222:128-143, Academic Press, Inc. (1993).

Mahley, R.W., and Ji, Z.-S., "Remnant lipoprotein metabolism: key pathways involving cell-surface heparan sulfate proteoglycans and apolipoprotein E," *J. Lipid. Res.* 40:1-16, Lipid Research, Inc. (1999).

Mann, D.M., et al., "Delineation of the Glycosaminoglycan-binding Site in the Human Inflammatory Response Protein Lactoferrin," *J. Biol. Chem.* 269:23661-23667, The American Society for Biochemistry and Molecular Biology, Inc. (1994).

Mordenti, J., et al., "Pharmacokinetics and Interspecies Scaling of Recombinant Human Factor VIII," *Toxicology and Applied Pharmacology* 136:75-78, Academic Press, Inc. (1996).

Pemberton, S., et al., "A Molecular Model for the Triplicated A Domains of Human Factor VIII Based on the Crystal Structure of Human Ceruloplasmin," *Blood* 89:2413-2421, The American Society of Hematology (1997).

Poletti, L.F., et al., "Structural Aspects of Heparin Responsible for Interactions With von Willebrand Factor," *Arterioscler. Thromb. Vasc. Biol.* 17:925-931, American Heart Association (1997).

Sarafanov, A.G., et al., "Cell Surface Heparan Sulfate Proteoglycans Participate in Factor VIII Catabolism Mediated by Low Density Lipoprotein Receptor-related Protein," *J. Biol. Chem.* 276:11970-11979, The American Society for Biochemistry and Molecular Biology, Inc. (2001).

Schwarz, H.P., et al., "Involvement of low-density lipoprotein receptor-related protein (LRP) in the clearance of factor VIII in von Willebrand factor-deficient mice," *Blood* 95:1703-1708, The American Society of Hematology (2000).

Stoilova-Mcphie, S., et al., "3-Dimensional structure of membrane-bound coagulation factor VIII: modeling of the factor VIII heterodimer within a 3-dimensional density map derived by electron crystallography," *Blood* 99:1215-1223, The American Society of Hematology (Feb. 2002).

Warshawsky, I., et al., "The Low Density Lipoprotein Receptor-related Protein Can Function Independently from Heparan Sulfate Proteoglycans in Tissue Factor Pathway Inhibitor Endocytosis," *J. Biol. Chem.* 271:25873-25879, The American Society for Biochemistry and Molecular Biology, Inc. (1996).

EMBL Database Accession No. AAW11422, Cohen, F.E., et al., "Factor VIII: C analogue, delta 1311-1320," from WO 97/03195 (Nov. 20, 1998).

EMBL Database Accession No. AAW44137, Lollar, J., "New modified factor VIII molecules having reduced immunogenicity," from WO 97/49725 (Jun. 17, 1998).

Ananyeva, N., et al., "Treating haemophilia A with recombinant blood factors: a comparison," *Expert Opin. Pharmacother.* 5:1061-1070, Ashley Publications Ltd (May 2004).

Bovenschen, N., et al., "Cleavage of factor VIII heavy chain by thrombin increases the affinity for low-density lipoprotein receptor-related protein (LRP)," *J. Thromb. Haemost.* 1(Suppl. 1): 1 page, Blackwell Publishing, available online at www.blackwellpublishing.com/isth2003/abstract.asp?ls=7808 (Jul. 2003).

Cha, H.J., et al., "Simplification of Titer Determination for Recombinant Baculovirus by Green Fluorescent Protein Marker," *Bio Tech.* 23:782-786, Eaton Publishing Co. (1997).

Cunningham, M.A., et al., "LMAN1 is a molecular chaperone for the secretion of coagulation factor VIII," *J. Thromb. Haemost.* 1: 2360-2367, Blackwell Publishing (Nov. 2003).

Fay, P.J., et al., "Human Factor $VIII_a$ Subunit Structure," *J. Biol. Chem.* 266:8957-8962, The American Society for Biochemistry and Molecular Biology, Inc. (1991).

Garzia, L., et al., "Method to express and purify nm23-H2 protein from baculovirus-infected cells," *Bio Tech.* 35: 384-391, Eaton Publishing Co. (Aug. 2003).

Grosse, F. and Manns, A., "Chapter 10. Fast Isolation of Recombinant Baculovirus by Antibody Screening," in: *Methods in Molecular Biology. Baculovirus Expression Protocols*, Richardson, C.D., ed., Humana Press, Totowa, NJ, pp. 179-185 (1995).

Katagiri, Y. and Ingham, K.C., "Enhanced Production of Green Fluorescent Fusion Proteins in a Baculovirus Expression System by Addition of Secretion Signal," *Bio Tech.* 33:24-26, Eaton Publishing Co. (2002).

Koszelak, M.E., et al., "Sites in the A2 Subunit Involved in the Interfactor VIIIa Interaction," *J. Biol. Chem.* 275:27137-27144, The American Society for Biochemistry and Molecular Biology, Inc. (2000).

Lapan, K.A. and Fay, P.J., "Localization of a Factor X Interactive Site in the A1 Subunit of Factor VIIIa," *J. Biol. Chem.* 272:2082-2088, The American Society for Biochemistry and Molecular Biology, Inc. (1997).

Liebman, J.M., et al., "When Less is More: Enhanced Baculovirus Production of Recombinant Proteins at Very Low Multiplicities of Infection," *BioTech.* 26:36-42, Eaton Publishing Co. (1999).

Lollar, P. and Parker, E.T., "Structural Basis for the Decreased Procoagulant Activity of Human Factor VIII Compared to the Porcine Homolog," *J. Biol. Chem.* 266:12481-12486, The American Society for Biochemistry and Molecular Biology, Inc. (1991).

Lollar, P., et al., "Coagulant Properties of Hybrid Human/Porcine Factor VIII Molecules," *J. Biol. Chem.* 267:23652-23657, The American Society for Biochemistry and Molecular Biology, Inc., (1992).

Moussalli, M., et al., "Mannose-dependent Endoplasmic Reticulum (ER)-Golgi Intermediate Compartment-53-mediated ER to Golgi Trafficking of Coagulation Factors V and VIII," *J. Biol. Chem.* 274:32539-32542, The American Society for Biochemistry and Molecular Biology, Inc. (1999).

Payment, P., et al., eds., "Chapter 3. Isolation and Identification of Viruses," in: *Methods and Techniques in Virology*, Marcel Dekker, Inc., New York, NY, pp. 32-34 (1993).

Saenko, E.L. and Scandella, D., "A Mechanism for Inhibition of Factor VIII Binding to Phospholipid by von Willebrand Factor," *J. Biol. Chem.* 270:13826-13833, The American Society for Biochemistry and Molecular Biology, Inc. (1995).

Sarafanov, A.G., et al., "Identification of residues within the A2 domain of factor VIII critical for binding to low-density lipoprotein receptor-related protein," *Blood* 102:514a, American Society of Hematology (Nov. 2003).

Sarafanov, A. and Saenko, E., "High-throughput optimization of protein expression in the baculovirus system based on determination of relative expression efficiency of viral stocks," *Anal. Biochem.* 328:98-100, Elsevier Inc. (May 2004).

Saenko, E.L., et al., "The future of recombinant coagulation factors," *J. Thromb. Haemost.* 1:922-930, Blackwell Publishing, Inc. (May 2003).

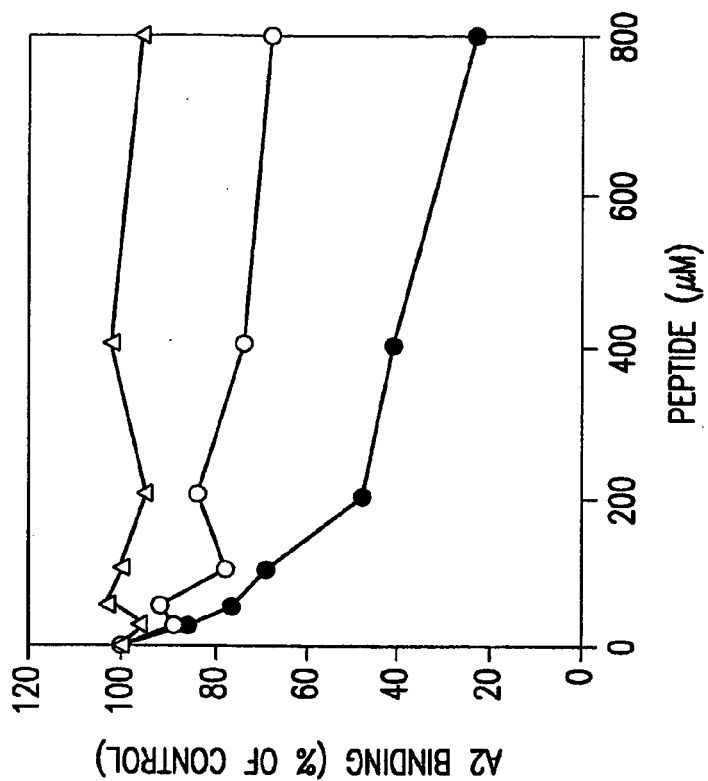
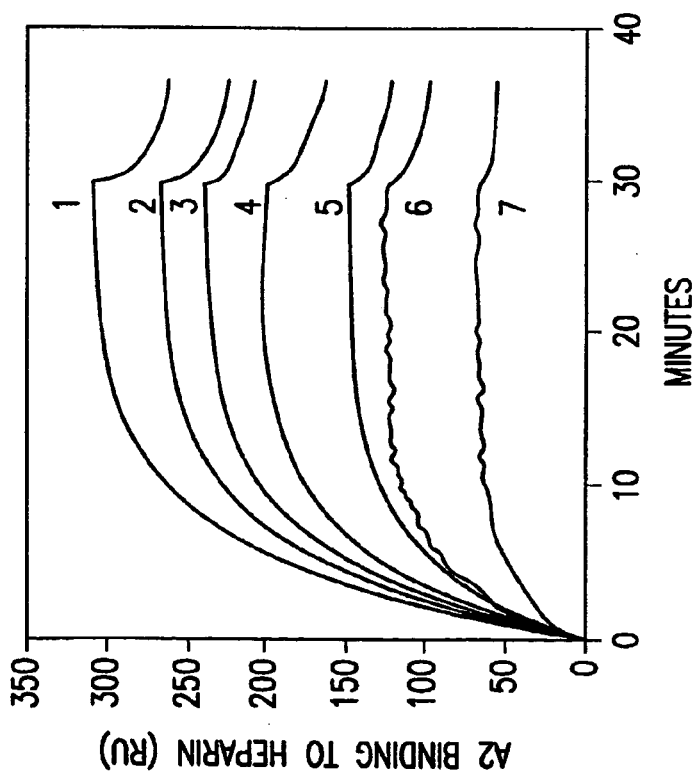
FIG.7B
FIG.7A

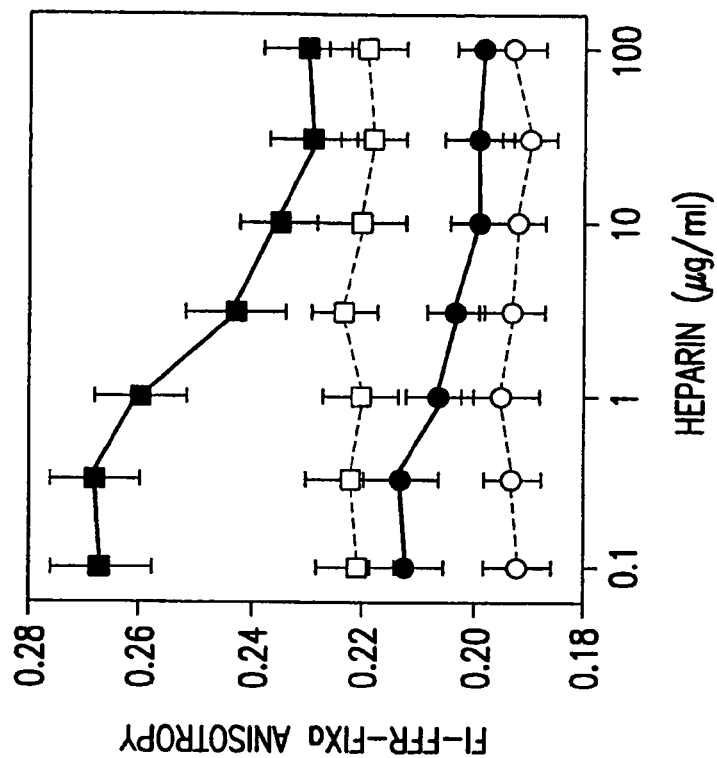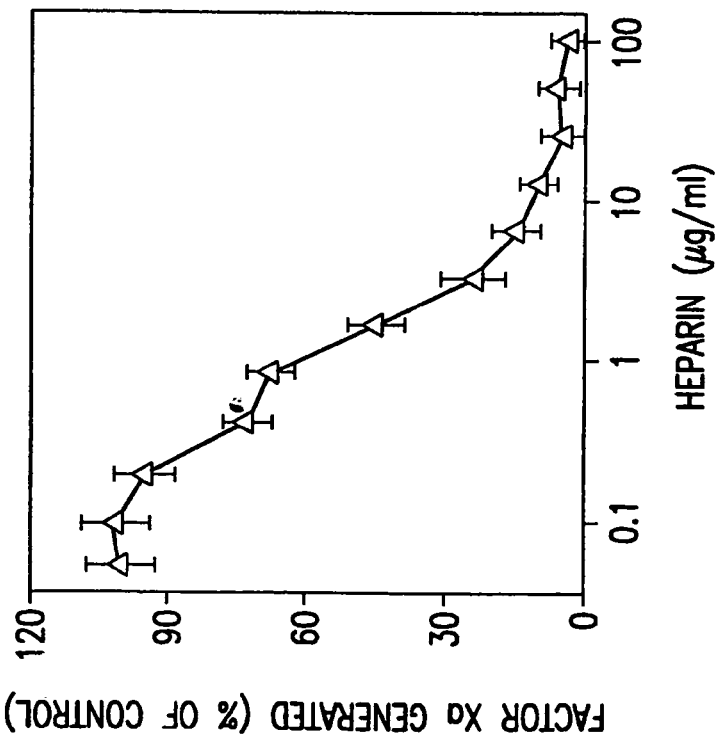
FIG.6B
FIG.6A

```
                                ATRRYYLGAVELSWDYMQSDLGELP
VDARFPPRVPKSFPFNTSVVYKKTLFVEFTDHLFNIAKPRPPWMGLLGPTIQAEVYDT
VVITLKNMASHPVSLHAVGVSYWKASEGAEYDDQTSQREKEDDKVFPGGSHTYVWQVL
KENGPMASDPLCLTYSYLSHVDLVKDLNSGLIGALLVCREGSLAKEKTQTLHKFILLF
AVFDEGKSWHSETKNSLMQDRDAASARAWPKMHTVNGYVNRSLPGLIGCHRKSVYWHV
IGMGTTPEVHSIFLEGHTFLVRNHRQASLEISPITFLTAQTLLMDLGQFLLFCHISSH
QHDGMEAYVKVDSCPEEPQLRMKNNEEAEDYDDDLTDSEMDVVRFDDDNSPSFIQIRS
VAKKHPKTWVHYIAAEEEDWDYAPLVLAPDDRSYKSQYLNNGPQRIGRKYKKVRFMAY
TDETFKTREAIQHESGILGPLLYGEVGDTLLIIFKNQASRPYNIYPHGITDVRPLYSR
        A2 Domain                                  ******
                                                      LRP
RLPKGVKHLKDFPILPGEIFKYKWTVTVEDGPTKSDPRCLTRYYSSFVNMERDLASGL
********************
Binding Region
IGPLLICYKESVDQRGNQIMSDKRNVILFSVFDENRSWYLTENIQRFLPNPAGVQLED
PEFQASNIMHSINGYVFDSLQLSVCLHEVAYWYILSIGAQTDFLSVFFSGYTFKHKMV
YEDTLTLFPFSGETVFMSMENPGLWILGCHNSDFRNRGMTALLKVSSCDKNTGDYYED
SYEDISAYLLSKNNAIEPREITRTTLQSDQEEIDYDDTISVEMKKEDFDIYDEDENQS
PRSFQKKTRHYFIAAVERLWDYGMSSSPHVLRNRAQSGSVPQFKKVVFQEFTDGSFTQ
PLYRGELNEHLGLLGPYIRAEVEDNIMVTFRNQASRPYSFYSSLISYEEDQRQGAEPR
KNFVKPNETKTYFWKVQHHMAPTKDEFDCKAWAYFSDVDLEKDVHSGLIGPLLVCHTN
TLNPAHGRQVTVQEFALFFTIFDETKSWYFTENMERNCRAPCNIQMEDPTFKENYRFH
```

FIG.12A

AINGYIMDTLPGLVMAQDQRIRWYLLSMGSNENIHSIHFSGHVFTVRKKEEYKMALYN

LYPGVFETVEMLPSKAGIWRVECLIGEHLHAGMSTLFLVYSNKCQTPLGMASGHIRDF

QITASGQYGQWAPKLARLHYSGSINAWSTKEPFSWIKVDLLAPMIIHGIKTQGARQKF

SSLYISQFIIMYSLDGKKWQTYRGNSTGTLMVFFGNVDSSGIKHNIFNPPIIARYIRL

HPTHYSIRSTLRMELMGCDLNSCSMPLGMESKAISDAQITASSYFTNMFATWSPSKAR

LHLQGRSNAWRPQVNNPKEWLQVDFQKTMKVTGVTTQGVKSLLTSMYVKEFLISSSQD

GHQWTLFFQNGKVKVFQGNQDSFTPVVNSLDPPLLTRYLRIHPQSWVHQIALRMEVLG

CEAQDLY

FIG. 12B

1 MQIELSTCFF LCLLRFCFSA TRRYYLGAVE LSWDYMQSDL GELPVDARFP PRVPKSFPFN

61 TSVVYKKTLF VEFTDHLFNI AKPRPPWMGL LGPTIQAEVY DTVVITLKNM ASHPVSLHAV

121 GVSYWKASEG AEYDDQTSQR EKEDDKVFPG GSHTYVWQVL KENGPMASDP LCLTYSYLSH

181 VDLVKDLNSG LIGALLVCRE GSLAKEKTQT LHKFILLFAV FDEGKSWHSE TKNSLMQDRD

241 AASARAWPKM HTVNGYVNRS LPGLIGCHRK SVYWHVIGMG TTPEVHSIFL EGHTFLVRNH

301 RQASLEISPI TFLTAQTLLM DLGQFLLFCH ISSHQHDGME AYVKVDSCPE EPQLRMKNNE

361 EAEDYDDDLT DSEMDVVRFD DDNSPSFIQI RSVAKKHPKT WVHYIAAEEE DWDYAPLVLA

421 PDDRSYKSQY LNNGPQRIGR KYKKVRFMAY TDETFKTREA IQHESGILGP LLYGEVGDTL

481 LIIFKNQASR PYNIYPHGIT DVRPLYSRRL PKGVKHLKDF PILPGEIFKY KWTVTVEDGP

541 TKSDPRCLTR YYSSFVNMER DLASGLIGPL LICYKESVDQ RGNQIMSDKR NVILFSVFDE

601 NRSWYLTENI QRFLPNPAGV QLEDPEFQAS NIMHSINGYV FDSLQLSVCL HEVAYWYILS

661 IGAQTDFLSV FFSGYTFKHK MVYEDTLTLF PFSGETVFMS MENPGLWILG CHNSDFRNRG

FIG. 13A

```
 721 MTALLKVSSC DKNTGDYYED SYEDISAYLL SKNNAIEPRS FSQNSRHRST RQKQFNATTI

781 PENDIEKTDP WFAHRTPMPK IQNVSSSDLL MLLRQSPTPH GLSLSDLQEA KYETFSDDPS

841 PGAIDSNNSL SEMTHFRPQL HHSGDMVFTP ESGLQLRLNE KLGTTAATEL KKLDFKVSST

901 SNNLISTIPS DNLAAGTDNT SSLGPPSMPV HYDSQLDTTL FGKKSSPLTE SGGPLSLSEE

961 NNDSKLLESG LMNSQESSWG KNVSSTESGR LFKGKRAHGP ALLTKDNALF KVSISLLKTN

1021 KTSNNSATNR KTHIDGPSLL IENSPSVWQN ILESDTEFKK VTPLIHDRML MDKNATALRL

1081 NHMSNKTTSS KNMEMVQQKK EGPIPPDAQN PDMSFFKMLF LPESARWIQR THGKNSLNSG

1141 QGPSPKQLVS LGPEKSVEGQ NFLSEKNKVV VGKGEFTKDV GLKEMVFPSS RNLFLTNLDN

1201 LHENNTHNQE KKIQEEIEKK ETLIQENVVL PQIHTVTGTK NFMKNLFLLS TRQNVEGSYD

1261 GAYAPVLQDF RSLNDSTNRT KKHTAHFSKK GEEENLEGLG NQTKQIVEKY ACTTRISPNT

1321 SQQNFVTQRS KRALKQFRLP LEETELEKRI IVDDTSTQWS KNMKHLTPST LTQIDYNEKE

1381 KGAITQSPLS DCLTRSHSIP QANRSPLPIA KVSSFPSIRP IYLTRVLFQD NSSHLPAASY

1441 RKKDSGVQES SHFLQGAKKN NLSLAILTLE MTGDQREVGS LGTSATNSVT YKKVENTVLP

1501 KPDLPKTSGK VELLPKVHIY QKDLFPTETS NGSPGHLDLV EGSLLQGTEG AIKWNEANRP

1561 GKVPFLRVAT ESSAKTPSKL LDPLAWDNHY GTQIPKEEWK SQEKSPEKTA FKKKDTILSL

1621 NACESNHAIA AINEGQNKPE IEVTWAKQGR TERLCSQNPP VLKRHQREIT RTTLQSDQEE

1681 IDYDDTISVE MKKEDFDIYD EDENQSPRSF QKKTRHYFIA AVERLWDYGM SSSPHVLRNR

1741 AQSGSVPQFK KVVFQEFTDG SFTQPLYRGE LNEHLGLLGP YIRAEVEDNI MVTFRNQASR

1801 PYSFYSSLIS YEEDQRQGAE PRKNFVKPNE TKTYFWKVQH HMAPTKDEFD CKAWAYFSDV

1861 DLEKDVHSGL IGPLLVCHTN TLNPAHGRQV TVQEFALFFT IFDETKSWYF TENMERNCRA

1921 PCNIQMEDPT FKENYRFHAI NGYIMDTLPG LVMAQDQRIR WYLLSMGSNE NIHSIHFSGH

1981 VFTVRKKEEY KMALYNLYPG VFETVEMLPS KAGIWRVECL IGEHLHAGMS TLFLVYSNKC
```

FIG. 13B

```
2041 QTPLGMASGH IRDFQITASG QYGQWAPKLA RLHYSGSINA WSTKEPFSWI KVDLLAPMII
2101 HGIKTQGARQ KFSSLYISQF IIMYSLDGKK WQTYRGNSTG TLMVFFGNVD SSGIKHNIFN
2161 PPIIARYIRL HPTHYSIRST LRMELMGCDL NSCSMPLGME SKAISDAQIT ASSYFTNMFA
2221 TWSPSKARLH LQGRSNAWRP QVNNPKEWLQ VDFQKTMKVT GVTTQGVKSL LTSMYVKEFL
2281 ISSSQDGHQW TLFFQNGKVK VFQGNQDSFT PVVNSLDPPL LTRYLRIHPQ SWVHQIALRM
2341 EVLGCEAQDL Y
```

FIG. 13C

```
  1 MAPRRVRSFL RGLPALLLLL LFLGPWPAAS HGGKYSREKN QPKPSPKRES GEEFRMEKLN
    ─────────────────────────────────
              Signal Sequence

61 QLWEKAQRLH LPPVRLAELH ADLKIQERDE LAWKKLKLDG LDEDGEKEAR LIRNLNVILA

121 KYGLDGKKDA RQVTSNSLSG TQEDGLDDPR LEKLWHKAKT SGKFSGEELD KLWREFLHHK

181 EKVHEYNVLL ETLSRTEEIH ENVISPSDLS DIKGSVLHSR HTELKEKLRS INQGLDRLRR
                                                                ****
241 VSHQGYSTEA EFEEPRVIDL WDLAQSANLT DKELEAFREE LKHFEAKIEK HNHYQKQLEI
    ********** ********** ********** ********** ********** **********
                              LDL Binding Region 301 AHEKLRHAES VGDGERVSRS REKHALLEGR TKELGYTVKK HLQDLSGRIS RARHNEL
    ******** ****** ****** ****** ****** *
```

FIG. 14

FACTOR VIII COMPOSITIONS AND METHODS

This application claims the benefit of U.S. Provisional Application No. 60/515,638, filed Oct. 31, 2003, which is incorporated by reference herein in its entirety.

STATEMENT REGARDING FEDERALLY-SPONSORED RESEARCH AND DEVELOPMENT

Part of the work performed during development of this invention utilized U.S. Government funds. The U.S. Government has certain rights in this invention.

BACKGROUND OF THE INVENTION

1. Field of the Invention

This invention relates generally to a mutant factor VIII having increased half-life and/or specific activity, methods of production, and pharmaceutically acceptable compositions and uses thereof.

2. Related Art

Coagulation of blood occurs by either the "intrinsic pathway" or the "extrinsic pathway," whereby certain blood proteins interact in a cascade of proteolytic activations to ultimately convert soluble fibrinogen to insoluble fibrin. These threads of fibrin are cross-linked to form the scaffolding of a clot; without fibrin formation, coagulation cannot occur.

The intrinsic pathway consists of seven steps: (1) the proteolytic activation of factor XII; (2) activated factor XII cleaves factor XI to activate it; (3) activated factor XI cleaves factor IX, thereby activating it; (4) activated factor IX interacts with activated factor VIII to cleave and activate factor X; (5) activated factor X binds to activated factor V on a membrane surface, which complex proteolytically cleaves prothrombin to form thrombin; (6) thrombin proteolytically cleaves fibrinogen to form fibrin; (7) fibrin monomers assemble into fibrils, which are then cross-linked by factor XIII.

The extrinsic pathway consists of the following steps: (1) upon rupture of a blood vessel, factor VII binds to tissue factor, a lipoprotein present in tissues outside the vascular system; (2) factor VII is activated to factor VIIa by proteolytic cleavage; and (3) the factor VIIa-tissue factor complex cleaves and activates factor X. Thereafter, the extrinsic pathway is identical to the intrinsic pathway, i.e. the two pathways share the last three steps described above.

The plasma glycoprotein factor VIII circulates as an inactive precursor in blood, bound tightly and non-covalently to von Willebrand factor. Factor VIII (fVIII) is proteolytically activated by thrombin or factor Xa, which dissociates it from von Willebrand factor (vWf) and activates its procoagulant function in the cascade. In its active form, factor VIIIa (fVIIIa) functions as a cofactor for the factor X activation enzyme complex in the intrinsic pathway of blood coagulation, and it is decreased or nonfunctional in patients with hemophilia A.

In hemophilia, blood coagulation is impaired by a deficiency in certain plasma blood coagulation factors. People with deficiencies in factor VIII or with antibodies against factor VIII suffer uncontrolled internal bleeding that may cause a range of serious symptoms unless they are treated with factor VIII. Symptoms range from inflammatory reactions in joints to early death. The classic definition of factor VIII, in fact, is that substance present in normal blood plasma that corrects the clotting defect in plasma derived from individuals with hemophilia A. A deficiency in vWf can also cause phenotypic hemophilia A because vWf is an essential component of functional factor VIII. In these cases, the half-life of factor VIII is decreased to such an extent that it can no longer perform its particular functions in blood-clotting.

The fVIII protein consists of a homologous A and C domains and a unique B domain which are arranged in the order A1-A2-B-A3-C1-C2 (Vehar, G. A., et al., *Nature* 312:337–340 (1984)). It is processed to a series of $Me^{2+}$ linked heterodimers produced by cleavage at the B-A3 junction (Fay, P. J., et al., *Biochem. Biophys. Acta.* 871: 268–278 (1986)), generating a light chain (LCh) consisting of an acidic region (AR) and A3, C1, and C2 domains and a heavy chain (HCh) which consists of the A1, A2, and B domains (FIG. 11).

Activation of fVIII by thrombin leads to dissociation of activated fVIII (fVIIIa) from vWf and at least a 100-fold increase of the cofactor activity. The fVIIIa is a A1/A2/A3-C1-C2 heterotrimer (Fay, P. J., et al., *J. Biol. Chem* 266: 8957–8962 (1991)) in which domains A1 and A3 retain the metal ion linkage (FIG. 11) and the stable dimer A1/A3-C1-C2 is weakly associated with the A2 subunit through electrostatic forces (Fay, P. J., et al., *J. Biol. Chem* 266: 8957–8962 (1991)). Spontaneous dissociation of the A2 subunit from the heterotrimer results in non-proteolytic inactivation of fVIIIa.

The A2 domain is necessary for the procoagulant activity of the factor VIII molecule. Studies show that porcine factor VIII has six-fold greater procoagulant activity than human factor VIII (Lollar, P., and E. T. Parker, *J. Biol. Chem.* 266:12481–12486 (1991)), and that the difference in coagulant activity between human and porcine factor VIII appears to be based on a difference in amino acid sequence between one or more residues in the human and porcine A2 domains (Lollar, P., et al., *J. Biol. Chem.* 267:23652–23657 (1992)).

Infusion of fVIII/vWf complex or purified plasma or recombinant fVIII into patients with severe hemophilia A who do not have fVIII (Fijnvandraat, K., et al., *Thromb. Haemostas.* 77:298–302 (1997); Morfini, M., et al., *Thromb. Haemostas.* 68:433–435 (1992)) or in normal individuals (Over, J., et al., *J. Clin. Invest.* 62:223–234 (1978)) results in a similar fVIII disappearance with a half-life of 12–14 hours. Although the complex between fVIII and vWf is crucial for normal half-life and level of factor VIII in the circulation, the mechanisms associated with turnover of fVIII/vWf complex are not well defined.

The human factor VIII gene was isolated and expressed in mammalian cells (Toole, J. J., et al., *Nature* 312:342–347 (1984); Gitschier, J., et al., *Nature* 312:326–330 (1984); Wood, W. I., et al., *Nature* 312:330–337 (1984); Vehar, G. A., et al., *Nature* 312:337–342 (1984); WO 87/04187; WO 88/08035; WO 88/03558; U.S. Pat. No. 4,757,006), and the amino acid sequence was deduced from cDNA. Capon et al., U.S. Pat. No. 4,965,199, disclose a recombinant DNA method for producing factor VIII in mammalian host cells and purification of human factor VIII. Human factor VII expression in CHO (Chinese hamster ovary) cells and BHKC (baby hamster kidney cells) has been reported. Human factor VIII has been modified to delete part or all of the B domain (U.S. Pat. No. 4,868,112), and replacement of the human factor VIII B domain with the human factor V B domain has been attempted (U.S. Pat. No. 5,004,803). The cDNA sequence encoding human factor VIII and predicted amino acid sequence are shown in SEQ ID NOs:1 and 2, respectively.

U.S. Pat. No. 5,859,204, Lollar, J. S., reports mutants of factor VIII having reduced antigenicity and reduced immunoreactivity. U.S. Pat. No. 6,376,463, Lollar, J. S., also reports mutants of factor VIII having reduced immunoreactivity.

Porcine factor VIII has been isolated and purified from plasma (Fass, D. N., et al., *Blood* 59:594 (1982)). Partial amino acid sequence of porcine factor VIII corresponding to portions of the N-terminal light chain sequence having homology to ceruloplasmin and coagulation factor V and largely incorrectly located were described by Church, et al., *Proc. Natl. Acad. Sci. USA* 81:6934 (1984). Toole, J. J., et al., *Nature* 312:342–347 (1984) described the partial sequencing of the N-terminal end of four amino acid fragments of porcine factor VIII but did not characterize the fragments as to their positions in the factor VIII molecule. The amino acid sequence of the B and part of the A2 domains of porcine factor VIII were reported by Toole, J. J., et al., *Proc. Natl. Acad. Sci. USA* 83:5939–5942 (1986). The cDNA sequence encoding the complete A2 domain of porcine factor VIII and predicted amino acid sequence and hybrid human/porcine factor VIII having substitutions of all domains, all subunits, and specific amino acid sequences were disclosed in U.S. Pat. No. 5,364,771 by Lollar and Runge, and in WO 93/20093. More recently, the nucleotide and corresponding amino acid sequences of the A1 and A2 domains of porcine factor VIII and a chimeric factor VIII with porcine A1 and/or A2 domains substituted for the corresponding human domains were reported in WO 94/11503. U.S. Pat. No. 5,859,204, Lollar, J. S., discloses the porcine cDNA and deduced amino acid sequences.

Cellular endocytosis mediated by LRP was shown to be a mechanism of removal of a number of structurally unrelated ligands including several proteins related to coagulation or fibrilolysis. These ligands are: complexes of thrombin with antithrombin III (ATIII), heparin cofactor II (HC11) (Kounnas, M. Z., et al., *J. Biol. Chem.* 271:6523–6529 (1996)), protease nexin I (Knauer, M. F., et al., *J. Biol. Chem.* 272:12261–12264 (1997)), complexes of urokinase-type and tissue-type plasminogen activators (u-PA and t-PA, respectively) with plasminogen activator inhibitor (PAI-1) (Nykjaer, A., et al., *J. Biol. Chem.* 267:14543–14546 (1992); Orth, K., et al., *Proc. Natl. Acad. Sci.* 89:7422–7426 (1992)), thrombospondin (Mikhailenko, I., et al., *J. Biol. Chem.* 272:6784–6791 (1997)), tissue factor pathway inhibitor (TFPI) (Warshawsky, I., et al., *Proc. Natl. Acad. Sci.* 91:6664–6668 (1994)), and factor Xa (Narita, M., et al., *Blood* 91:555–560 (1998); Ho, G., et al., *J. Biol. Chem* 271:9497–9502 (1996)).

LRP, a large cell-surface glycoprotein identical to $\alpha_2$-macroglobulin receptor (Strickland, D. K., et al., *J. Biol. Chem.* 265:17401–17404 (1990)), is a member of the low density lipoprotein (LDL) receptor family which also includes the LDL receptor, very low density lipoprotein (VLDL) receptor, vitellogenin receptor and glycoprotein 330 receptor. LRP receptor consists of the non-covalently linked 515 kDa α-chain (Herz, J., et al., *EMBO J.* 7:4119–4127 (1988)) containing binding sites for LRP ligands, and the 85 kDa transmembrane β-chain. Within the α-chain, cluster of cysteine-rich class A repeats is responsible for ligand binding (Moestrup, S. K., et al., *J. Biol. Chem* 268:13691–13696 (1993)). In contrast to the acidic ligand binding region in LRP, ligands of LRP expose regions rich in positively charged amino acid residues (Moestrup, S. K., *Biochim. Biophys. Acta* 1197:197–213 (1994)). This type of binding and 31 class A repeats present in LRP may be responsible for its wide ligand diversity and ability to serve as a multi-ligand clearance receptor. LRP is expressed in many cell types and tissues including placenta, lung and brain (Moestrup, S. K., et al., *Cell Tissue Res.* 269:375–382 (1992)) and is a major endocytic receptor in the liver (Strickland, D. K., et al., *FASEB J.* 9:890–898 (1995)).

A 39 kDa receptor-associated protein (RAP) binds to LRP with high affinity ($K_d$=4 nM (27)) and inhibits binding and LRP-mediated internalization and degradation of all ligands (Moestrup, S. K., *Biochim. Biophys. Acta* 1197:197–213 (1994); Williams, S. E., et al., *J. Biol. Chem.* 267:9035–9040 (1992)), therefore serving as a useful tool for testing whether LRP is involved in endocytosis of a given ligand.

Severe hemophiliacs, who number about 10,000 in the United States, can be treated with infusion of human factor VIII, vWf/factor VIII complex or vWf which will restore the blood's normal clotting ability if administered with sufficient frequency and concentration. However, supplies have been inadequate and problems in therapeutic use occur due to difficulty in isolation and purification, immunogenicity, and the necessity of removing the AIDS and hepatitis infectivity risk.

Several preparations of human plasma-derived factor VIII of varying degrees of purity are available commercially for the treatment of hemophilia A. These include a partially-purified factor VIII derived from the pooled blood of many donors that is heat- and detergent-treated for virus inactivation but contains a significant level of antigenic proteins; and a monoclonal antibody-purified factor VIII that has lower levels of antigenic impurities and viral contamination. At present, there are also five commercially available recombinant human factor VIII products (reviewed by Ananyeva et al. *Expert Opin. Pharmacother.;* 5:1061–1070 (2004)). Unfortunately, human factor VIII is unstable at physiologic concentrations and pH, is present in blood at an extremely low concentration (0.2 µg/ml plasma), has low specific clotting activity and is rapidly cleared from the circulation.

The problems associated with the commonly used, commercially available, plasma-derived or recombinant factor VIII have stimulated significant interest in the development of a better factor VII product. There is a need for a more potent factor VIII; a factor VIII that is stable at a selected pH and physiologic concentration; a factor VIII that is has a longer half-life in circulating blood.

SUMMARY OF THE INVENTION

The present invention relates to a method of increasing the half-life of factor VIII. More specifically, the present invention relates to a mutant of factor VIII having reduced clearance from plasma.

The present invention also relates to a method of increasing the specific activity of factor VIII. The present invention also relates to a mutant of factor VIII having increased specific activity.

Further, the present invention relates to a method of increasing the half-life and increasing the specific activity of factor VIII by use of a mutant factor VIII having reduced clearance and increased specific activity.

In embodiments of the invention, the mutant factor VIII has one or more amino acid substitutions in the A2 domain.

In embodiments of the invention, the substituted amino acid(s) are important for receptor-dependent clearance of factor VIII, such that the resulting mutant factor VIII has a longer (increased) circulating half-life. In other embodiments of the invention, the substituted amino acid(s) are also important for receptor-independent clearance of factor VIII, such that the resulting mutant factor VIII has a longer circulating half-life.

In other embodiments of the invention, amino acid(s) important for HSPG-dependent clearance (receptor dependent and receptor-independent) in the A2 domain and receptor-dependent clearance in the A2 domain are substituted, such that the resulting mutant factor VIII has an increased circulating half-life.

BRIEF DESCRIPTION OF THE FIGURES

(FIG. 4A) Direct binding of $^{125}$I-A2 to MEF cells. The cells were incubated for 2 h at 4° C. with increasing concentrations of $^{125}$I-A2 in the absence (●) or presence (Δ) of a 100-fold molar excess of unlabeled A2. Specific binding (○) was calculated by subtraction of the nonspecific binding (Δ) from total binding (●). (FIG. 4B) Displacement of $^{125}$I-A2 by unlabeled A2, fVIII/vWf complex or vWf. The MEF cells were incubated as above with $^{125}$I-A2 (2 nM) in the presence of increasing concentrations of unlabeled A2 (□), vWf (Δ) or fVIII/vWf complex (●) formed using varying fVIII concentrations (4–512 nM) and fixed vWf concentration (1000 nM). This was followed by a determination of the $^{125}$I-A2 binding to the cells. Each data point represents the mean value and standard deviation of duplicate determinations. The curves show a best fit of the data to a model describing homologous or heterologous ligand displacement from a single class of binding sites using the LIGAND program.

FIGS. 6A–6B. Effect of heparin on the A2-dependent factor Xa generation and interaction between A2 and factor IXa. (FIG. 6A) Effect of heparin on the factor Xa generation assay. The mixtures containing factor IXa (5 nM), PSPC vesicles (10 µM), A2 domain (200 nM) and the indicated concentrations of heparin were incubated for 10 min, and the reactions were started by addition of factor X (300 nM). The initial rates of factor Xa generation (Δ) were determined as described in Example 2. (FIG. 6B) Effect of heparin on the interaction of A2 domain and factor IXa. A2 subunit (300 nM) was preincubated for 15 min with the indicated concentrations of heparin. The anisotropy was measured upon addition of PSPC vesicles (50 µM) and Fl-FFR-factor IXa (30 nM) in the presence (■) or absence (●) of factor X (400 nM) as described in Example 2. In control experiments, A2 subunit was omitted from the mixtures with (□) or without (○) factor X. Each point represents the mean value ±SD of five measurements.

FIGS. 7A–7B. Effect of synthetic peptides on A2-heparin binding. (FIG. 7A) Effect of the A2 domain peptide 558–565 on the binding of A2 to heparin was measured by the SPR technique. Heparin was immobilized on the chip surface as described in Example 2. Binding of the A2 subunit (200 nM) to heparin was measured in the absence (curve 1) or presence of varying concentrations of the peptide (25, 50, 100, 200, 400 and 800 µM, curves 2–7, respectively). (FIG. 7B) Effect of A2 peptides 432–456 (Δ), 484–509 (○) and 558–565 (●) on binding of the A2 subunit to heparin. Equilibrium binding of A2 to immobilized heparin at the indicated concentrations of each peptide was determined as in FIG. 7A. A2 binding in the presence of peptides is expressed as the percentage of the A2 binding when no peptide was added.

FIGS. 12A–12B. The amino acid sequence of mature, B-domainless fVIII (SEQ ID NO:5; composed from GenBank Accession No. X01179). The A2 sequence within fVIII is underlined and the sequence of the LRP binding site (residues 484–509) within A2 is indicated with asterisks. The amino acid residues are shown as one-letter amino acid abbreviations.

FIGS. 13A–13C. The deduced amino acid sequence of full-length factor VIII (SEQ ID NO:2; from GenPep Accession No. CAA25619.1 and GenBank Accession No. X01179).

FIG. 14. The deduced amino acid sequence of RAP (SEQ ID NO:4; GenBank Accession No. M63959). The signal sequence (amino acids 1–34) is underlined and the LDL receptor binding region (amino acids 237–353) is indicated with asterisks.

(FIG. 17A) $^{125}$fVIII (1 nM) and increasing concentrations of mAbs 413 (●) or T5 (○) were added to LRP coated wells as described in FIGS. 15A–15B. In the control experiment (Δ), $^{125}$I-fVIII and increasing concentrations of mAb 413 were added to BSA coated wells. (FIG. 17B) $^{125}$I-fVIII and increasing concentrations of synthetic peptides consisting of the A2 domain residues 484–509 (●) or 432–456 (○) were added to LRP coated wells. In the control experiment (Δ), $^{125}$I-fVIII and increasing concentrations of the peptide 484–509 were added to BSA coated wells. Binding of $^{125}$I-fVIII in the presence antibodies or peptides is expressed as the percentage of its binding, when no competitor was added. The mean and standard deviation of the triplicate measurements are presented.

In FIGS. 21A–21B, 2×10$^5$ of MEF (○, ●) or PEA 13 cells (Δ, ▲) were incubated with 10 nM $^{125}$I-A2 in the absence (closed symbols) or presence (opened symbols) of RAP (1 μM). At the indicated times, the amounts of internalized $^{125}$I-A2 (FIG. 21A) and degraded $^{125}$I-A2 (FIG. 21B) by the MEF and PEA 13 fibroblasts were determined as described in FIGS. 18A–18B. In the experiment (∇), degradation of $^{125}$I-A2 by MEF cells in the presence (0.1 mM) chloroquine is shown. Each data point represents the mean and standard deviation of duplicate determinations. In FIGS. 21C–21D, $^{125}$I-A2 (10 nM) was incubated for 4 h at 37° C. in the wells containing 3×10$^5$ SMC (solid bars) or T2 (open bars) cells in the presence or absence of RAP (1 mM). The amount of $^{125}$I-A2 internalized (FIG. 21C) and degraded (FIG. 21D) by the cells was determined as in FIGS. 18A–18B. The data shown are an average of duplicate determinations ±standard deviation.

DETAILED DESCRIPTION

Figure 1A:
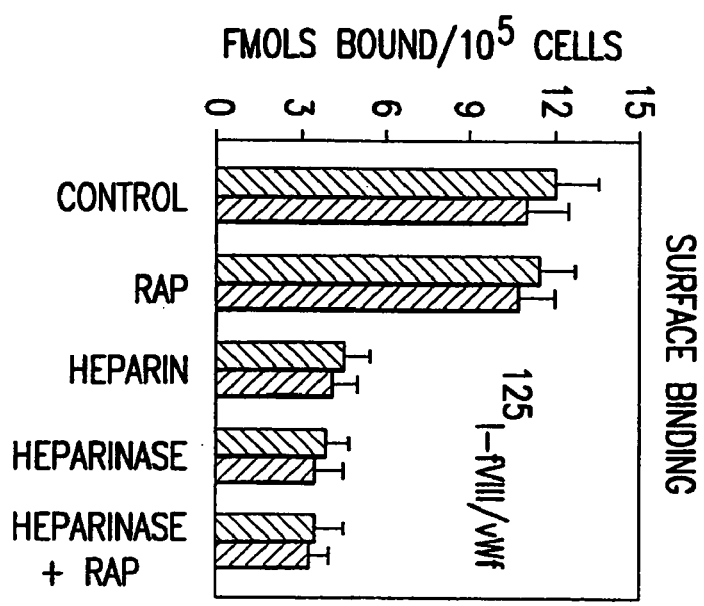
FIGS. 1A–1D. Effect of RAP, heparin and heparinase on $^{125}$I-fVIII/vWf and $^{125}$I-A2 surface binding and degradation in mouse embryonic fibroblasts (MEF). Wells containing 2×10$^5$ of LRP-expressing MEF cells (solid bars) or LRP-deficient PEA 13 cells (open bars) were preincubated with or without heparinase as described in Example 2. This was followed by addition of either 1 nM $^{125}$I-fVIII/vWf complex (FIGS. 1A–1B) or 1 nM $^{125}$I-A2 (FIGS. 1C–1D) in the absence or presence of RAP (1 µM) or heparin (100 µg/ml) and incubation for 6 h at 37° C. Surface binding of $^{125}$I-fVIII and $^{125}$I-A2 (FIGS. 1A and 1C) and degradation (FIGS. 1B and 1D) were subsequently determined as described in Example 2. Each data point represents the mean value and standard deviation of duplicate determinations.

"Factor VIII" (or "coagulation factor VIII"), as used herein, refers to a plasma glycoprotein that is a member of the intrinsic coagulation pathway and is essential to blood coagulation. A congenital X-linked deficiency of biologically active factor VIII results in Hemophilia A, a potentially life-threatening disorder. Unless otherwise specified or indicated, as used herein, "factor VIII" denotes any functional human factor VIII protein molecule in its normal role in coagulation, including any fragment, analog derivative or modified factor VIII. The human factor VIII cDNA nucleotide and full-length predicted amino acid sequences are shown in SEQ ID NOs:1 and 2, respectively. Human factor VIII peptides of the invention include full-length factor VIII, full-length factor VIII minus Met at the N-terminus, mature factor VIII (minus the signal sequence), mature factor VIII with an additional Met at the N-terminus, and/or factor VIII with or without a B domain. Factor VIII of the invention may also include porcine factor VIII. The cDNA and predicted amino acid sequences of the porcine factor VIII are disclosed in U.S. Pat. No. 5,859,204.

"Subunits" of factor VIII, as used herein, are the heavy and light chains of the protein. The heavy chain of factor VIII contains three domains, A1, A2, and B. The light chain of factor VIII also contains three domains, A3, C1, and C2. Factor VIII is synthesized as an approximately 300 kDa single chain protein with internal sequence homology that defines the "domain" sequence NH$_2$-A1-A2-B-A3-C1-C2-COOH.

In a factor VIII molecule, a "domain", as used herein, is a continuous sequence of amino acids that is defined by internal amino acid sequence identity and sites of proteolytic cleavage by thrombin. Unless otherwise specified, factor VIII domains include the following amino acid residues: A1, residues Ala1-Arg372; A2, residues Ser373-Arg740; B, residues Ser741-Arg1648; A3, residues Ser1690-Ile2032; C1, residues Arg2033-Asn2172; C2, residues Ser2173-Tyr2332. The A3-C1-C2 sequence includes residues Ser1690-Tyr2332. The remaining sequence, residues Glu1649-Arg1689, is usually referred to as the factor VIII light chain activation peptide.

A "B-domainless" factor VIII or "B (−)" factor VIII, or fragment of thereof, as used herein, refers to any one of the factor VIII mutants described herein that lacks the B domain. The amino acid sequence of mature, B (−) factor VIII as constructed from GenBank Accession No. X01179 is shown in FIGS. 12A–12B (SEQ ID NO:5). B (−) factor VIII of the invention includes B (−) factor VIII with or without a signal sequence and with or without a Met at the N-terminus.

As used herein, a "mutant factor VIII or fragment thereof" or "factor VIII mutant or fragment thereof" is an active factor VIII molecule or fragment thereof comprising at least one amino acid substitution.

"RAP," as used herein, refers to the receptor-associated protein, also called the α$_2$ macroglobulin receptor-associated protein. RAP reduces receptor-dependent clearance of factor VIII. The human RAP deduced amino acid sequence is shown in FIG. 14 (SEQ ID NO:4; GenBank Accession No. P30533). The RAP cDNA sequence is shown in SEQ ID NO:3 and GenBank Accession No. M63959. Mutant RAP proteins of the invention may have an amino acid substitution at one, two, three, four, five, six, seven, eight, nine, ten, eleven, twelve, thirteen, fourteen, fifteen, sixteen, seventeen, eighteen, nineteen, twenty or more positions of RAP. An amino acid substitution at "position" 327, for example, of RAP, refers to an amino acid substitution at amino acid 327 of the RAP amino acid sequence in GenBank Accession No. P30533.

By "amino acid substitution" is meant a substitution of one amino acid for one of the remaining 19 naturally occurring amino acids. By an amino acid substitution at any one of positions "484 to 509," for example, is meant an amino acid substitution any position in the range, including at positions 484 and 509. The mutant factor VIII or RAP proteins of the invention may have an amino acid substitution at one, two, three, four, five, six, seven, eight, nine, ten, eleven, twelve, thirteen, fourteen, fifteen, sixteen, seventeen, eighteen, nineteen, twenty or more positions.

An amino acid substitution at "position" 499, for example, of factor VIII, refers to an amino acid substitution at position 499 according to the numbering system of Wood et al., Nature 312:330–337 (1984).

"Half-life," as used herein, refers to the half-life of factor VIII in circulation, as determined in animals such as mice, for example, using the method of Examples 1–3. Factor VIII has a half-life of 12–14 hours. As provided herein, methods to increase the half-life of factor VIII would lead to a factor VIII half-life of longer than 12–14 hours.

"Receptor-dependent clearance," as used herein, refers to the receptor-mediated removal of factor VIII from circulation. As described in the examples, receptor-dependant clearance is exhibited by MEF cells and is inhibited by RAP. Receptor-dependent clearance includes, but is not limited to, LRP-mediated clearance of factor VIII. Additional receptors may be involved in receptor-dependent clearance. The terms receptor-"dependent" and receptor-"mediated" are used interchangeably herein.

"Receptor-independent clearance," as used herein, refers to the removal of factor VIII from circulation by means other than receptor-dependent clearance. RAP does not inhibit receptor-independent clearance.

"Heparan sulfate proteoglycan (HSPG)-dependent clearance," as used herein, refers to the removal of factor VIII from circulation by means of cell surface heparan sulfate proteoglycans (HSPGs). HSPG-dependent clearance is inhibited by heparin, heparinase, and protamine. HSPG-dependent clearance includes both receptor-dependent and receptor-independent clearance. "HSPG-dependent, receptor-independent clearance" is exhibited by LRP-deficient cells such as PEA13 cells, and is inhibited by heparin, heparinase, or protamine but is not significantly inhibited by RAP. The terms HSPG-"dependent" and HSPG-"mediated" are used interchangeably herein. "HSPG" and "HSPGs" are used interchangeably herein.

"Factor VIII deficiency," as used herein, includes deficiency in clotting activity caused by production of defective factor VIII, by inadequate or no production of factor VIII, or by partial or total inhibition of factor VIII by inhibitors. Hemophilia A is a type of factor VIII deficiency resulting from a defect in an X-linked gene and the absence or deficiency of the factor VIII protein it encodes. A deficiency in vWf can also cause phenotypic hemophilia A because vWf is an essential component of functional factor VIII. In these cases, the half-life of factor VIII is decreased to such an extent that it can no longer perform its particular functions in blood-clotting.

"Plasma," as used herein, refers to the fluid, non-cellular portion of the blood of humans or animals as found prior to coagulation. It is distinguished from serum, which is obtained after coagulation.

"Pharmaceutically acceptable carrier," as used herein, refers to a non-toxic solid, semisolid or liquid filler, diluent, encapsulating material or formulation auxiliary of any type.

"Patient," as used herein, refers to human or animal individuals receiving medical care and/or treatment.

"Congenital deficiency," as used herein, refers to the condition of an individual that lacks, as a result of heredity, a compound found in normal individuals. Congenital deficiencies are permanent absent transplantation or genetic intervention, which at this time are not guaranteed cures.

"Acquired deficiency," as used herein, refers to the condition of an individual that lacks, as a result of a non-congenital influence, a compound found in normal individuals. Acquired deficiencies are frequently the transient result of other conditions or their treatment, but are nonetheless debilitating and life threatening.

A "fusion protein," as used herein, is the product of a gene in which the coding sequence for one protein is extensively altered, for example, by fusing part of it to the coding sequence for a second protein from a different gene to produce a gene that encodes the fusion protein. As used herein, a fusion protein is a subset of the factor VIII protein or RAP protein described in this application.

A "corresponding" nucleic acid or amino acid or corresponding sequence of either, as used herein, is one present at a site in a factor VIII or mutant factor VIII molecule or fragment thereof that has the same structure and/or function as a site in the factor VIII molecule of another species, although the nucleic acid or amino acid number may not be identical.

"Procoagulant activity," as used herein, refers to factor VIII coagulation activity exhibited in a human factor VIII assay.

"Specific activity," as used herein, refers to the activity that will correct the coagulation defect of human factor VIII deficient plasma. Specific activity is measured in units of clotting activity per milligram total factor VIII protein in a standard assay in which the clotting time of human factor VIII deficient plasma is compared to that of normal human plasma. One unit of factor VIII activity is the activity present in one milliliter of normal human plasma. In the assay, the shorter the time for clot formation, the greater the activity of the factor VIII being assayed. Mutant factor VIII has coagulation activity in a human factor VIII assay. This activity may be less than, equal to, or greater than that of either plasma-derived or recombinant human factor VIII.

"Polypeptides," "molecules" and "proteins," as used herein, includes all polypeptides as described below. The basic structure of polypeptides is well known and has been described in innumerable textbooks and other publications in the art. In this context, the term is used herein to refer to any peptide or protein comprising two or more amino acids joined to each other in a linear chain by peptide bonds. As used herein, the term refers to both short chains, which also commonly are referred to in the art as peptides, oligopeptides and oligomers, for example, and to longer chains, which generally are referred to in the art as proteins, of which there are many types.

It will be appreciated that polypeptides often contain amino acids other than the 20 amino acids commonly referred to as the 20 naturally occurring amino acids, and that many amino acids, including the terminal amino acids, may be modified in a given polypeptide, either by natural processes, such as processing and other post-translational modifications, but also by chemical modification techniques which are well known to the art. Even the common modifications that occur naturally in polypeptides are too numerous to list exhaustively here, but they are well described in basic texts and in more detailed monographs, as well as in a voluminous research literature, and they are well known to those of skill in the art. Among the known modifications which may be present in polypeptides of the present invention are, to name an illustrative few, acetylation, acylation, ADP-ribosylation, amidation, PEGylation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cystine, formation of pyroglutamate, formulation, gamma-carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination.

Such modifications are well known to those of skill and have been described in great detail in the scientific literature. Several particularly common modifications, glycosylation, lipid attachment, sulfation, gamma-carboxylation of glutamic acid residues, hydroxylation and ADP-ribosylation, for instance, are described in most basic texts, such as, for instance *Proteins—Structure and Molecular Properties*, 2nd Ed., T. E. Creighton, W. H. Freeman and Company, New York (1993). Many detailed reviews are available on this subject, such as, for example, those provided by Wold, F., Posttranslational Protein Modifications: Perspectives and Prospects, pp. 1–12 in *Posttranslational Covalent Modification of Proteins*, B. C. Johnson, Ed., Academic Press, New York (1983); Seifter et al., Analysis for protein modifications and nonprotein cofactors, Meth. Enzymol. 182: 626–646 (1990) and Rattan et al., *Protein Synthesis: Post translational Modifications and Aging*, Ann. N.Y. Acad. Sci. 663: 48–62 (1992).

In general, as used herein, the term polypeptide encompasses all such modifications, particularly those that are present in polypeptides synthesized by expressing a polynucleotide in a host cell.

The invention also relates to fragments, "derivatives" and analogs of these polypeptides. The terms "fragment," "derivative" and "analog" when referring to the polypeptides of FIGS. 12A–12B, 13A–13B or 14, means a polypeptide which retains essentially the same biological function or activity as such polypeptide. A mutant, fragment derivative or analog of factor VIII refers to a polypeptide that retains factor VIII procoagulant activity. A mutant, fragment derivative or analog of RAP refers to a polypeptide that retains the ability to reduce receptor-dependent clearance of factor VIII. Thus, an analog includes a proprotein which can be activated by cleavage of the proprotein portion to produce an active mature polypeptide. Fragments, derivatives and analogs are described in detail herein.

A fragment, derivative or analog of the polypeptide of the invention may be (i) one in which one or more of the amino acid residues includes a substituent group, or (ii) one in which the mature polypeptide is fused with another compound, such as a compound to increase the half-life of the polypeptide (for example, polyethylene glycol), or (iii) one in which the additional amino acids are fused to the mature polypeptide, such as a leader or secretory sequence or a sequence which is employed for purification of the mature polypeptide or a proprotein sequence. Such fragments, derivatives and analogs are deemed to be within the scope of those skilled in the art from the teachings herein.

The polypeptide of the present invention may be a recombinant polypeptide, a natural polypeptide or a synthetic polypeptide. In certain embodiments it is a recombinant polypeptide.

Further embodiments in this regard include mutants, analogs and fragments; and mutants and analogs of the fragments, having the defined activity and/or having the amino acid sequence of the polypeptides of FIGS. 12A–12B, 13A–13C or 14.

The polypeptides and polynucleotides of the present invention are preferably provided in an isolated form, and preferably are purified to homogeneity.

"Polynucleotide(s)" generally refers to any polyribonucleotide or polydeoxyribonucleotide, which may be unmodified RNA or DNA or modified RNA or DNA. Thus, for instance, polynucleotides as used herein refers to, among others, single- and double-stranded DNA, DNA that is a mixture of single- and double-stranded regions, single- and double-stranded RNA, and RNA that is mixture of single- and double-stranded regions, hybrid molecules comprising DNA and RNA that may be single-stranded or, more typically, double-stranded or a mixture of single- and double-stranded regions. In addition, polynucleotide as used herein refers to triple-stranded regions comprising RNA or DNA or both RNA and DNA. The strands in such regions may be from the same molecule or from different molecules. The regions may include all of one or more of the molecules, but more typically involve only a region of some of the molecules. One of the molecules of a triple-helical region often is an oligonucleotide.

As used herein, the term polynucleotide includes DNAs or RNAs as described above that contain one or more modified bases. Thus, DNAs or RNAs with backbones modified for stability or for other reasons are "polynucleotides" as that term is intended herein. Moreover, DNAs or RNAs comprising unusual bases, such as inosine, or modified bases, such as tritylated bases, to name just two examples, are polynucleotides as the term is used herein.

It will be appreciated that a great variety of modifications have been made to DNA and RNA that serve many useful purposes known to those of skill in the art. The term polynucleotide as it is employed herein embraces such chemically, enzymatically or metabolically modified forms of polynucleotides, as well as the chemical forms of DNA and RNA characteristic of viruses and cells, including simple and complex cells, inter alia.

Polynucleotides of the present invention may be in the form of RNA, such as mRNA, or in the form of DNA, including, for instance, cDNA and genomic DNA obtained by cloning or produced by chemical synthetic techniques or by a combination thereof. The DNA may be double-stranded or single-stranded. Single-stranded DNA may be the coding strand, also known as the sense strand, or it may be the non-coding strand, also referred to as the anti-sense strand.

Polynucleotides of the present invention may include, but are not limited to the coding sequence for the mature polypeptide, by itself; the coding sequence for the mature polypeptide and additional coding sequences, such as those encoding a leader or secretory sequence, such as a pre-, or pro- or prepro-protein sequence; the coding sequence of the mature polypeptide, with or without the aforementioned additional coding sequences, together with additional, non-coding sequences, including for example, but not limited to introns and non-coding 5' and 3' sequences, such as the transcribed, non-translated sequences that play a role in transcription, mRNA processing—including splicing and polyadenylation signals, for example—ribosome binding and stability of mRNA; additional coding sequence which codes for additional amino acids, such as those which provide additional functionalities. Thus, for instance, the polypeptide may be fused to a marker sequence, such as a peptide, which facilitates purification of the fused polypeptide. In certain embodiments of this aspect of the invention, the marker sequence is a hexahistidine peptide, such as the tag provided in a pQE vector (Qiagen, Inc.), among others, many of which are commercially available. As described in Gentz et al., *Proc. Natl. Acad. Sci., USA* 86: 821–824 (1989), for instance, hexa-histidine provides for convenient purification of the fusion protein. The HA tag corresponds to an epitope derived of influenza hemagglutinin protein, which has been described by Wilson et al., *Cell* 37: 767 (1984), for instance.

An "effective amount" of an agent, as used herein, is an amount of such agent that is sufficient to bring about a desired result, especially upon administration of such agent to an animal or human.

The term "administration" is meant to include introduction of polypeptides or polynucleotides of the invention into an animal or human by any appropriate means known to the medical art, including, but not limited to, injection, oral, enteral, transdermal and parenteral (e.g., intravenous) administration.

The term "pharmaceutically acceptable salt" is intended to include salts of the mutant factor VIII or RAP of the invention. Such salts can be formed from pharmaceutically acceptable acids or bases, such as, for example, acids such as sulfuric, hydrochloric, nitric, phosphoric, etc., or bases such as alkali or alkaline earth metal hydroxides, ammonium hydroxides, alkyl ammonium hydroxides, etc.

The term "pharmaceutically acceptable composition" is intended to include solvents, carriers, diluents, and the like, which are utilized as additives or vehicles to preparations of the mutant factor VIII or RAP of the invention so as to provide a carrier or adjuvant for the administration of such compounds to patients (human or animal) in need of the same. Such additives can perform certain functions, such as, for example, provide the proper ionic conditions for administration, stabilize the mutant factor VIII or RAP against inactivation or degradation, and/or increase the half-life of the mutant factor VIII or RAP. A pharmaceutically acceptable composition is medically compatible with the host to which it is being administered.

The term "treatment" or "treating" is intended to include the administration of the pharmaceutically acceptable compositions of the invention comprising effective amounts of mutant factor VIII or RAP (polypeptides or polynucleotides) of the invention to a patient for purposes which may include prophylaxis, amelioration, prevention or cure of a medical disorder.

A material is said to be "substantially free of natural contaminants" if it has been substantially purified from materials with which it is normally and naturally found before such purification and those contaminants normally and naturally found with the substance in vivo or in vitro are substantially absent from the final preparation of the material. When administered to a subject in need of treatment, the mutant factor VIII or RAP of the invention is substantially free of natural contaminants which associate with the mutant factor VIII or RAP either in vivo (in the host from which the mutant factor VIII or RAP was isolated), or in vitro (as a result of a chemical synthesis). By "substantially absent" is meant that such contaminants are either completely absent or are present at such low concentrations that their presence (1) does not interfere with the desired therapeutic effect of the active agent in the therapeutically acceptable composition when such composition is administered to a patient in need of same and (2) does not harm the patient as the result of the administration of such composition.

Since current information indicates that the B domain has no known effect on factor VIII function, in some embodiments the B domain is deleted ("B domain (−)" or "B domainless") in the mutant factor VIII molecule or fragments thereof ("B(−) factor VIII" or "B domainless factor VIII") prepared by any of the methods described herein.

Generation of mutant(s) with a prolonged lifetime may be a promising approach to increase the efficacy and reduce the cost of fVIII infusion therapy. The invention provides methods of increasing the half-life of factor VIII by mutating factor VIII, and further provides methods of increasing the half-life of factor VIII using receptor-associated protein (RAP).

Factor VIII Mutants: A2 Domain

A recombinant mutant factor VIII having reduced receptor-dependent clearance and/or reduced receptor-independent clearance, and/or having superior coagulant activity, compared to human factor VIII, may be less expensive to make than plasma-derived factor VIII and may decrease the amount of factor VIII required for effective treatment of factor VIII deficiency.

The present invention provides active recombinant mutant factor VIII molecules or fragments thereof comprising at least one amino acid substitution in the A2 domain, polynucleotides encoding these, methods of producing and isolating them, and methods for characterizing their coagulant and plasma clearance properties.

Factor VIII clearance from circulation is mediated by two pathways. One pathway—HSPGs-dependent, receptor-independent clearance—involves heparan sulfate proteoglycans (HSPGs). Another pathway—receptor-dependent clearance—involves HSPGs and low density lipoprotein receptor related protein (LRP). The present invention provides methods of increasing the half-life of factor VIII by reducing clearance via these pathways by substituting one or more amino acids in the A2 domain.

Receptor-Dependent Clearance. In one embodiment, the invention provides a method of increasing the half-life of factor VIII by substituting amino acids in the factor VIII A2 domain. In another embodiment, the invention provides mutant factor VIII and fragments thereof, and the polynucleotides encoding same, which have an increased circulating half-life over human factor VIII. In this embodiment, the increased circulating half-life is due to a reduction in receptor-dependent clearance of factor VIII. As shown in the Examples, amino acids in the factor VIII A2 domain interact with at least one receptor that mediates A2 clearance and factor VIII clearance from plasma.

Thus, in accordance with an embodiment of the invention, the factor VIII mutants may have an amino acid substitution at one or more positions within the A2 domain. More particularly, the factor VIII mutants may have an amino acid substitution at position Lys(466) and/or position Arg(471). The factor VIII mutants may also have an amino acid substitution at one or more positions chosen from Lys(380), Arg(484), Tyr(487), Ser(488), Arg(489), Arg(490), His (497), His(499), Lys(523), and Lys(556).

As discussed in Example 1 below, amino acid substitutions at these positions were demonstrated to have reduced affinity for LRP. Accordingly, another embodiment of the invention provides a method for increasing the half-life of factor VIII. The method includes substituting an amino acid for a residue at position Lys(466) and/or position Arg(471), where the resulting factor VIII has procoagulant activity. In addition, in the inventive method, one or more positions chosen from Lys(380), Arg(484), Tyr(487), Ser(488), Arg (489), Arg(490), His(497), His(499), Lys(523), and Lys (556) may also be substituted.

In yet another embodiment of the invention, the factor VIII mutants may have an amino acid substitution at one or more positions chosen from Lys(377), His(378), and Lys (466). The factor VIII mutants may also have an amino acid substitution at one or more positions chosen from Lys(380), Ser(488), Arg(489), Arg(490), Leu(491), Lys(493), Lys (496), His(497), His(499), Lys(512), Lys(523), and Lys (556).

As discussed in Example 1 below, amino acid substitutions at these positions were demonstrated to have increased specific activity over non-substituted factor VIII. Accordingly, another embodiment of the invention provides a method for increasing the specific activity of factor VIII. In the inventive method, an amino acid may be substituted for a residue at one or more positions chosen from Lys(377), His(378), Lys(380), Lys(466), Ser(488), Arg(489), Arg (490), Leu(491), Lys(493), Lys(496), His(497), His(499), Lys(512), Lys(523), and Lys(556), wherein the resulting factor VIII has procoagulant activity.

In contrast to previous work describing regions of a factor VIII molecule that was substituted for homologous sequences of porcine FVIII, which has been described as having a higher specific activity than human FVIII (Lollar et al., *J. Biol. Chem.* 267:23652–23657), the fact that factor VIII mutants of the present invention, i.e., reconstituted human factor VIII with selected single amino acid substitutions have increased specific activity compared to non-substituted human factor VIII was unexpected.

In another embodiment of the invention, the factor VIII mutants may have an amino acid substitution at more than one position which can result in increased half-life and increased specific activity. For example, a factor VIII mutant may have one or more amino acid substitutions which increase the half life of factor VIII in combination with one or more amino acid substitutions which increase the specific activity of factor VIII. Illustratively, a factor VIII mutant having an amino acid substitution at Arg(471), which was demonstrated in Example 1 as having reduced affinity for LRP, and an amino acid substitution having an amino acid substitution at Lys(496), which was demonstrated in Example 1 as having increased specific activity, may have increased half-life and increased specific activity.

In generating a mutant factor VIII of the present invention, the amino acid at a particular position may be substituted with any of the 19 other naturally occurring amino acids. Amino acid substitutions include conservative and non-conservative substitutions.

Conservative amino acid substitutions include, for example, the substitution of an acidic amino acid with another acidic amino acid, a basic amino acid with another basic amino acid, a hydrophobic amino acid with a another hydrophobic amino acid, a polar amino acid with another polar amino acid, or an aromatic amino acid with another aromatic amino acid. Conservative amino acid substitutions are well known in the art.

Thus, an example of a conservative substitution is the substitution of Lys with Arg, while an example of a non-conservative substitution is the substitution of Lys with Asp, Glu, Tyr, Asn, Gln, Thr, Ser, Cys, Trp, Phe, Pro, Met, Val, Leu, Ile, Trp, Gly or Ala.

A2 amino acid substitutions of the invention are those that inhibit the interaction of factor VIII with its clearance receptor(s). Thus, nonconservative A2 amino acid substitutions are preferred over conservative substitutions. In an embodiment of the invention, the amino acid is substituted with Ala.

In various embodiments of the invention, in addition to the substituted positions described above, the factor VIII mutants may also have an amino acid substitution at one or more other positions from 484 to 509, or outside this range, as described in International Application Pub. No. WO 00/71714 A2, incorporated by reference herein in its entirety, as well as for methods of increasing the half-life and/or specific activity of factor VIII. Illustratively, the factor VIII mutants may also have an amino acid substitution at one or more of positions 480, 481, 482, 483, 484, 489, 490, 493, 496, 499, 510, 511, 512, or 513.

HSPG-Dependent, Receptor-Independent Clearance. In other embodiments, in addition to the factor VIII mutants described above, the invention provides mutant factor VIII and fragments thereof, and polynucleotides encoding same, which have an increased circulating half-life over human factor VIII due to a reduction in heparin sulfate proteoglycan (HSPG)-dependent, receptor-independent clearance of factor VIII. As shown in Example 2, particular amino acids in the factor VIII A2 domain interact with HSPGs in the HSPG-dependent clearance pathway. These mutants are described in International Application Pub. No. WO 02/060951 A2, incorporated by reference herein in its entirety. These mutants can be used in combination with the mutants described above, as well as for methods of increasing the half-life and/or specific activity of factor VIII. Illustratively, the factor VIII mutants may also have an amino acid substitution at one or more of positions 380, 512, 523, 527, 556, 562, 570, 571, and 659.

Factor VIII Proteins and Polynucleotides

Specifically provided as an exemplary embodiment is active recombinant human factor VIII having substituted amino acids in the A2 domain, polynucleotides encoding it, and methods of producing, isolating, and characterizing its activity. The methods by which this mutant is prepared can also be used to prepare active recombinant factor VIII or fragments thereof having substituted amino acids in domains other than A2. One skilled in the art will recognize that these methods also demonstrate how other recombinant mutant factor VIII molecules or fragments thereof can be prepared in which amino acids are substituted. Additionally, recombinant methods are described in *Current Protocols in Molecular Biology*, F. M. Ausubel et al., eds. (1991); and Sambrook, J., et al., Molecular Cloning. A Laboratory Manual.

In an embodiment of the invention, residues critical for binding to LRP may be identified by mutational analysis of the major LRP-binding site of factor VIII located within the A2 domain residues 484–509 and residues spatially close to this region. For example, alanine-scanning mutagenesis may be conducted based on a model of factor VIII 3-D-structure (Stoilova-McPhie et al., *Blood* 99:1215–23 (2002). A2 mutants can be generated that target positively charged residues. Illustratively, A2 mutants may be expressed in a baculoviris system, purified from cell culture, and tested for binding to LRP in a surface plasmon resonance-based assay. The activity of reconstituted factor VIIIa may also be determined. These methods are discussed in detail in Example 1, below.

Mutant factor VIII may be prepared starting with human cDNA (Biogen, Inc.) encoding the factor VIII sequence. In an embodiment, the factor VIII encoded by this cDNA includes domains A1-A2-A3-C1-C2, lacking the entire B domain, and corresponds to amino acid residues 1–740 and 1649–2332 of single chain human factor VIII (see SEQ ID NO:2), according to the numbering system of Wood et al., 312 Nature 330–337 (1984).

The mutant factor VIII cDNA may be cloned into expression vectors for ultimate expression of active factor VIII protein molecules in cultured cells by established techniques, as described by Selden, R. F., "Introduction of DNA into mammalian cells," in *Current Protocols in Molecular Biology*, F. M. Ausubel et al., Ids (1991).

In an embodiment of the invention, a cDNA encoding mutant factor VIII can be inserted in a mammalian expression vector, such as ReNeo, to form a mutant factor VIII construct. Preliminary characterization of the mutant factor VIII is accomplished by insertion of the mutant cDNA into the mammalian expression vector and transient expression of the mutant protein in COS-7 cells. A determination of whether active protein is expressed can then be made. The expression vector construct is used further to stably transfect cells in culture, such as baby hamster kidney cells, using methods that are routine in the art, such as liposome-mediated transfection (Lipofectin™, Life Technologies, Inc.). Expression of recombinant mutant factor VIII protein can be confirmed, for example, by sequencing, Northern and Western blotting, or polymerase chain reaction (PCR). Mutant factor VIII protein in the culture media in which the transfected cells stably expressing the protein are maintained can be precipitated, pelleted, washed, and resuspended in an appropriate buffer, and the recombinant mutant factor VIII protein purified by standard techniques, including immunaffinity chromatography using, for example, monoclonal anti-A2-Sepharose™.

In another embodiment, the mutant factor VIII comprising amino acid substitution(s) can be expressed as a fusion protein from a recombinant molecule in which a sequence encoding a protein or peptide that enhances, for example, stability, secretion, detection, isolation, or the like is inserted in place adjacent to the factor VIII coding sequence. Established protocols for use of homologous or heterologous species expression control sequences including, for example, promoters, operators, and regulators, in the preparation of fusion proteins are known and routinely used in the art. (See *Current Protocols in Molecular Biology*, Ausubel, F. M., et al., Ids, Wiley Interscience, N.Y.)

Other vectors, including both plasmid and eukaryotic viral vectors, may be used to express a recombinant gene construct in eukaryotic cells depending on the preference and judgment of the skilled practitioner (see, for example, Sambrook et al., Chapter 16). Other vectors and expression systems, including bacterial, yeast, and insect cell systems, can be used.

The purified mutant factor VIII or fragment thereof can be assayed for amount and for coagulation activity by standard assays including, for example, the plasma-free factor VIII assay, the one-stage clotting assay, and the enzyme-linked immunosorbent assay using purified recombinant human factor VIII as a standard.

Recombinant mutant factor VIII protein can be expressed in a variety of cells commonly used for culture and recombinant mammalian protein expression. An illustrative cell line, available from the American Type Culture Collection, Manassas, Va., is baby hamster kidney cells, which are cultured using routine procedure and media.

Any mutant factor VIII construct having an amino acid substitution at one or more positions in the A2 domain as described can be assayed by standard procedures for coagulant activity and may be assayed as described herein to identify mutant factor VIII molecules with enhanced coagulant activity and/or reduced receptor-mediated clearance and/or reduced HSPG-dependent clearance. Mutant molecules may also be identified that have reduced coagulant activity compared to human or porcine factor VIII but also have reduced receptor-mediated clearance or reduced HSPG-dependent clearance. One skilled in the art will recognize that mutant factor VIII molecules or fragments thereof having less, equal, or greater coagulant activity, compared to human or porcine factor VIII, are useful for treating patients who have a factor VIII deficiency. The methods described herein to prepare active recombinant mutant factor VIII with amino acid substitution(s) in the A2 domain can be used to prepare active recombinant mutant factor VIII protein with amino acid substitution(s) in the C2 domain or fragments thereof.

These molecules can be expressed in COS-7 cells and baby hamster kidney cells as described above. They can be purified to homogeneity using methods known in the art, such as heparin-Sepharose™ and immunoaffinity chromatography. Protein concentration can be estimated by absorption of ultraviolet light at $A_{280}$, and the specific activity of the constructs can be determined by dividing coagulant activity (measured in units per ml by single stage clotting assay) by $A_{280}$. Human factor VIII has a specific activity of approximately 3000–4000 U/$A_{280}$, whereas porcine factor VIII has a specific activity of approximately 20,000 U/$A_{280}$. In an embodiment, the coagulant mutant factor VIII has a specific activity of 3000 U/$A_{280}$. In another embodiment, the coagulant mutant factor VIII has a specific activity of 3000 U/$A_{280}$. The specific activity of mutant factor VIII may be anywhere in the range of 1000–20,000 U/$A_{280}$.

As described herein, site-directed mutagenesis techniques may be used to identify mutant protein with coagulant activity that can be enhanced, equal to, or reduced, compared to human factor VIII, but preferably is enhanced. Oligonucleotide-directed mutagenesis can be used as described in Kunkel, T. A., et al., *Meth. Enzymol.* 204: 125–139 (1991).

The mutant factor VIII proteins of the invention may have an amino acid substitution at one, two, three, four, five, six, seven, eight, nine, ten, eleven, twelve, thirteen, fourteen, fifteen, sixteen, seventeen, eighteen, nineteen, twenty or more positions of factor VIII. The mutant factor VIII molecules of the invention may have amino acid substitutions in more than one domain, such as having an amino acid substitution both in the A2 domain and in the C2 domain.

The present invention contemplates that mutant factor VIII cDNA and protein can be characterized by methods that are established and routine, such as DNA sequencing, coagulant activity assays, mass by ELISA and by UV absorbency at 280 nm of purified mutant factor VIII, specific coagulant activity (U/mg), SDS-PAGE of purified mutant factor VIII, and the like. Other known methods of testing for clinical effectiveness may be required, such as amino acid, carbohydrate, sulfate, or metal ion analysis.

Factor VIII Mutants: C2 Domain

The same methods employed for preparing mutant human factor VIII having A2 domain amino acid substitution(s) can be used to prepare other recombinant mutant factor VIII protein and fragments thereof and the polynucleotides encoding these, such as mutant factor VIII having amino acid substitutions in the C2 domain.

Mutant human factor VIII molecules with amino acid substitution(s) in the C2 domain, which have reduced or no receptor-independent clearance can be identified. More specifically, the procedures can be the same or similar to those described herein for amino acid substitution in the A2 domain (by alanine scanning mutagenesis, site-directed mutagenesis, etc.,) substituting amino acids in the C2 domain of B (−) factor VIII; insertion into an expression vector, such as pBluescript; expression in cultured cells; and routine assay for coagulant activity and receptor-independent clearance.

The C2 domain consists of amino acid residues 2173–2332. Within this 154 amino acid region, positions 2303–2332 are involved in both phospholipid binding and vWf binding. A synthetic peptide of factor VIII amino acids 2310–2320 (in which residues 2310 and 2320 are covalently linked) competes with factor VIII for phospholipid binding. A comparison of factor V, which does not bind vWf, and factor VIII reveals 5 amino acids within positions 2311–2319 that are unique to factor VIII. Although not being bound by any theory, these unique positions (Gln2311, Ser 2312, Val 2314, His2315 and Gln2316) are important for receptor-independent clearance, but are not critical for vWf binding.

Thus, one embodiment of the present invention includes mutant factor VIII having an amino acid substitution at one or more of positions 2173–2332 in the C2 domain. In another embodiment, the mutant factor VIII can have an amino acid substitution at one or more positions 2311–2319 in the C2 domain.

The amino acid at a particular position can be substituted with any of the 19 other naturally occurring amino acids, including nonconservative or conservative substitutions. C2 amino acid substitutions of the invention may be those that inhibit the interaction of factor VIII with phospholipid.

Additional embodiments of the present invention include a method of treating hemophilia by administering a C2 domain mutant of factor VIII, pharmaceutically acceptable compositions comprising a C2 domain mutant of factor VIII either alone or in combination with RAP, and polynucleotides encoding a C2 domain mutant of factor VIII.

Furthermore, the amino acid substitution(s) in the C2 domain can be combined with amino acid substitution(s) in the A2 domain, to produce a mutant factor VIII with increased half-life.

Receptor Associated Protein (RAP)

An embodiment of the present invention includes a method of increasing the half-life of factor VIII by administering RAP as a fragment, mutant or analog. In one aspect, the RAP fragment, mutant or analog retains LRP binding activity. In another aspect, the RAP fragment, mutant or analog has increased affinity for LRP as compared to the naturally occurring RAP.

In one embodiment, the RAP is a fragment having LRP binding activity. Such RAP fragments may comprise 10, 20, 30, 40, 50, 60, 75, 100, 125, 150, 175, 200, 250, 300 or 350 or more contiguous amino acids.

In an embodiment, RAP comprises amino acids 1 to 357 of FIG. 14 (full-length RAP; amino acids 19 to 323 of SEQ ID NO:4). RAP contains a signal sequence 34 amino acids in length. Thus, in another embodiment, RAP comprises amino acids 35 to 357 of FIG. 4 (mature RAP; amino acids 1 to 323 of SEQ ID NO:4.).

In another embodiment of the present invention, RAP contains an N-terminal or a C-terminal deletion, or a combination of N- and C-terminal deletions. N-terminal deletions often result in a protein with increased stability. Thus, for example, deleting between 1 and 50 amino acids from the N-terminus of mature RAP is useful to produce a more stable RAP. Therefore, additional embodiments of the present invention include, for example, RAP comprising amino acids 36–357, 37–357, 38–357, 39–357, 40–357, 41–357, 42–357, 43–357, 44–357, 45–357, 46–357, 47–357, 48–357, 49–357, 50–357, 51–357, 52–357, 53–357, 54–357, 55–357, 56–357, 57–357, 58–357, 59–357, 60–357, 61–357, 62–357, 63–357, 64–357, 65–357, 66–357, 67–357, 68–357, 69–357, 70–357, 71–357, 72–357, 73–357, 74–357, 75–357, 76–357, 77–357, 78–357, 79–357, 80–357, 81–357, 82–357, 83–357, 84–357 and 85–357 of FIG. 14 (positions 1–323, 2–323, 3–323, 4–323, 5–323, 6–323, 7–323, 8–323, 9–323, 10–323, 11–323, 12–323, 13–323, 14–323, 15–323, 16–323, 17–323, 18–323, 19–323, 20–323, 21–323, 22–323, 23–323, 24–323, 25–323, 26–323, 27–323, 28–323, 29–323, 30–323, 31–323, 32–323, 33–323, 34–323, 35–323, 36–323, 37–323, 38–323, 39–323, 40–323, 41–323, 42–323, 43–323, 44–323, 45–323, 46–323, 47–323, 48–323, 49–323 and 50–323 of SEQ ID NO:4).

The LDL receptor binding domain encompasses amino acids 237 to 353 of FIG. 14 (amino acids 203 to 319 of SEQ ID NO:4). Thus, an embodiment of the present invention is RAP comprising amino acids 237 to 353 (amino acids 203 to 319 of SEQ ID NO:4).

Another embodiment of the present invention is a polynucleotide encoding RAP.

In another embodiment of the present invention, RAP or a polynucleotide encoding RAP is used to treat hemophilia either alone or in combination with a factor VIII mutant.

Additional embodiments of the present invention include pharmaceutically acceptable compositions comprising RAP alone or in combination with one or more factor VIII mutants.

Pharmaceutically Acceptable Compositions

Pharmaceutically acceptable compositions comprising mutant factor VIII and/or RAP, alone or in combination with appropriate pharmaceutical stabilization compounds, delivery vehicles, and/or carrier vehicles, are prepared according to known methods, as described in *Remington's Pharmaceutical Sciences* by E. W. Martin.

In one embodiment, the carriers or delivery vehicles for intravenous infusion are physiological saline or phosphate buffered saline.

In another embodiment, suitable stabilization compounds, delivery vehicles, and carrier vehicles include but are not limited to other human or animal proteins such as albumin.

Phospholipid vesicles or liposomal suspensions may also be pharmaceutically acceptable carriers or delivery vehicles. These can be prepared according to methods known to those skilled in the art and can contain, for example, phosphatidylserine/phosphatidylcholine or other compositions of phospholipids or detergents that together impart a negative charge to the surface, since factor VIII binds to negatively charged phospholipid membranes. Liposomes may be prepared by dissolving appropriate lipid(s) (such as stearoyl phosphatidyl ethanolamine, stearoyl phosphatidyl choline, arachadoyl phosphatidyl choline, and cholesterol) in an inorganic solvent that is then evaporated, leaving behind a thin film of dried lipid on the surface of the container. An aqueous solution of the mutant factor VIII and/or RAP is then introduced into the container. The container is then swirled by hand to free lipid material from the sides of the container and to disperse lipid aggregates, thereby forming the liposomal suspension.

Mutant factor VIII and/or RAP can be combined with other suitable stabilization compounds, delivery vehicles, and/or carrier vehicles, including vitamin K dependent clotting factors, tissue factor, and von Willebrand factor (vWf) or a fragment of vWf that contains the factor VIII binding site, and polysaccharides such as sucrose.

Mutant factor VIII can be stored bound to vWf to increase the shelf-life of the mutant molecule. Additionally, lyophilization of factor VIII can improve the yield of active molecules in the presence of vWf. Lyophilization can also improve the yield of RAP. Current methods for storage of human and animal factor VIII used by commercial suppliers can be employed for storage of mutant factor VIII or RAP. These methods include: (1) lyophilization of factor VIII in a partially-purified state (as a factor VIII "concentrate" that is infused without further purification); (2) immunoaffinity-purification of factor VIII by the Zimmerman method and lyophilization in the presence of albumin, which stabilizes the factor VIII; (3) lyophilization of recombinant factor VIII in the presence of albumin.

Additionally, factor VIII has been indefinitely stable at 4° C. in 0.6 M NaCl, 20 mM MES, and 5 mM $CaCl_2$ at pH 6.0 and also can be stored frozen in these buffers and thawed with minimal loss of activity.

Methods of Treatment

Mutant factor VIII and/or RAP may be used to treat uncontrolled bleeding due to factor VIII deficiency (e.g., intraarticular, intracranial, or gastrointestinal hemorrhage) in hemophiliacs with and without inhibitory antibodies and in patients with acquired factor VIII deficiency due to the development of inhibitory antibodies. The active materials may be administered intravenously.

Factor VIII is classically defined as that substance present in normal blood plasma that corrects the clotting defect in plasma derived from individuals with hemophilia A. The coagulant activity in vitro of purified and partially-purified forms of factor VIII is used to calculate the dose of factor VIII for infusions in human patients and is a reliable indicator of activity recovered from patient plasma and of correction of the in vivo bleeding defect. There are no reported discrepancies between standard assay of novel factor VIII molecules in vitro and their behavior in the dog infusion model or in human patients, according to Lusher, J. M., et al., *New. Engl. J. Med.* 328:453–459 (1993); Pittman, D. D., et al., *Blood* 79:389–397 (1992), and Brinkhous et al., *Proc. Natl. Acad. Sci.* 82:8752–8755 (1985).

Usually, the desired plasma factor VIII level to be achieved in the patient through administration of the mutant factor VIII is in the range of 30–100% of normal. In a mode of administration of the mutant factor VIII, the composition is given intravenously at a dosage in the range from about 5 to 50 units/kg body weight, or in a range of 10–50 units/kg body weight, or at a dosage of 20–40 units/kg body weight; the interval frequency is in the range from about 8 to 24 hours (in severely affected hemophiliacs); and the duration of treatment in days is in the range from 1 to 10 days or until the bleeding episode is resolved. See, e.g., Roberts, H. R., and M. R. Jones, "Hemophilia and Related Conditions—Congenital Deficiencies of Prothrombin (Factor II, Factor V, and Factors VII to XII)," Ch. 153, 1453–1474, 1460, in *Hematology*, Williams, W. J., et al., ed. (1990).

Administration of an effective amount of RAP will result in similar levels of factor VIII in patient blood as indicated above. Patients with inhibitors may require more mutant factor VIII, or patients may require less mutant factor VIII because of its higher specific activity than human factor VIII or increased plasma half-life. Likewise, patients may require more or less RAP, depending on RAP's binding affinity to LRP or other factor VIII clearance receptor, or depending on its stability in circulating blood. As in treatment with human or porcine factor VIII, the amount of mutant factor VIII or RAP infused is defined by the one-stage factor VIII coagulation assay and, in selected instances, in vivo recovery is determined by measuring the factor VIII in the patient's plasma after infusion. It is to be understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the claimed composition.

Administration

In a embodiment of the invention, pharmaceutically acceptable compositions of mutant factor VIII or RAP alone or in combination with stabilizers, delivery vehicles, and/or carriers are infused into patients intravenously according to the same procedure that is used for infusion of human or animal factor VIII.

The treatment dosages of mutant factor VII or RAP composition that must be administered to a patient in need of such treatment will vary depending on the severity of the factor VIII deficiency. Generally, dosage level is adjusted in frequency, duration, and units in keeping with the severity and duration of each patient's bleeding episode. Accordingly, the mutant factor VIII or RAP is included in the pharmaceutically acceptable carrier, delivery vehicle, or stabilizer in an amount sufficient to deliver to a patient a therapeutically effective amount of the mutant protein to stop bleeding, as measured by standard clotting assays.

Treatment can take the form of a single intravenous administration of the composition or periodic or continuous administration over an extended period of time, as required. Alternatively, mutant factor VIII or RAP can be administered subcutaneously or orally with liposomes in one or several doses at varying intervals of time. Mutant factor VIII or RAP can also be used to treat uncontrolled bleeding due to factor VIII deficiency in hemophiliacs who have developed antibodies to human factor VIII.

Suitable examples of sustained-release preparations include semipermeable matrices of solid hydrophobic polymers containing the protein, which matrices are in the form of shaped articles, e.g. films, or microcapsules. Examples of sustained-release matrices include polyesters, hydrogens, e.g., poly(2-hydroxyethyl-methacrylate) as described by Langer et al., *J. Biomed. Mater. Res.* 15:167–277 (1981) and Langer, *Chem. Tech.* 12: 98–105 (1982) or poly(vinylalcohol), polylactides (U.S. Pat. No. 3,773,919, EP 58,481), copolymers of L-glutamic acid and gamma ethyl-L-glutamate (Sidman et al., *Biopolymers* 22:547–556 (19831)), non-degradable ethylene-vinyl acetate (Langer et al., supra), degradable lactic acid-glycolic acid copolymers such as the Lupron Depot™ (injectable microspheres composed of lactic acid-glycolic acid copolymer and leuprolide acetate), and poly-D-(–)-3-hydroxybutyric acid (EP 133, 988). While polymers such as ethylene-vinyl acetate and lactic acid-glycolic acid enable release of molecules for over 100 days, certain hydrogels release proteins for shorter time periods. When encapsulated proteins remain in the body for a long time, they may denature or aggregate as a result of exposure to moisture at 37° C., resulting in a loss of biological activity and possible changes in immunogenicity. Rational strategies can be devised for protein stabilization depending on the mechanism involved. For example, if the aggregation mechanism is discovered to be intermolecular S—S bond formation through thio-disulfide interchange, stabilization can be achieved by modifying sulfhydryl residues, lyophilizing from acidic solutions, controlling moisture content, using appropriate additives, and developing specific polymer matrix compositions.

Sustained-release blood factor compositions also include liposomally entrapped blood factor or antibody. Liposomes containing the claimed blood factor or antibody are prepared by methods known per se: DE 3,218,121; Epstein et al., Proc. Natl. Acad. Sci. USA, 82: 3688–3692 (1985); Hwang et al., Proc. Natl. Acad. Sci. USA, 77: 4030–4034 (1980); EP 52,322; EP 36,676; EP 88,046; EP 143,949; EP 142,641; Japanese patent application 83-118008; U.S. Pat. Nos. 4,485,045 and 4,544,545; and EP 102,324. Ordinarily the liposomes are of the small (about 200–800 Angstroms) unilamelar type, the selected proportion being adjusted for the optimal blood factor therapy. Liposomes with enhanced circulation time are disclosed in U.S. Pat. No. 5,013,556. Additionally, Giles, A. R., et al. *Brit. J. Hematol.* 69:491–497 (1988) describe the formulation of factor Xa in phosphatidylcholine-phosphatidylserine vesicles.

Additionally, mutant factor VIII or RAP can be administered by transplant of cells genetically engineered to produce the protein or by implantation of a device containing such cells, as described below.

Gene Therapy

Polynucleotides encoding the mutant factor VIII or RAP may be employed in accordance with the present invention by expression of such mutant factor VIII or RAP in vivo, in treatment modalities often referred to as "gene therapy."

Mutant factor VIII or RAP can also be delivered by gene therapy in the same way that human factor VIII can be delivered, using delivery means such as retroviral vectors. This method consists of incorporation of factor VIII cDNA into human cells that are transplanted directly into a factor VIII deficient patient or that are placed in an implantable device, permeable to the factor VIII molecules but impermeable to cells, that is then transplanted. A specific method can include retroviral-mediated gene transfer. In this method, an exogenous gene (e.g., a factor VIII cDNA) is cloned into the genome of a modified retrovirus. The gene/cDNA is inserted into the genome of the host cell by viral machinery where it will be expressed by the cell. The retroviral vector is modified so that it will not produce virus, preventing viral infection of the host. The general principles for this type of therapy are known to those skilled in the art and have been reviewed in the literature (e.g., Kohn, D. B., and P. W. Kantoff, *Transfusion* 29:812–820 (1989)).

Thus, for example, cells from a patient may be engineered with a polynucleotide, such as a DNA or RNA, encoding a polypeptide ex vivo, and the engineered cells then can be provided to a patient to be treated with the polypeptide. For example, cells may be engineered ex vivo by the use of a retroviral plasmid vector containing RNA encoding a polypeptide of the present invention. Such methods are well-known in the art and their use in the present invention will be apparent from the teachings herein.

Similarly, cells may be engineered in vivo for expression of a polypeptide in vivo by procedures known in the art. For example, a polynucleotide of the invention may be engineered for expression in a replication defective retroviral vector, as discussed above. The retroviral expression construct then may be isolated and introduced into a packaging cell is transduced with a retroviral plasmid vector containing RNA encoding a polypeptide of the present invention such that the packaging cell now produces infectious viral particles containing the gene of interest. These producer cells may be administered to a patient for engineering cells in vivo and expression of the polypeptide in vivo. These and other methods for administering a polypeptide of the present invention by such method should be apparent to those skilled in the art from the teachings of the present invention.

Retroviruses from which the retroviral plasmid vectors herein above mentioned may be derived include, but are not limited to, Moloney Murine Leukemia Virus, spleen necrosis virus, retroviruses such as Rous Sarcoma Virus, Harvey Sarcoma Virus, avian leukosis virus, gibbon ape leukemia virus, human immunodeficiency virus, adenovirus, Myeloproliferative Sarcoma Virus, and mammary tumor virus. In one embodiment, the retroviral plasmid vector is derived from Moloney Murine Leukemia Virus.

Such vectors well include one or more promoters for expressing the polypeptide. Suitable promoters which may be employed include, but are not limited to, the retroviral LTR; the SV40 promoter; and the human cytomegalovirus (CMV) promoter described in Miller et al., *Biotechniques* 7: 980–990 (1989), or any other promoter (e.g., cellular promoters such as eukaryotic cellular promoters including, but not limited to, the histone, RNA polymerase III, and β-actin promoters). Other viral promoters which may be employed include, but are not limited to, adenovirus promoters, thymidine kinase (TK) promoters, and B19 parvovirus promoters. The selection of a suitable promoter will be apparent to those skilled in the art from the teachings contained herein.

The retroviral plasmid vector is employed to transduce packaging cell lines to form producer cell lines. Examples of packaging cells which may be transfected include, but are not limited to, the PE501, PA317, Y-2, Y-AM, PA12, T19-14X, VT-19-17-H2, YCRE, YCRIP, GP+E-86, GP+envAm12, and DAN cell lines as described in Miller, A., *Human Gene Therapy* 1:5–14 (1990). The vector may be transduced into the packaging cells through any means known in the art. Such means include, but are not limited to, electroporation, the use of liposomes, and $CaPO_4$ precipitation. In one alternative, the retroviral plasmid vector may be encapsulated into a liposome, or coupled to a lipid, and then administered to a host.

The producer cell line will generate infectious retroviral vector particles, which include the polynucleotide(s) encoding the polypeptides. Such retroviral vector particles then may be employed to transduce eukaryotic cells, either in vitro or in vivo. The transduced eukaryotic cells will express the polynucleotide(s) encoding the polypeptide. Eukaryotic cells which may be transduced include, but are not limited to, embryonic stem cells, embryonic carcinoma cells, as well as hematopoietic stem cells, hepatocytes, fibroblasts, myoblasts, keratinocytes, endothelial cells, and bronchial epithelial cells.

The following examples are illustrative only and are not intended to limit the scope of the invention as defined by the appended claims. It will be apparent to those skilled in the art that various modifications and variations can be made in the methods of the present invention without departing from the spirit and scope of the invention. Thus, it is intended that the present invention cover the modifications and variations of this invention provided they come within the scope of the appended claims and their equivalents.

All patents, publications and publicly available sequences referred to herein are expressly incorporated by reference.

EXAMPLES

Example 1

Hemophilia A is treated by repeated infusions of plasma-derived or recombinant factor VIII products. As indicated above, rapid clearance of infused factor VIII represents a serious problem of this therapy making it extremely costly. Our finding that factor VIII clearance is mediated by low-density lipoprotein receptor-related protein (LRP) suggested that disruption of factor VIII interaction with LRP by mutagenesis may reduce clearance rates of factor VIII.

It has been established that regulation of plasma levels of a coagulation factor VIII (FVIII) and its clearance are mediated by low-density lipoprotein receptor-related protein (LRP) (Saenko et al., *J. Biol. Chem* 274:37685–92 (1999); Bovenschen et al., *Blood* 101:3933–9 (2003)), a hepatic clearance receptor with broad ligand specificity. It has been previously described that the major FVIII binding site for LRP is located within the A2 domain region 484–509 (Saenko, E. L., et al., *J. Biol. Chem.* 274:37685–37692 (1999)). To identify residues critical for FVIII binding to LRP, alanine-scanning mutagenesis of the region 484–509, which are located on the surface of the A2 domain according to the 3D-model of FVIII (Stoilova-McPhie et al., *Blood* 99: 1215–23 (2002)) and residues spatially close to this region was conducted. Mutants were generated predominantly targeting positively charged residues, as they were shown to be major contributors to the binding to LRP for a number of its ligands. In the experiments, the isolated A2 domain as a model of FVIII was used and twenty A2 mutants carrying Ala mutations at positions $Lys^{376}$, $Lys^{377}$, $His^{378}$, $Lys^{380}$, $Lys^{466}$, $Arg^{471}$, $Arg^{484}$, $Tyr^{487}$, $Ser^{488}$, $Arg^{489}$, $Arg^{490}$, $Leu^{491}$, $Lys^{493}$, $Lys^{496}$, $His^{497}$, $Lys^{499}$, $Lys^{510}$, $Lys^{512}$, $Lys^{523}$, and $Lys^{556}$ were generated. The list of generated mutations, both amino acid and DNA changes, is illustrated in Table 1.

TABLE 1

A2 Mutants

| Mutant number | Introduced Mutation | Corresponding Coding Region |
|---|---|---|
| Lys-376 | Ala | GCC |
| Lys-377 | Ala | GCC |
| His-378 | Ala | GCT |
| Lys-380 | Ala | GCT |
| Lys-466 | Ala | GCC |
| Arg-471 | Ala | GCT |
| Arg-484 | Ala | GCC |
| Tyr-487 | Ala | GCC |
| Ser-488 | Ala | GCC |
| Arg-489 | Ala | GCC |
| Arg-490 | Ala | GCC |
| Leu-491 | Ala | GCT |
| Lys-493 | Ala | GCT |
| Lys-496 | Ala | GCC |
| His-497 | Ala | GCC |
| His-499 | Ala | GCC |
| Lys-510 | Ala | GCC |
| Lys-512 | Ala | GCA |
| Lys-523 | Ala | GCC |
| Lys-556 | Ala | GCC |

The A2 mutants were expressed in baculovirus system, purified and tested for binding to LRP in a surface plasmon resonance-based assay. The methods are detailed below.

Figure 23:
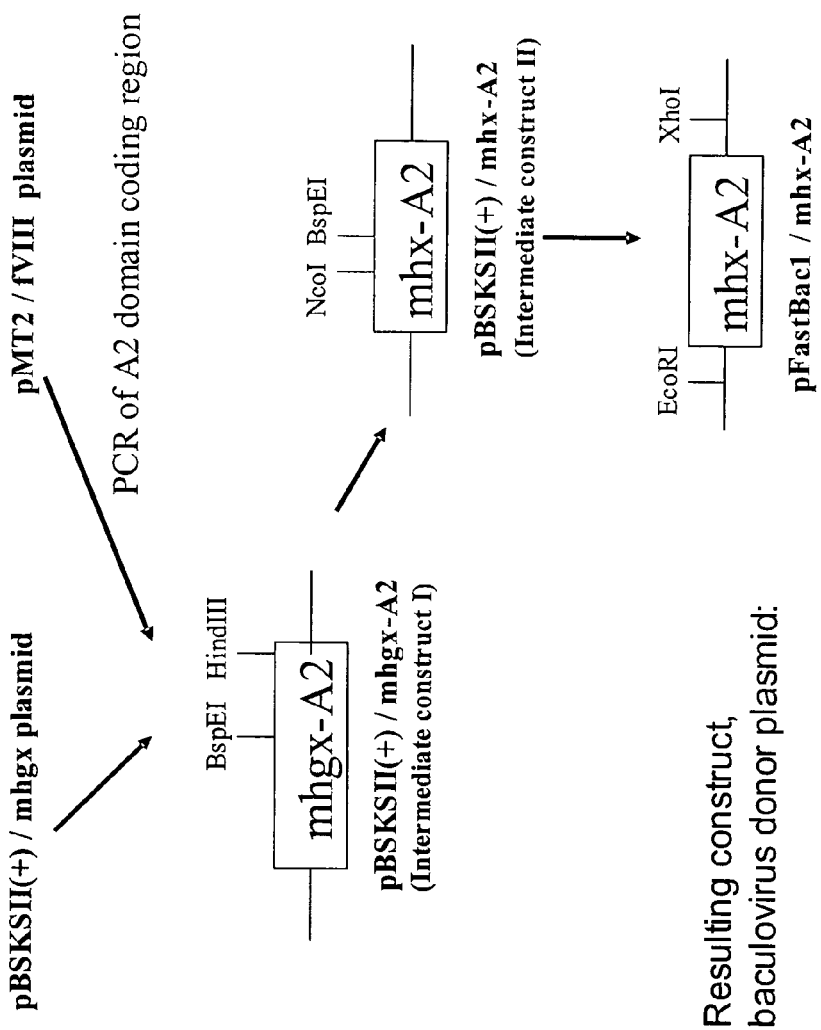
FIG. 23 illustrates the cloning of a factor VIII A2 subunit in a baculovirus vector in accordance with Example 1.

Preparation of A2 construct and mutagenesis of A2 domain. The fragment encoding wild type (wt) A2 was generated from source plasmid pMT2/fVIII (Moussalli et al., *J. Biol. Chem.* 274:32539–32542 (1999); Gilbert et al., *J. Biol. Chem.* 277:6374–6381 (2002); Cunningham et al., *J. Thromb. Haemost.* 1:2360–2367 (2003)) by PCR using oligonucleotides 5'-AACGAAGTCCGGAGCCAAGAAG-CATCCTAAAACTTGGGTAC (SEQ ID NO:6) and 5'-ACGCATCAAGCTTCTATCTTGGTTCAATGG-CAT-TGTTTTTACTCAG (SEQ ID NO:7), introducing BspEI and Hind III sites at the termini (and mutating Val-375 to Gly). Using these sites the fragment was cloned into pBSKSII(+) vector based MHGX plasmid (Katagiri, Y., and Ingham, K. C., *Biotechniques* 33:24–26 (2002)) downstream the region encoding honeybee melittin secretion signal (m), 6×His tag sequence (h), enhanced green fluorescent protein region (EGFP, g) and FXa cleavage site (x), (mhgx-A2 construct). Subsequently, we obtained a derivative construct, mhx-A2, lacking the EGFP portion, to increase secretion efficiency of the recombinant protein. This was achieved by excision of the NcoI/BspEI EGFP-coding fragment (and fXa cleavage site) followed by recloning instead a nucleotide adaptor, generated by annealing oligonucleotides 5'-CATGGGCGCCTCCATCGAGGGTCGGT (SEQ ID NO:8) and 5'-CCGGACCGACCCTCGATGGAGGCGCC (SEQ ID NO:9), thus recovering the fXa cleavage site. The cassette was subcloned into vector pFastBac1 (Invitrogen) using EcoRI and XhoI sites followed by expression of wt-A2 protein in insect Sf9 cells as described below. The scheme of cloning is illustrated in FIG. 23.

Site-specific mutagenesis of the A2 domain was performed by PCR using QuickChange MultiSite-Directed Mutagenesis Kit (Stratagene), pFastBac1/mhx-A2 plasmid as template and corresponding primers introducing a selected amino acid substitution into the coding region of A2. The generated mutants were sequenced through the whole A2 coding region to ensure its proper translation.

Expression of A2 mutants in insect cells. Wild-type and mutant A2 domains were expressed in insect Sf9 cells using Bac-to-Bac technology (Invitrogen). This expression system is ideal for primary screening of A2 mutations because it offers simplicity of technical experimentation characteristic for bacterial expression systems and provides proper post-translational modifications of human proteins similar to expression system in mammalian cells. The pFastBacI/mhx-A2 plasmid was transfected into *E. coli* DH10 Bac cells (Invitrogen), where the region encoding mhx-A2 was site-specifically transposed into the baculovirus shuttle vector pMON14272 (bacmid) residing in the DH10 Bac cells (Invitrogen). The recombinant bacmid DNA was isolated from positive clones after antibiotic/color test selection and PCR-analysis for the insert, and subsequently transfected into Sf9 cells. Cells were cultured in HyQ SFX-Insect Medium (Hyclone) supplemented with 10% Fetal Bovine Serum (Hyclone). Virus propagation in the cell supernatants was monitored by comparison with control Sf9 cells transfected with mhgx-A2 cassette containing the EGFP insert. Acceptable virus titer was indicated by the presence of 80–90% of EGFP-positive cells in the control culture, which occurred on average on the $4^{th}$ day following transfection. This approach (comparison with EGFP control and optimization of culture medium) allowed for the rapid accumulation of virus at high titers (up to $10^{11}$ pfu/ml) as well as for the determination of the optimal time for the collection of cell supernatants.

Quantitative production of A2 mutants. The cell supernatants collected as described above were used to infect Sf9 cells for large-scale production of the hx-A2 protein.

The conventional technique used for production of quantitative amounts of recombinant proteins in baculovirus system is based on determination of the optimal virus particle/cell ratio, or multiplicity of infection (MOI). An alternative approach was developed for the determination of the optimal volumes of viral stocks to be used for the infection of a known number of cells (Sarafanov & Saenko; *Anal. Biochem.* 328:98–100 (2004)). This approach employs the comparative titering of baculovirus stocks for expression efficiency using a mini-format of multi-well plates and allows processing large sets of viral stocks in a fast and easy way, and is described in detail below. The culture media from infected Sf9 cells (at a density of $1.5 \times 10^6$ cells/ml) were collected at the peak of secretion of A2 mutants into the medium ($4^{th}$ day). For large-scale production, Sf9 cells were cultured in HyQ SFX-Insect Medium (Hyclone), which yielded higher expression levels of mutant A2 proteins in comparison with Sf-900 II SFM (Invitrogen). At this step, serum was omitted from culture medium.

Detailed discussion regarding quantitative production of A2 mutants. As discussed above, we expressed a set of 20 single-point mutants of the A2 domain of human coagulation factor VIII. We used the Bac-to-Bac baculovirus expression system (Invitrogen, Carlsbad, Calif.), which allows for obtaining recombinant virus that are not mixed with the parental wild-type form. Non-mutated A2 domain was expressed and used to test the expression system and to obtain a reference protein for comparison with the mutant proteins. Using the A2 cDNA and MHGX vector as described above we assembled an expression cassette coding polypeptide mhx-A2, which bears melittin secretion signal (m), 6×His Tag (h) and factor Xa cleavage site (x), and is secreted in the hx-A2 form. This cassette was subcloned into pFastBac1 vector and expressed in Sf9 cells as described above. The expressed recombinant A2 domain was compared to plasma-derived A2 prepared from thrombin-activated fVIII by chromatography on Mono S column (Fay et al., *J. Biol. Chem.* 266:8957–8962 (1991); Lapan et al., *J.*

*Biol. Chem.* 272:2082–2088 (1997)). Functional activity of the recombinant A2 was confirmed in a coagulation assay (Koszelak et al., *J. Biol. Chem.* 275:27137–27144 (2000) and its structural integrity was confirmed in a binding assay with fVIII ligands. Recombinant A2 and plasma-derived A2 showed similar affinities to low density lipoprotein receptor-related protein (Saenko et al., *J. Biol. Chem.* 274:37685–37692 (1999)) and heparin used as a model of heparan sulphate proteoglycans (Sarafanov et al., *J. Biol. Chem.* 276:11970–11979 (2001).

Next, the FastBac1/mhx-A2 plasmid was used as template for alanine-scanning mutagenesis of A2, followed by transfection of the cassettes into Sf9 cells. As discussed above, the cells were incubated for 4 days ensuring a high accumulation of virus in supernatants. The presence of the mutant proteins in cell supernatants was confirmed by PAGE-Western blot. Virus titers of $10^{9-10^{11}}$ pfu/m were determined by the viral plaque assay. The values varied significantly in three assays because of the sensitivity of the assay to experimental conditions.

A conventional technique used for production of quantitative amounts of recombinant proteins in baculovirus system is based on determination of the optimal virus particle/cell ratio, or multiplicity of infection (MOI). The titer of virus is determined in the viral plaque assay (Payment P. and Trudel M., *Methods and techniques in virology: isolation and identification of viruses*, Dekker Publishing, New York, N.Y., p. 32–34 (1993)), in which Sf9 cells on dishes are treated with aliquots of serially diluted viral stock, followed by incubation of the cells in solidified medium for 5–10 days until the plaques develop for the calculation of viral titer. The optimal MOI is next determined by testing various MOI in shaker culture and monitoring the expression levels for 2–5 days. This method allows for the processing of only a limited number of viral stocks and takes on average 15 or more days.

In terms of practice, determination of optimal MOI actually means finding an optimal (effective) stock volume per certain amount of host cells. This volume can be determined by direct testing expression from the stock. Initially, the detection of expressed proteins was used to assess the virus titers, as applications of the end-point dilution method (Payment P. and Trudel M., *Methods and techniques in virology: isolation and identification of viruses*, Dekker Publishing, New York, N.Y., p. 32–34 (1993)). The stocks were serially diluted until the absence of virus, resulting in the inability to promote expression in Sf9 cells (Richardson C. D., Methods in Molecular Biology vol. 39, Humana Press Inc., Totowa, N.J., Grosse, F., and Manns, A., p. 179–185 (1995); Cha, H. J. et al., *Biotechniques* 23:782–786 (1997)).

As a further development, some researchers measure levels of such expression on dishes, thus, titering the stock for expression efficiency. However, the effective volume of the stock must be specified in the subsequent shaker culture experiment, because the kinetics of expression is different for suspension and adherent cultures.

In large-scale production of mhx-A2 proteins, we developed an alternative approach for determination of the optimal volumes for infection. This approach employs the comparative titering of baculovirus stocks for expression efficiency using mini-format of multi-well plates and allows processing large sets of viral stocks in a fast and easy way (Sarafanov & Saenko; *Anal. Biochem.* 328:98–100 (2004)).

At the first step, the stocks are characterized in terms of relative efficiency of expression versus a control stock. Using a multi-well format, which provides fast and uniform handling, the stocks are serially diluted and tested for expression, followed by determination of differences in the optimal dilutions (corresponding to maximal expression) versus the control stock. At the second step, the effective (optimal) volume is specified only for the control stock in a simple shaker culture experiment. This allows calculating such volumes for all other stocks, and proceeding to the large-scale expression of all proteins. We tested this approach in the following experiments.

At the first step, the viral stocks were serially five-fold diluted using 96-well polyethylene plates (typically, 10 stocks per plate), thus, making 2D-like arrays of the samples. By transferring aliquots, each array was replicated to a 96-well plate with adherent Sf9 cells, seeded at 50% confluence. The plates were incubated at 28° C., and the medium was analyzed for levels of the expressed proteins on the day 3, 4 and 5 as follows. Each expression array was replicated through several 96-well polyethylene plates with PBS pH 7.2/0.05% Tween-20/1% BSA to make plates corresponding to each number of the medium dilution (1:20, 1:100, and 1:500). Each medium dilution array was next replicated to 96-well Ni-NTA-H is Sorb plate for ELISA (Qiagen, Valencia, Calif.), capturing the expressed proteins via the His-Tags, followed by the detection using anti-A2 antibodies. As a control, we used the viral stock for non-mutated hx-A2 and finally obtained expression profiles for all stocks.

Along the time of incubation, the expression peaks were shifting towards higher dilution and increasing their height, similarly to that described previously (Liebman, J. M. et al., *Biotechniques* 26:36–42 (1999)). The maximal levels of expression varied considerably, obviously due to effects of corresponding mutations. The five-fold increment of stock dilution was sufficient to determine the optimal dilutions, which would promote the highest expression. At the same time, we point out that for poorly expressed proteins this increment can be decreased two to three-fold. Next, we determined relative differences in the optimal dilution of each stock versus the control stock. These differences (expression indices, $k_i$) were calculated as ratios between numbers of optimal dilutions of the control stock ($N_c$) and of any given stock ($N_i$), $k_i=N_c/N_i$. The higher the $k_i$, the lower expression efficiency of the given stock (i), and thus, the efficient volume of this stock is k times larger than that of the control stock. Practically, these indices can be easily determined from the printouts of ELISA readings as differences between the corresponding absorbance maximums. Notably, the relative values of expression indices are quite reproducible, even though the conditions of culturing vary. We repeated the above experiment using different density of Sf9 cells and volumes of medium taken per well, and found that even though the expression profiles shifted, the indices values were essentially same. Thus, the use of relative units for characterizing stocks is much more accurate than the use of absolute values (i.e., virus titers or the effective volumes determined directly) which are not reproduced well.

At the second step, in 125-ml Erlenmeyer flasks we set seven cultures, each with 30 ml of $1.5 \times 10^6$ Sf9 cells/ml, infected with 200 μl aliquots from five-fold serial dilutions of the control stock. The cultures were incubated in an orbital shaker at 100 rpm and at 28° C., and the expression profiles were tested on day 3, 4 and 5 of incubation. The level of expressed hx-A2 was found to be maximal at the stock dilution of 1:15625 on day 4, allowing determination of the effective volume for the control stock. Based on this value and on the obtained expression indices, we next calculated the optimal volumes for all other viral stocks. In additional experiment with suspension mini-cultures we confirmed that these volumes indeed corresponded to the highest levels of expression. Finally, we performed the large-scale expression of all proteins, infecting 120 ml of the cells by calculated volumes of the stocks in 500-ml flasks. The expression levels of the proteins were in the range of 0.1–20 µg/ml and proportional to the highest levels of expression determined in the titering experiment, which additionally confirms the correctness of approach. The proteins were purified from the media and used in functional assays.

This method can be used in a broad range of applications. In case of non-secreted proteins, the expression can be analyzed by preparing cell lysates directly in the expression plates. In case the expressed proteins possess enzymatic activity, they can be quantitated in a corresponding assay using the same multi-well format. The method can be further simplified by starting the shaker culture experiment (for the control stock) prior to the stocks titering experiment. For proteins having similar kinetics of expression, the described approach will allow determining the optimal time of incubation at once. In case when the expressed proteins show different kinetics of expression in the titration assay, at the next step, the stocks should be grouped according to the differences in the incubation times; and the groups should be processed independently. Finally, an average set of 10–30 (and more) viral stocks can be easily processed in 8–10 days. Most importantly, using this technique 20 viral stocks can be processed with at least 10 times less effort than using the common technique. For very large sets of stocks, the titering experiment can be automatized using robotic stations. Applying the same technology, the proteins can be further expressed in multi-well plates and obtained as mini-preps, similarly to that described recently (Garzia L. et al., *Biotechniques* 35:384–91 (2003)).

Purification of rA2 domain mutants. Recombinant wt-A2 and mutant A2 domains were purified from cell culture media by affinity chromatography on a Sepharose column with immobilized monoclonal anti-A2 antibody 8860 (Saenko and Scandella, *J. Biol. Chem.* 270:13826–13833 (1995)). For each mutant, bound protein was eluted with 50% ethylene glycol and transferred into 20 mM HEPES, pH 7.4, containing 150 mM NaCl, 2 mM $CaCl_2$ and 0.005% Tween 20 by running through a prepacked NAP-5 column (Amersham, Pharmacia, UK).

Surface plasmon resonance-based binding assay. The kinetics of interaction of recombinant A2 mutants with LRP was determined using a BIAcore 3000 biosensor system (Biacore, Sweden). This system allows real-time biomolecular interaction analysis (BIA) using surface plasmon resonance (SPR) technology. One molecule (the ligand) is usually immobilized on the surface of the sensor chip; the second molecule (the analyte) in solution is passed over the chip under conditions of continuous flow, and the amount of the bound analyte is detected by the system. SPR is a non-invasive optical measuring technique which measures the mass concentration of biomolecules in close proximity to the sensor chip where association and dissociation of biomolecular complexes occurs. Association and dissociation of recombinant A2 mutants was assessed in 20 mM HEPES, pH 7.4, containing 150 mM NaCl, 2 mM $CaCl_2$, 0.005% Tween-20 at a flow rate of 20 µl per min at 25° C. The association ($k_{on}$) and dissociation ($k_{off}$) rate constants were determined using BIAevaluation Version 3.1 software. The data were corrected for bulk refraction index changes and fitted to a one-site binding model by a non-linear regression analysis. Equilibrium dissociation constants ($K_D$) were calculated from the ratio $k_{off}/k_{on}$.

Determination of activity of reconstituted FVIIIA. FVIIIa heterotrimer was reconstituted from recombinant A2 mutants and plasma-derived A1/A3-A2-C1 heterodimer. The A1/A3-C1-C2 heterodimer was prepared from thrombin activated fVIII by chromatography on Mono S column as described (Fay et al., *J. Biol. Chem.* 266:8957–8962 (1991); Lapan et al., *J. Biol. Chem.* 272:2082–2088 (1997)). Activity of reconstituted FVIIIa molecules was detected in a one-stage clotting assay using FVIII deficient plasma (George King Biomedical, Inc.) and ATTP reagent (DiaPharma). The assay was performed using MLA ELECTRA 800 automatic coagulation timer in accordance with Manufacturer's recommendations (Medical Laboratory Automation).

Results. The generated A2 mutants were tested for binding to LRP in a surface plasmon resonance-based assay using BIAcore 3000 biosensor system (Biacore, Sweden) as described above. The results are presented in Table 2.

TABLE 2

Expression levels, affinities to LRP and reconstituted activities of r-A2 mutants

| Mutant number | Expression level in cell culture medium (µg/ml) | Affinity to LRP (KD, nM) | Activity of reconstituted FVIIIa (% of wt activity) |
|---|---|---|---|
| 1. wild type | 2.4 | 21 | 100 |
| 2. #1(Lys-376) | 1.8 | 25.5 | 73.9 |
| 3. #2(Lys-377) | 2.2 | 18 | 364.9 |
| 4. #3(His-378) | 2.25 | 19 | 417.0 |
| 5. #4(Lys-380) | 2 | 47 | 290.9 |
| 6. #5(Lys-466) | 0.42 | 600 | 129.8 |
| 7. #6(Arg-471) | 0.09 | 400 | 34.6 |
| 8. #7(Arg-484) | 2.7 | 320 | 64.9 |
| 9. #8(Tyr-487) | 2.1 | 97 | 87.9 |
| 10. #9(Ser-488) | 2.4 | 67 | 231.7 |
| 11. #10(Arg-489) | 3.3 | 150 | 130.4 |
| 12. #11(Arg-490) | 3.5 | 59 | 151.3 |
| 13. #12(Leu-491) | 2.45 | 21 | 518.4 |
| 14. #13(Lys-493) | 3.42 | 18 | 266.7 |
| 15. #14(Lys-496) | 4.2 | 9.5 | 262.9 |
| 16. #15(His-497) | 1.8 | 51 | 242.0 |
| 17. #16(His-499) | 1.9 | 33 | 128.0 |
| 18. #17(Lys-510) | 1.9 | 29 | 91.5 |
| 19. #18(Lys-512) | 2.1 | 21 | 218.8 |
| 20. #19(Lys-523) | 2.4 | 41 | 389.8 |
| 21. #20(Lys-556) | 2.2 | 33 | 196.5 |

As illustrated by Table 2, recombinant wt-A2 showed affinity for LRP (Kd=21 nM) similar to that reported for plasma-derived A2 (Kd=15 nM, Bovenschen et al., *J. Thromb. Haemost.* 1(*Suppl* 1): 7–12 (2003)), thus confirming its structural integrity as a reference protein. The affinities of Ala mutants at positions 466, 471, 484, 487 and 489 were dramatically decreased by 28, 19, 15, 5, and 7-fold, respectively. The affinities of the Ala mutants at positions 380, 488, 490, 497, 499, 523 and 556 were moderately decreased by 1.5–3-fold.

The A2 domain represents one of the components of activated FVIII (heterotrimer A1/A2/A3-C1-C2), which possesses the cofactor activity. To assess the effect of introduced A2 mutations on the activity of FVIIIa, we reconstituted FVIIIa molecules from each A2 mutant and plasma-derived heterodimer A1/A3-C1-C2 and tested their cofactor activities in a one-stage clotting assay. In other words, to evaluate whether introduction of the above mutations in factor VIII would impair its cofactor activity, the A2 mutants were tested in a one-stage clotting assay for their ability to reconstitute with purified A1/A3-A2-C1 dimer into functionally active fVIII heterodimer (A1/A2/A3-C1-C2).

As illustrated by Table 2, the activities of all reconstituted chimeric FVIIIa molecules, except that containing the Arg471Ala mutation, were similar or even higher than the activity of FVIIIa reconstituted with the wt-A2 domain. The decreased activity of the Arg471Ala mutant is consistent with the observation that an Arg471Gly natural mutation is associated with mild Hemophilia A.

Accordingly, based on the data, the identified mutations discussed above prolong factor VIII half-life in plasma and/or have an increased specific activity.

Example 2

We have shown that in a cell culture and in vivo fVIII is catabolized from its complex with vWf and this process is mediated by low-density lipoprotein receptor-related protein (LRP) (Examples 3–5; Saenko, E. L., et al., *J. Biol. Chem.* 274:37685–37692 (1999)). LRP, a member of the low density lipoprotein (LDL) receptor family (Neels, J. G., et al., *Fibrinol. Proteol.* 12:219–240 (1998)), is responsible for plasma clearance of lipoprotein remnants, serine proteinases and their complexes with inhibitors (serpins) (Neels, J. G., et al., *Fibrinol. Proteol.* 12:219–240 (1998); Strickland, D. K., et al., *FASEB J.* 9:890–898 (1995)). LRP is prominent in liver on hepatocytes and in vasculature and is presented on the surface of smooth muscle cells, fibroblasts and macrophages (Moestrup, S. K., et al., *Cell Tissue Res.* 269:375–382 (1992)). In addition to fVIII, LRP mediates the clearance of a number of proteins involved in blood coagulation and fibrinolysis, such as factors IXa (Lenting, P., et al., *Blood* 94:455a (1999)) and Xa (Narita M., et al., *Blood* 91:555–560 (1998); Kamikubo, Y., et al., *Thromb. Res.* 83:161–173 (1996)), plasminogen activators and their complexes with plasminogen activator inhibitor (Warshawsky, I., et al., *Proc. Natl. Acad. Sci. U.S.A.* 9:6664–6668 (1994); Herz, J., et al., *Cell* 71:411–421 (1992); Orth, K., et al., *J. Proc. Natl. Acad. Sci. U.S.A.* 89:7422–7426 (1992)). The 39 kDa receptor-associated protein (RAP), which binds to LRP with high affinity ($K_d$=4 nM) and efficiently inhibits binding and endocytosis of all known LRP ligands, is a useful tool for studying interactions of LRP and its ligands (Williams, S. E., et al., *J. Biol. Chem.* 267:9035–9040 (1992)).

The sites of fVIII involved in interaction with LRP are located in A2 domain residues 484–509 (Saenko, E. L., et al., *J. Biol. Chem.* 274:37685–37692 (1999)) and in the C-terminal portion of the C2 domain (Lenting, P., et al., *J. Biol. Chem.* 274:23734–23739 (1999)). Since the latter region of fVIII is likely to be blocked by vWf molecule bound to the C2 domain (Lenting, P., et al., *J. Biol. Chem.* 274:23734–23739 (1999); Saenko, E. L., et al., *J. Biol. Chem.* 269:11601–11605 (1994)), the C2 site may contribute to the clearance of fVIII only in the absence of vWf. This is consistent with the reported faster clearance of fVIII in vWf deficient patients and animals (Lethagen, S., et al., *Ann. Hematol.* 65:253–259 (1992); Fijnvandraat, K., et al., *Thromb. Haemost.* 77:298–302 (1997); Over, J., et al., *J. Clin. Invest.* 62:223–234 (1978)), which has been shown to be mediated by LRP (Shwarz, H. P., et al., *Blood* 95:1703–1708 (2000)).

For many proteins, LRP-mediated endocytosis is facilitated by cell-surface heparan sulfate proteoglycans (HSPGs), one of the components constituting the extracellular matrix. It is currently believed that one of the general functions of cell surface HSPGs is to provide initial binding of proteins to cells, thus increasing the rates at which the proteins interact with their specific receptors (Lander, A. D., *Matrix Biology* 17:465–472 (1998)). Among the ligands of LRP that bind the HSPGs are lipoprotein lipase (Chappell, D. A., et al., *J. Biol. Chem.* 268:14168–14175 (1993)), apoE-containing lipoproteins (Ji, Z. S., et al., *J. Biol. Chem.* 269:2764–2772 (1994); Mahley, R. W. and Ji, Z. S., *J. Lipid. Res.* 40:1–16 (1999)), thrombospondin (Mikhailenko, L., et al., *J. Biol. Chem.* 270:9543–9549 (1995)), thrombin-protease nexin 1 complex (Knauer, M. F., et al., *J. Biol. Chem.* 274:275–281 (1999)) and tissue factor pathway inhibitor (TFPI) (Warshawsky, I., et al., *Proc. Natl. Acad. Sci. U.S.A.* 91:6664–6668 (1994); Warshawsky, I., et al., *J. Biol. Chem.* 271:25873–25879 (1996)). For some of these ligands, HSPGs serve as co-receptors of LRP and provide the initial cell surface binding and subsequent presentation to LRP (Strickland, D. K., et al., *FASEB J.* 9:890–898 (1995); Mahley, R. W. and Ji, Z. S., *J. Lipid. Res.* 40:1–16 (1999)). For other ligands, HSPGs function themselves as catabolic receptors acting independently of LRP (Mikaelsson, M., et al., *Thromb. Haemost.* 69:1210 (1993)). Noteworthy, all LRP ligands that interact with HSPGs are also able to bind heparin (Crisp, R. J., et al., *J. Biol. Chem.* 275:19628–19637 (2000)), which is structurally similar to carbohydrate portions of HSPG molecules.

The reported $K_d$ for the fVIII interaction with LRP (116 nM (Saenko, E. L., et al., *J. Biol. Chem.* 274:37685–37692 (1999))) is much higher than the normal concentration of fVIII in plasma (~1 nM (Wion, K., et al., *Nature* 317:726–730 (1985))), indicating that the direct binding of plasma fVIII/vWf complex to LRP is negligible and that other receptors may be involved in this process. In this example, we studied the participation of cell surface HSPGs in the binding and catabolism of fVIII/vWf complex, based on the ability of fVIII to interact with heparin (Barrow, R. T., et al., *J. Biol. Chem.* 269:593–598 (1994)). We demonstrated that HSPGs are indeed responsible for the initial binding of fVIII/vWf complex to the surface of various LRP-expressing cells and facilitate fVIII catabolism both in cell culture and in vivo. We showed that the binding occurs via the fVIII moiety of the fVIII/vWf complex and we localized the major heparin-binding site of fVIII to its A2 domain.

Experimental Procedures

Reagents. Heparin (average molecular weight 17–19 kDa) and biotinylated heparin were purchased from Sigma and Celsus Laboratories Inc., respectively. Human coagulation factors IXa, X and Xa (Enzyme Research Laboratories) and heparinase I (Sigma) were obtained from the indicated vendors. Active site fluorescently-labeled factor IXa (F1-FFR-fIXa) was obtained from Dr. Philip Fay. Anti-A2 mAb 8860 was provided by Baxter/Hyland Healthcare Inc. The rabbit polyclonal anti-LRP antibody Rab 2629 was provided by Dr. Dudley Strickland. Phosphatidylserine (PS) and phosphatidylcholine (PC) were obtained from Sigma. Phospholipid vesicles containing 25% PS and 75% PC were prepared as previously described (Barenholz, Y., et al., *Biochemistry* 16:2806–2810 (1977)). The synthetic peptides were synthesized using a 9050 Milligen synthesizer (Millipore) by 9-fluorenmethoxycarbonyl method and pentafluoro ester activation chemistry and were purified by reverse phase HPLC using C18 column (Waters) in gradient of 0–70% acetonitrile in 0.1% trifluoroacetic acid. The 2.2–3.5 mM solutions of peptides were dialyzed versus 20 mM HEPES pH 7.4, 0.15 M NaCl (HBS) using membrane with 1 kDa cut-off (Pierce).

Proteins. FVIII was purified from therapeutic concentrates prepared by Method M, American Red Cross (Saenko, E. L., et al., *J. Biol. Chem.* 271:27424–27431 (1996)). HCh and LCh of fVIII were prepared as described previously (Saenko, E. L. and Scandella, D., *J. Biol. Chem.* 272: 18007–18014 (1997)). The A1 and A2 subunits were obtained from thrombin activated fVIII using ion exchange chromatography on Mono S column (Amersham Pharmacia Biotech) (Saenko, E. L., et al., *J. Biol. Chem.* 274:37685–37692 (1999)).

Radiolabeling of fVIII and Its A2 Subunit. Prior to labeling, fVIII and A2 were dialyzed into 0.2 M sodium acetate, pH 6.8, containing 5 mM calcium nitrate. Five µg of fVIII in 30 µl of the above buffer were added to lactoperoxidase beads (Worthington Biochemical Corp.) containing 5 µl of Na$^{125}$I (100 mCi/ml, Amersham Pharmacia Biotech) and 5 µl of 0.03% $H_2O_2$ (Mallincrodt) and incubated for 4 min at room temperature. Unreacted Na$^{125}$I was removed by chromatography on PD10 column (Amersham Pharmacia Biotech). The specific radioactivities of $^{125}$I-labeled fVIII and A2 were 3–6 µCi/µg of protein. The activity of $^{125}$I-fVIII determined in the one-stage clotting assay (Lollar, P., et al., *Methods Enzymol.* 222:128–143 (1993)) (3650 units/mg) was similar to that of unlabeled fVIII (3840 units/mg).

Assays for Cell Mediated Surface Binding, Internalization and Degradation of Ligands. LRP-expressing mouse embryonic fibroblast cells (MEF) and mouse embryonic fibroblast cells genetically deficient in LRP biosynthesis (PEA 13) were obtained from Dr. Joachim Herz (University of Texas Southwestern Medical Center, Dallas, Tex.) and maintained as described (Willnow, T. E. and Herz, J., *J. Cell Sci.* 107:719–726 (1994)). Cells were grown to 2×10$^5$ cells/well as previously described (Saenko, E. L., et al., *J. Biol. Chem.* 274:37685–37692 (1999)). Human smooth muscle cells (SMC) (ATCC Deposit No. CRL 1999) and alveolar epithelial cells (T2) (ATCC Deposit No. CRL 2078) were obtained from the American Tissue Culture Collection, 10801 University Boulevard, Manassas, Va. 20110-2209. SMC and T2 cells were gown to the final density of 10$^5$ cells/well in DMEM and Leibovitz's L-15 mediums, respectively, containing 10% Fetal Bovine Serum (Gibco BRL). Complex of $^{125}$I-fVIII, or unlabeled fVIII with vWf was prepared by incubation of the proteins at a 1:50 ratio in HBS, 5 mM $CaCl_2$ for 30 min at 25° C. The formation of the complex was verified by gel filtration as described previously (Saenko, E. L., et al., *J. Biol. Chem.* 274:37685–37692 (1999)).

To assess the contribution of HSPGs in fVIII uptake, the cells were pre-incubated with medium containing heparinase-I (Sigma) at a concentration of 0.005 IU/ml for 30 min at 37° C. followed by washing the cells three times with HBS, 0.1% BSA. Surface binding, internalization and degradation assays were conducted as described previously (Kounnas, M. Z., et al., *J. Biol. Chem.* 270:9307–9312 (1995)). In some experiments, surface binding was determined after incubation at 4° C. to prevent endocytosis (Knauer, M. F., et al., *J. Biol. Chem.* 272:29039–29045 (1997)). Surface binding of radiolabeled ligands was defined as the amount of radioactivity released by the treatment of the cells with trypsin (50 µg/ml) and proteinase K (50 µg/ml) (Sigma) as described (Chappell, D. A., et al., *J. Biol. Chem.* 267:25764–25767 (1992)). This treatment was previously shown to release radioligands bound to the cell surface (Kounnas, M. Z., et al., *J. Biol. Chem.* 270:9307–9312 (1995)), therefore radioactivity remaining associated with the cells was considered to be internalized. Degradation was defined as radioactivity in the medium that is soluble in 10% trichloroacetic acid. The value of degradation was corrected for non-cellular mediated degradation by subtracting the amount of degradation products in parallel wells lacking cells.

Factor Xa Generation Assay. The rate of conversion of factor X to factor Xa was measured in a purified system (Lollar, P., et al., *Methods Enzymol.* 222:128–143 (1993)) in which fVIIIa was substituted by its A2 subunit as described (Fay, P. J., et al., *J. Biol. Chem.* 273:19049–19054 (1998); Fay, P. J. and Scandella, D., *J. Biol. Chem.* 274:29826–29830 (1999)). A2 subunit (200 nM) was pre-incubated for 30 min with varying concentrations of heparin (0–100 µg/ml) in HBS, 5 mM $CaCl_2$, 0.01% Tween 20 and 200 µg/ml BSA. This was followed by the addition of factor IXa (5 nM) and phosphatidyl serine phosphatidyl choline (PSPC) vesicles (10 µM) for 10 min, prior to the addition of factor X (300 nM). To determine the initial rates of factor Xa generation, aliquots were removed at 10, 20, 30 and 45 min and the reaction was stopped with 0.05 M EDTA. Factor Xa generation was determined by conversion of synthetic substrate S-2765 (Chromogenix, Sweden) as described (Fay, P. J. and Scandella, D., *J. Biol. Chem.* 274:29826–29830 (1999)).

Fluorescence Anisotropy Measurements. The measurements of interaction of fVIII A2 subunit and Fl-FFR-fIXa were performed as described (Fay, P. J. and Scandella, D., *J. Biol. Chem.* 274:29826–29830 (1999)). Prior to the experiment, A2 was incubated with heparin at varying concentrations for 15 min at 25° C. in HBS, 5 mM $CaCl_2$. The anisotropy was measured in a 0.2 ml cell upon addition of PSPC vesicles (50 µM) and Fl-FFR-fIXa (30 nM) in the presence or absence of factor X (400 nM). The measurements were carried out using SLM 8000C spectrofluorometer (SLM Instrument Inc.) at an excitation wavelength of 495 nm and an emission wavelength of 524 nm. The data were recorded 5 times for each reaction and averaged.

Kinetic Measurements Using Surface Plasmon Resonance (SPR). The kinetics of interaction of fVIII and its fragments with heparin were measured by the surface plasmon resonance (SPR) technique using Biacore 3000 (Biacore, Sweden). Biotinylated heparin was immobilized at the level of ~300 resonance units (RU) on the surface of a biosensor SA chip in HBS, 5 mM $CaCl_2$, 0.05% Tween 20. Binding of fVIII and its fragments was measured in the same buffer at a flow rate of 10 µl/min. Dissociation of the ligand was measured upon replacement of the ligand solution with buffer. The chip surface was regenerated by washing with 1 M NaCl, 0.05% Tween 20. The kinetic parameters were derived from kinetic curves using Biacore BIAevaluation 3.1 software.

Immunofluorescence Microscopy. Human hepatocellular carcinoma cells HEP G2 (ATCC Deposit No. HB 8065) (American Tissue Culture Collection, 10801 University Boulevard, Manassas, Va. 20110-2209) were gown on coverslips to 80% confluence in DMEM containing 10% FBS at 37° C., 6% $CO_2$. Intact cells or cells treated with heparinase as above, were incubated with 10 nM of fVIII/vWf complex in 0.5 ml DMEM, 1% BSA for 2 h at 4° C. The cells were washed twice with phosphate-buffered saline (PBS), fixed in PBS containing 2% formaldehyde for 15 min at room temperature, and stained for fVIII, LRP and HSPGs by triple-label immunofluorescence staining.

Staining for fVIII was performed by sequential incubations with mouse anti-fVIII mAb 8860 (epitope within A2 subunit), biotinylated anti-mouse antibody and Texas Red-conjugated Avidin D (2.5 µg/ml). Staining for LRP was performed by sequential incubations with rabbit polyclonal anti-LRP antibody Rab 2629, biotinylated anti-rabbit IgG and Fluorescein Avidin DCS (2.5 µg/ml). Staining for HSPGs was performed by sequential incubations with mouse monoclonal anti-heparan sulfate antibody 10E4

(Seikagaku Corporation), biotinylated anti-mouse IgG and AMCA Avidin D (5 µg/ml). The primary antibodies were added at 5 µg/ml and incubated with the cell samples for 1 h at 25° C. The secondary biotinylated antibodies and fluorescent reagents were purchased from Vector, Inc. and used according to the supplied protocols. Avidin/Biotin blocking kit (Vector) was applied after staining with each fluorescent probe. The specificity of the staining was determined in control experiments using normal mouse or rabbit immunoglobulins, instead of the primary antibodies.

For microscopy, the coverslips with triple-stained cells were mounted on slides with ProLong Antifade mounting medium (Molecular Probes, Inc.). The images were obtained using Eclipse E800 microscope (Nikon) equipped with a set of selective fluorescent filter blocks and digital SPOT RT camera (Diagnostic Instruments, Inc.). Simultaneous visualization of fVIII, LRP and HPGs was performed by merging the single-dye images using SPOT Advanced Program Mode.

Clearance of $^{125}$I-fVIII/vWf Complex in Mice. Prior to the experiment, $^{125}$I-fVIII, vWf, and RAP were dialyzed in HBS, 5 mM CaCl$_2$ buffer. BALB/c mice (12–14 weeks old, weight 20–24 g) were injected in the tail vein with 100 µl of either 0.2 mM protamine or 150 µM RAP alone or with 100 µl of 0.2 mM protamine and 150 µM RAP together in the above buffer. After 2 min interval, 100 µl samples of $^{125}$I-fVIII/vWf complex formed from $^{125}$I-fVIII (15 nM) and vWf (750 nM) were injected into mice. In control experiment, $^{125}$I-fVIII/vWf complex was injected in the absence of protamine and RAP. Blood samples of 35–40 µl were withdrawn from each mouse via retroorbital puncture into 15 µl of 0.1 M sodium citrate buffer, pH 7.4, at selected time intervals (1, 5, 10, 15, 30, 60, 120, 240, 360 and 480 min). The radioactivity of the samples was measured and normalized for the blood volumes withdrawn. The percentage of $^{125}$I-fVIII remaining in circulation was calculated assuming the radioactivity of the aliquot taken at 1 min after injection as 100%. The time course of each of the above conditions was examined in four mice and averaged. The kinetics of $^{125}$I-fVIII clearance from circulation was fitted using Sigmaplot 3.0 computer program (Jandel Scientific) to a previously used double-exponential model (Saenko, E. L., et al., *J. Biol. Chem.* 274:37685–37692 (1999)) as described in the text.

Results

Figure 1B:
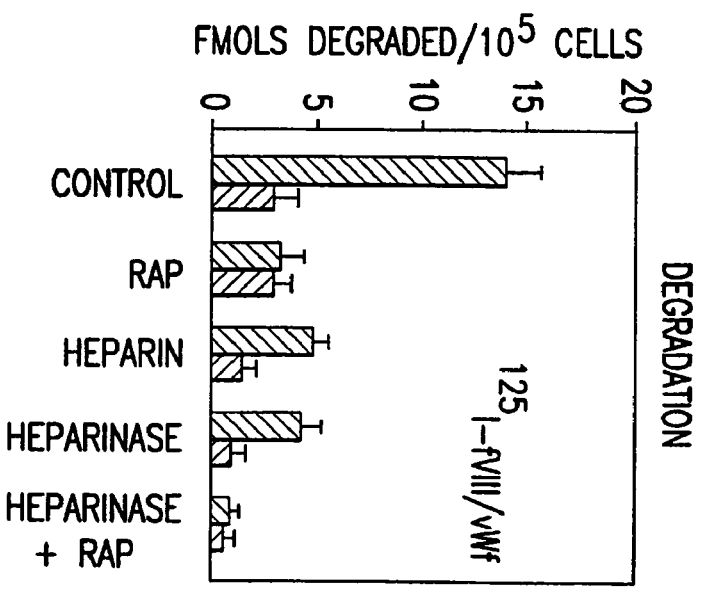

HSPGs are the primary receptors responsible for initial binding of fVHIII/vWf complex to LRP-expressing cells. We previously demonstrated that RAP inhibited endocytosis and degradation of fVIII from its complex with vWf by LRP-expressing cells, indicating that LRP is involved in the catabolism of fVIII (Saenko, E. L., et al., *J. Biol. Chem.* 274:37685–37692 (1999)). To elucidate whether LRP participates in the initial binding of $^{125}$I-fVIII/vWf complex to the cell surface, we tested whether this binding is inhibited by RAP. As seen from FIG. 1A, the presence of RAP did not significantly reduce the surface binding of $^{125}$I-fVIII/vWf complex, suggesting that the complex binds to the cell surface not via LRP, but via some other receptor(s). We next examined whether HSPGs are responsible for the initial binding of fVIII/vWf complex by testing the effect of heparin or heparinase, which are known to inhibit the interaction of HSPGs with their ligands. As seen from FIG. 1A, both agents significantly reduced the cell surface binding, indicating that HSPGs are the major surface receptors responsible for the initial binding of fVIII/vWf complex to cells. Consistent with a role for HSPGs in the surface binding of fVIII/vWf, degradation of fVIII was reduced by heparinase treatment of the cells almost to the same degree as by addition of RAP to untreated cells (FIG. 1B). Addition of RAP to heparinase-treated cells inhibited degradation by >95%, showing that LRP and HSPGs are synergistically involved in fVIII catabolism in this cell model.

Noteworthy, LRP-deficient PEA13 cells also degraded fVIII at ~25% the level of LRP-expressing cells (FIG. 1B), indicating existence of an alternative pathway of fVIII catabolism that is not mediated by LRP. Since this pathway was significantly inhibited by heparin or heparinase (FIG. 1B), HSPGs are required not only for LRP-mediated, but also for an LRP-independent pathway of fVIII degradation.

Figure 1C:
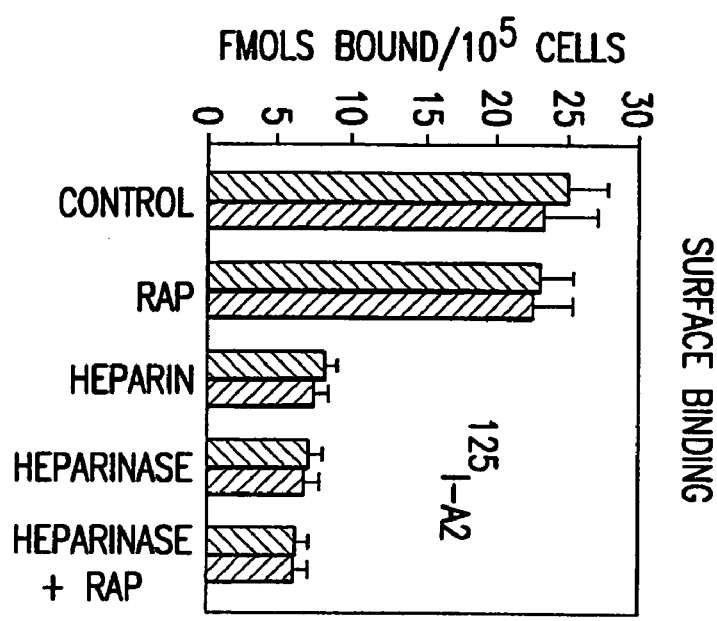
Figure 1D:
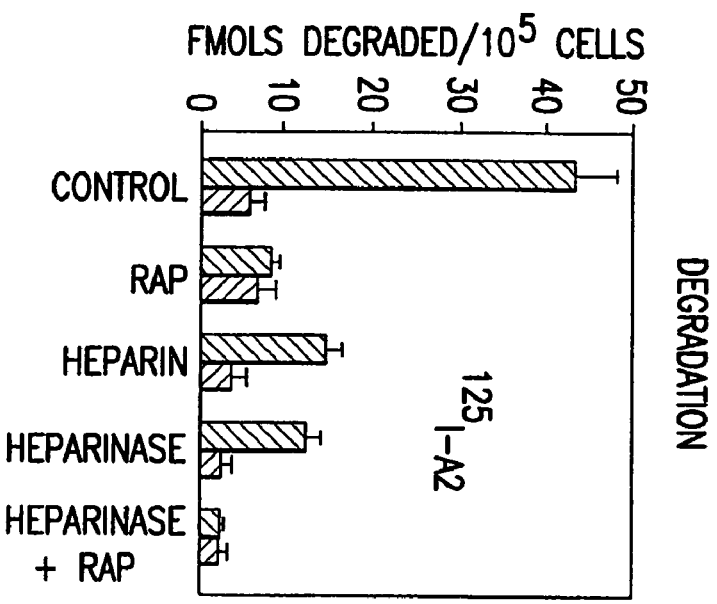
Figure 2A:
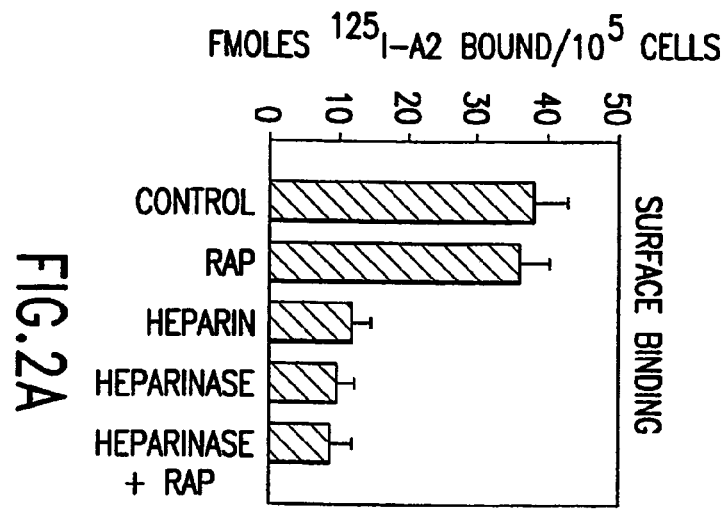
FIGS. 2A–2F. Effect of RAP, heparin and heparinase on surface binding, internalization and degradation of the $^{125}$I-A2 subunit of fVIII by smooth muscle cells (SMC) and alveolar epithelial cells (T2). Wells containing 10$^5$ SMC cells (gray bars) or T2 cells (hatched bars) were preincubated with or without heparinase as described in Example 2. Following incubation of the cells with 1 nM of $^{125}$I-A2 in the absence or presence of RAP (1 µM) or heparin (100 µg/ml) for 6 hours at 37° C., surface binding (FIGS. 2A and D), internalization (FIGS. 2B and 2E) and degradation (FIGS. 2C and 2F) of $^{125}$I-A2 were determined as described in Example 2. Each data point represents the mean value and standard deviation of duplicate determinations.
Figure 2B:
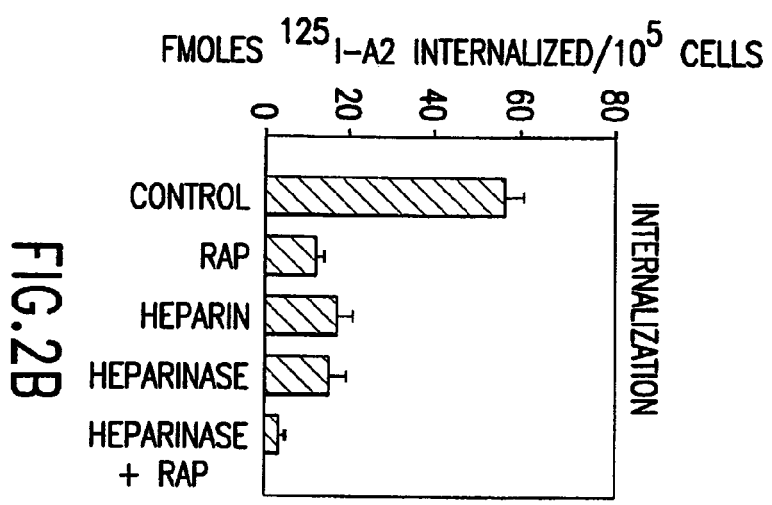
Figure 2C:
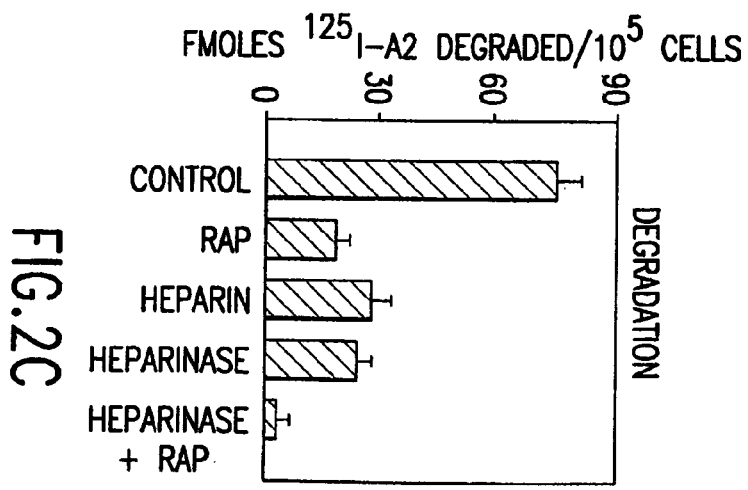
Figure 2D:
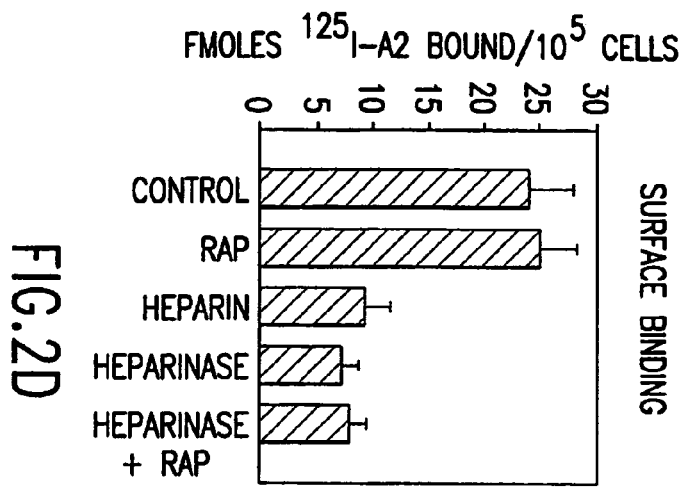
Figure 2E:
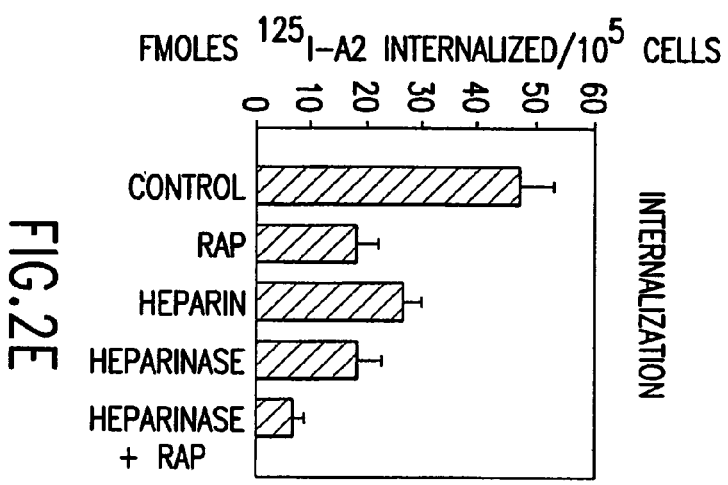
Figure 2F:
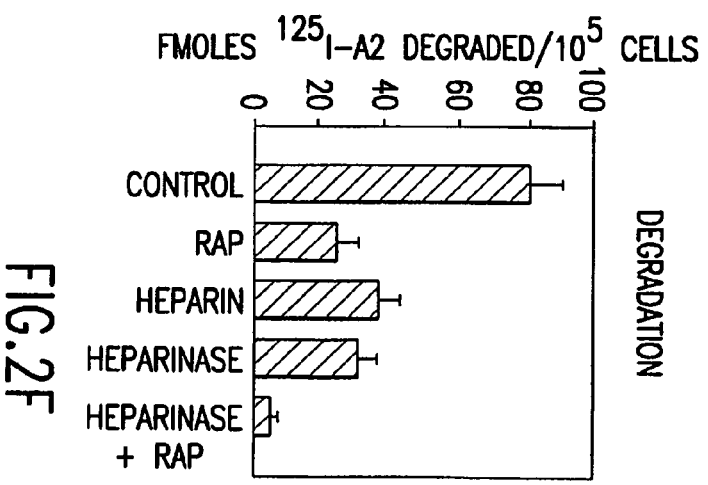

The major fVIII site involved in binding to HSPGs is located within its A2 domain. Since the fVIII site responsible for interaction with LRP is located within the A2 domain of fVIII (Saenko, E. L., et al., *J. Biol. Chem.* 274:37685–37692 (1999)), it is expected that LRP expressing cells will bind and catabolize isolated A2 domain. Indeed, we found that MEF cells bound and degraded isolated $^{125}$I-A2 domain (FIGS. 1C and D). Noteworthy, surface binding of $^{125}$I-A2 was inhibited by heparin and heparinase but not by RAP (FIG. 1C), showing that HSPGs are involved in the surface binding of A2, similar to that found for fVIII/vWf. In contrast to surface binding, degradation of $^{125}$I-A2 in LRP-expressing cells was inhibited by RAP, consistent with the presence of a LRP-binding site within the A2 domain (Saenko, E. L., et al., *J. Biol. Chem.* 274:37685–37692 (1999)). Degradation of A2 was also inhibited by heparin or heparinase, and the combination of heparinase and RAP led to an almost complete suppression of degradation (FIG. 1D). Involvement of HSPGs in the catabolism of isolated A2 domain indicates that it contains an HSPGs-binding site.

To examine whether the involvement of HSPGs in LRP-mediated catabolism of A2 is a common feature of LRP-expressing cells, we tested the binding of A2 to human smooth muscle cells (SMC) and alveolar epithelial cells (T2) expressing LRP and HSPGs (Moestrup, S. K., et al., *Cell Tissue Res.* 269:375–382 (1992)). Both in the SMC and T2 cells heparin and heparinase significantly inhibited surface binding, internalization and degradation of $^{125}$I-A2 (FIGS. 2A–2F). Addition of RAP to heparinase-treated cells had no effect on the $^{125}$I-A2 binding, but led to a further decrease of the internalization and degradation. Thus, the effects of heparinase and RAP on A2 catabolism in MEF, SMC and T2 are similar, indicating that LRP and HSPGs are simultaneously involved in A2 catabolism by different LRP-expressing cells.

Figure 3:
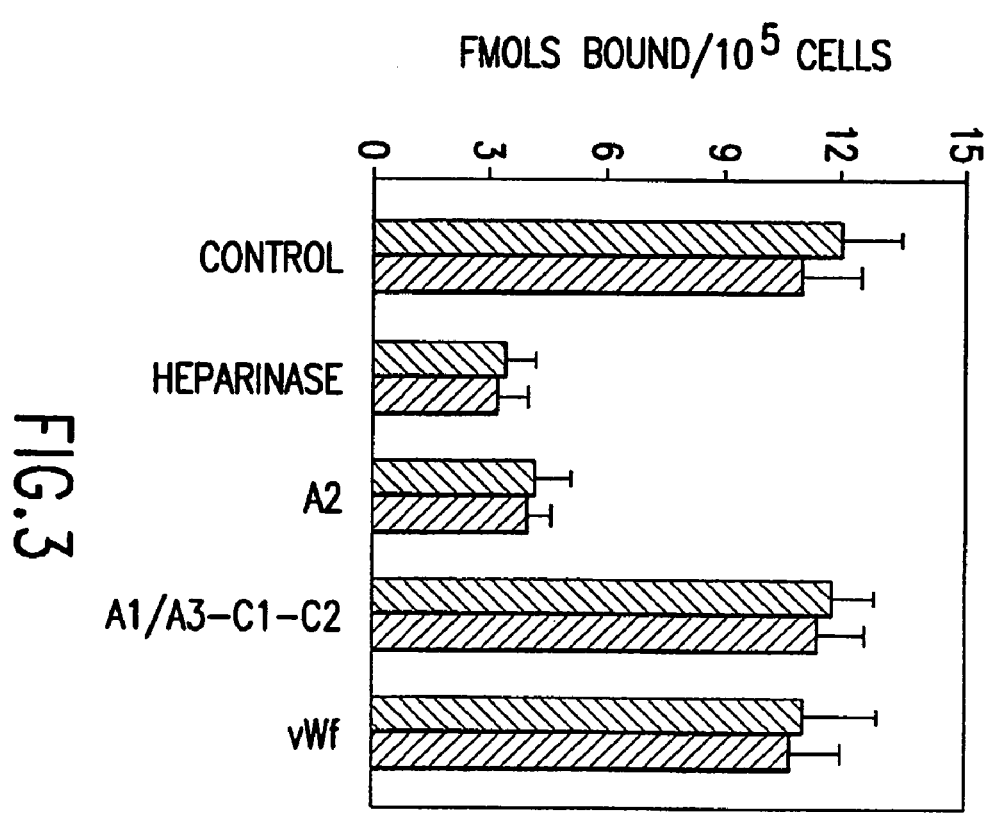
FIG. 3. Effect of fVIII fragments and vWf on binding of fVIII/vWf complex to the surface of MEF cells. Wells containing 2×10$^5$ LRP-expressing MEF cells (solid bars) or control LRP-deficient PEA 13 cells (gray bars) were preincubated with or without heparinase as described in Example 2. One nM $^{125}$I-fVIII/vWf complex was added to the cells in the absence of any competitor (control) or in the presence of 200 nM each of A2, A1/A3-C1-C2, or vWf and incubated for 2 h at 4° C., and surface-bound radioactivity was determined, as described in Example 2. Each data point represents the mean value and standard deviation of duplicate determinations.

We next examined whether the A2 domain is fully responsible for the binding of fVIII/vWf complex to cell surface HSPGs. This was performed by studying the effect of a 200-fold molar excess of fVIII fragments and vWf on the surface binding of $^{125}$I-fVIII/vWf complex to MEF and PEA13 cells. As seen from FIG. 3, A2 inhibited the binding of $^{125}$I-fVIII/vWf complex to both cells types to the level observed for heparinase-treated cells. In contrast, neither A1/A3-C1-C2 heterodimer nor vWf were able to inhibit the binding of the $^{125}$I-fVIII/vWf complex. This shows that fVIII but not vWf is responsible for the binding of fVIII/vWf complex to cell surface HSPGs and that the major HSPGs-binding site of fVIII is located within the A2 domain.

Figure 4B:
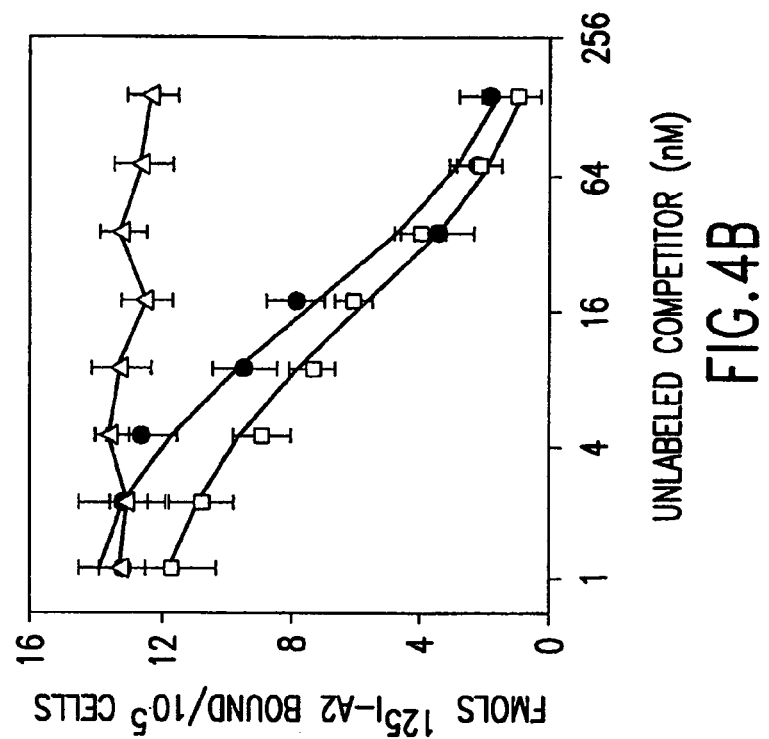
FIGS. 4A–4B. Determination of parameters for A2 binding to the surface of MEF cells.
Figure 4A:
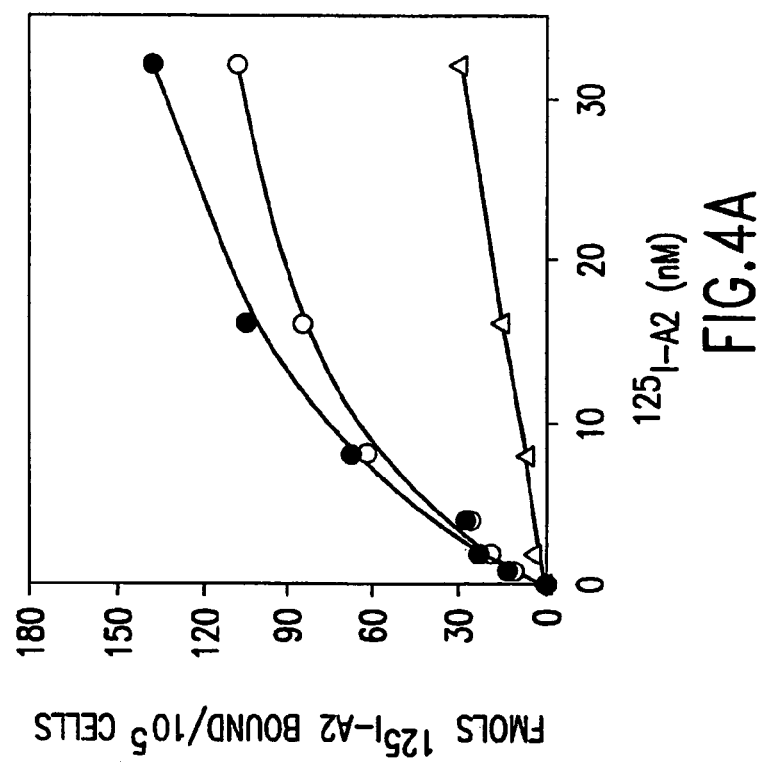

The A2 domain and fVIII/vWf complex bind cells with similar affinities. The presence of the major HSPGs binding site within A2 implies that binding affinities of A2 and fVIII/vWf for the cells should be similar. To verify this, we first determined the binding affinity of $^{125}$I-A2 to MEF cells in a saturation binding experiment. Nonspecific binding in the presence of a 100-fold excess unlabeled A2 was approximately 18% of total $^{125}$I-A2 binding. The specific binding was adequately described by a model showing the existence of a single class of binding sites ($9.6 \times 10^4$ sites per cell) with $K_d$ of 15±2.8 nM. In a control experiment, the $^{125}$I-A2 binding curve obtained in the presence of RAP (1 μM) (data not shown) was identical to that obtained in the absence of RAP (FIG. 4A). To verify that A2 and fVIII/vWf complex bind to the same sites, we performed a displacement of $^{125}$I-A2 (1 nM) by unlabeled A2 or fVIII/vWf. In this assay, A2 and fVIII/vWf were found to be equal competitors (FIG. 4B) with $K_i$ values of 18.3±3.2 nM and 23.5±2.7 nM, respectively. The similarity of the $K_i$ values further supports the conclusion that the binding of fVIII/vWf complex to HSPGs is mediated by the A2 domain of fVIII. Noteworthy, the binding properties of A2 were not altered by $^{125}$I-labeling, since the $K_d$ and $K_i$ obtained for A2 using direct binding or homologous displacement are similar.

Figure 5:
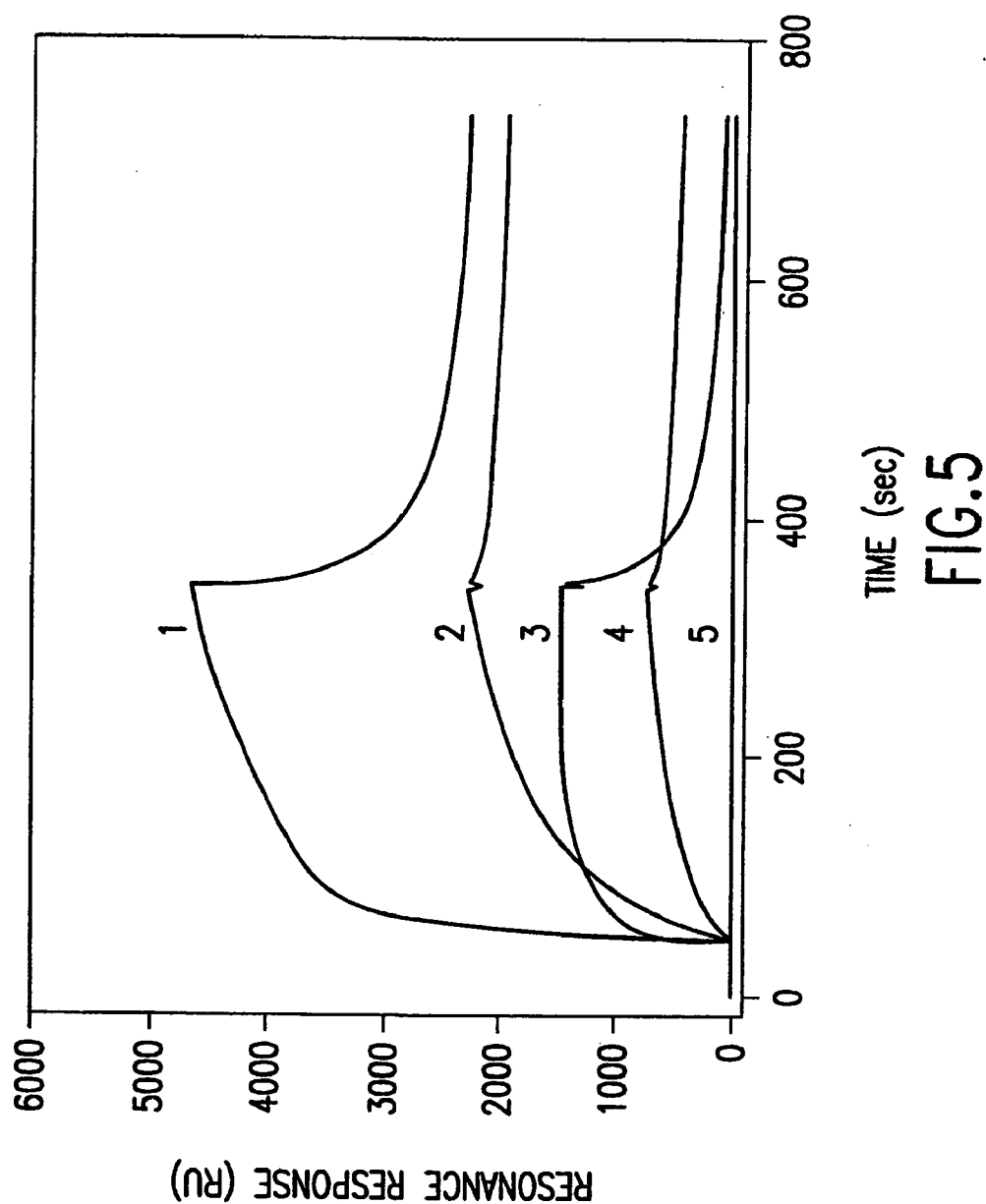
FIG. 5. Binding of fVIII and its fragments to heparin using the SPR technique. Heparin was immobilized to a biosensor chip as described in Example 2. Binding of 500 nM of fVIII (curve 1), HCh (curve 2), LCh (curve 3), A2 (curve 4), and A1 (curve 5) were measured for 5 min at the flow rate of 10 µl/min. Dissociation kinetics were measured upon replacement of the ligand solution by buffer, which was continuously changed at a flow rate of 10 µl/min. The kinetic curves were corrected for nonspecific binding by subtracting the signals obtained in the absence of immobilized heparin, which were less than 6% of the binding to heparin-coated chip.

A major site within A2 and a minor site within LCh are involved in fVIII binding to heparin. To examine whether A2 is the only site responsible for fVIIII interaction with HSPGs, we tested the binding of A2 and other fVIII fragments to heparin, used as a model molecule of carbohydrate portions of HSPGs. We found that fVIII, its A2 domain, HCh (containing A2), but not A1 were able to bind to heparin in a SPR-based assay (FIG. 5), consistent with the presence of the heparin-binding site within A2. Unexpectedly, LCh was also able to bind heparin, indicating that it contains another fVIII heparin-binding site. Consistent with this, fVIII kinetics was optimally fitted to a model showing the presence of two heparin binding sites ($K_d$s are 28 and 630 nM) within fVIII molecule. The kinetic parameters for fVIII and its fragments derived from the data in FIG. 5 are shown in Table 3. As seen from the Table, the site present in A2 (site 1) has a high affinity for heparin ($K_d$=28 nM), whereas the site present in LCh (site 2) has a low affinity ($K_d$=630 nM). The 20-fold lower affinity of the LCh site implies that its contribution to fVIII binding to heparin or HSPGs is not significant. Remarkably, the affinities of fVIII and A2 for heparin (Table 3) are similar to the affinities of fVIII/vWf complex and A2 for the cell surface HSPGs (18 and 23 nM, respectively). Altogether, these data further show that the major fVIII site responsible for binding to HSPGs is located within the A2 domain.

TABLE 3

Kinetic parameters for binding of fVIII and its fragments to heparin.

| Ligand | $k_{on}(M^{-1}s^{-1})$ | $k_{off}(s^{-1})$ | $K_d(nM)$ |
|---|---|---|---|
| FVIII | 1.(1.4 ± 0.034) × $10^4$ | (3.91 ± 0.4) × $10^{-4}$ | 27.93 ± 2.94 |
|  | 2.(8.24 ± 0.12) × $10^4$ | (5.38 ± 0.7) × $10^{-2}$ | 652.91 ± 12.68 |
| HCh | (1.32 ± 0.038) × $10^4$ | (3.1 ± 0.22) × $10^{-4}$ | 23.48 ± 1.79 |
| A2 domain | (1.63 ± 0.053) × $10^4$ | (4.2 ± 0.16) × $10^{-4}$ | 25.77 ± 1.29 |
| LCh | (7.84 ± 0.156) × $10^4$ | (4.48 ± 0.06) × $10^{-2}$ | 571 ± 13.5 |

Table 3. Association and dissociation of fVIII and its fragments to immobilized heparin were assessed in SPR-based experiment shown in FIG. 5. The kinetic data obtained for fVIII were optimally fitted using model of implying presence of two independent heparin-binding sites within the fVIII molecule. In the Table, these sites are referred to as 1 and 2. The kinetics of HCh, A2 and LCh interaction with heparin was optimized using a model assuming one heparin-binding site within each fragment. The association rate constants ($k_{on}$), dissociation rate constants ($k_{off}$) and affinities ($Kd=k_{on}/k_{off}$) were derived from the SPR data using Biacore software BIAevaluation 3.1.

The region of the A2 domain delineated by residues 558–565 is involved in binding to heparin. Localization of the A2 domain heparin-binding site was initiated by the previous findings that heparin inhibits Xase activity (Barrow, R. T., et al., J. Biol. Chem. 269:593–598 (1994); Barrow, R. T., et al., J. Biol. Chem. 269:26796–26800 (1994)) and fVIIIa can be substituted by A2 in the Xase assay (Fay, P. J. and Scandella, D., J. Biol. Chem. 274: 29826–29830 (1999)). We found that heparin is also inhibitory in the A2-dependent Xase assay (FIG. 6A). The effect was dose-dependent and 90% inhibition was observed at 10 μg/ml (~600 nM) of heparin.

Since it was previously shown that heparin does not inhibit interaction of the Xase complex with its substrate (factor X) (Barrow, R. T., et al., J. Biol. Chem. 269: 26796–26800 (1994)), we proposed that heparin inhibits Xase assembly by preventing A2 binding to factor IXa. To examine this possibility, we tested the effect of heparin on A2 binding to factor IXa by the fluorescent anisotropy technique. The experiment was based on a previous observation that the anisotropy of active site modified FI-FFR-fIXa moderately increases upon binding of A2 (Fay, P. J. and Scandella, D., J. Biol. Chem. 274:29826–29830 (1999)) and this effect is more pronounced in the presence of factor X (Fay, P. J., et al., J. Biol. Chem. 273:19049–19054 (1998); Fay, P. J. and Scandella, D., J. Biol. Chem. 274:29826–29830 (1999)). We found that heparin inhibited the increase of anisotropy in a dose-dependent fashion, either in the absence or presence of factor Xa (FIG. 6B). The maximal effect of heparin was observed at ≧30 μg/ml, which is similar to that completely suppressing the factor Xase assay (FIG. 6A). In a control experiment performed in the absence of A2, heparin did not affect the anisotropy of FI-FFR-fIXa either in the absence and in presence of factor X.

The above findings show that heparin blocks the interaction between the A2 subunit and factor IXa, which might be due to an overlap of the A2 domain binding sites for heparin and for factor IXa. Since two regions within the A2 domain, 484–509 and 558–565, are known to be directly involved in the interaction with factor IXa (Fay, P. J. and Scandella, D., J. Biol. Chem. 274:29826–29830 (1999); Fay, P. J., et al, J. Biol. Chem. 269:20522–20527 (1994)), we tested the effects of these peptides on the binding of A2 to heparin. In a SPR-based experiment, the peptide 558–565 inhibited binding by 78% at 800 μM (FIG. 7A). In contrast, at the same concentration, the peptide 484–509 inhibited binding by approximately 25%, and the peptide 417–428 had no effect. This shows that the A2 domain region 558–565 is involved in the binding of fVIII to heparin and to cell surface HSPGs.

Figure 8:
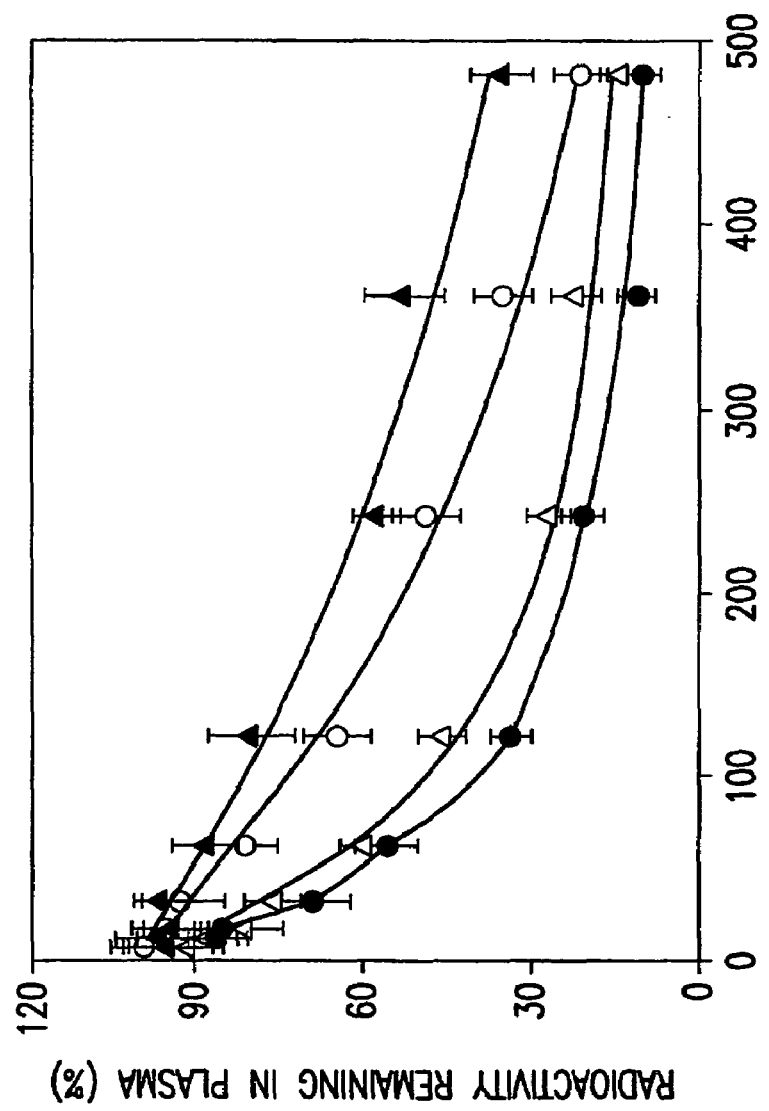
FIG. 8. Effect of protamine on clearance of $^{125}$I-fVIII/vWf from plasma of mice. BALB/c mice were injected with 100 µl 0.2 mM protamine (Δ) or 150 µM RAP (○) separately or with 100 µl 0.2 mM protamine and 150 µM RAP in combination (▲) 2 min prior to the injection of 100 µl samples containing $^{125}$I-fVIII (15 nM) and vWf (750 nM). In the control experiment (●), clearance of $^{125}$I-fVIII/vWf complex was studied in the absence of any added agent. At the indicated time points, blood samples were taken and counted for radioactivity. The percentage of ligand remaining in circulation was calculated taking the radioactivity of an aliquot taken at 1 min after injection as 100%. $^{125}$I-fVIII clearance was examined in four mice for each of the above conditions. The curves show the best fit of the experimental data to Equation 1 (see Example 2) describing biphasic exponential clearance of fVIII.

Cell surface proteoglycans participate in fVIII catabolism in vivo. To examine whether HSPGs contribute to fVIII clearance in vivo, fVIII clearance studies were performed in mice in the presence of protamine, which prevents HSPGs from interacting with their ligands (Warshawsky, L., et al., J. Biol. Chem. 271:25873–25879 (1996); Narita, M., et al., J. Biol. Chem. 270:24800–24804 (1995)). The data shown in FIG. 8 were fitted to the previously used double exponential model (Saenko, E. L., et al., J. Biol. Chem. 274:37685–37692 (1999)), showing the existence of fast and slow phases of fVIII clearance. This model is described by the following equation:

$$C = C_1 \exp(-k_1 t) + C_2 \exp(-k_2 t)$$

where C is the percent of $^{125}$I-fVIII remaining in plasma at a given time, $k_1$ and $k_2$ are the kinetic rate constants corresponding to the fast and slow phases of fVIII clearance, and $C_1$ and $C_2$ are percentages of administered radioactivity removed during the fast and slow phases of clearance, respectively. The values of $k_1$, $k_2$, $C_1$, and $C_2$ constants were derived for each clearance curve by fitting C versus t to the above equation. At a saturating concentration of RAP, the rate of the fast phase of clearance was dramatically reduced (Table 4), resulting in a prolongation of the half-life of fVIII by 3.5-fold, similar to that shown previously (Examples 3–4; Saenko, E. L., et al., *J. Biol. Chem.* 274:37685–37692 (1999)). Administration of protamine prolonged the fVIII half-life by 1.6-fold and reduced the rates of both phases of clearance (Table 2), which shows that HSPGs contribute to both RAP-sensitive and RAP-independent pathways of fVIII clearance. Noteworthy, co-injection of RAP and protamine resulted in a greater increase of the fVIII half-life (5.5-fold), than injection of RAP alone (3.5-fold). The above data demonstrate that HSPGs participate in fVIII clearance in vivo and are involved in the RAP-sensitive (most likely LRP-mediated) and RAP-independent catabolic pathways.

TABLE 4

The effect of RAP and protamine on the parameters of fVIII clearance from plasma of mice.

| Added Agent | C1 (%) | C2 (%) | $K_1$ (min$^{-1}$) | $K_2$ (min$^{-1}$) |
|---|---|---|---|---|
| None | 58 ± 3.6 | 42 ± 3.7 | 0.0208 ± 0.0026 | 0.00345 ± 0.0009 |
| RAP (150 µM) | 7.4 ± 3.8 | 92.6 ± 6.2 | 0.00107 ± 0.0008 | 0.00367 ± 0.0012 |
| protamine (0.2 mM) | 63 ± 6.5 | 37 ± 7.6 | 0.0118 ± 0.0007 | 0.00225 ± 0.0004 |
| RAP + protamine | 12 ± 3.4 | 88 ± 6.5 | 0.0007 ± 0.0006 | 0.00232 ± 0.0006 |

Table 4. The values of the kinetic rate constants $k_1$ and $k_2$, corresponding to the fast and slow phases of fVIII clearance and the percents of total radioactivity ($C_1$ and $C_2$, respectively) removed during these phases were determined by fitting clearance data shown in FIG. 7A as described in the Results Section.

Figure 9:
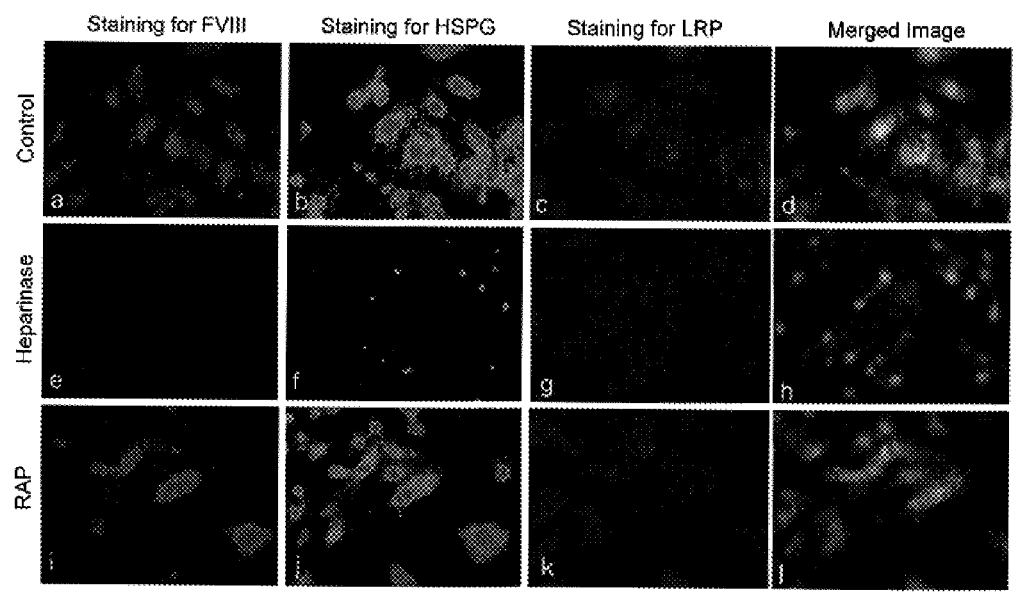
FIGS. 9A–9L. Microscopy studies of surface binding of fVIII from its complex with vWf by HEP G2 cells. Control untreated HEP G2 cells (FIGS. 9A–9D) and the cells treated with heparinase (FIGS. 9E–9H) or RAP (FIGS. 9I–9L) were incubated with 10 nM of fVIII/vWf complex for 2 h at 4° C. This was followed by fixing the cells and staining for fVIII using Texas Red (red images in FIGS. 9A, 9E, 9I), for HSPGs using AMCA (blue images in FIGS. 9B, 9F, 9G) and for LRP using FITC (green images in FIGS. 9C, 9G, 9K), as described in Example 2. Each type of staining was visualized using a selective fluorescent filter block. The merged images (FIGS. 9D, 9H, 9I) were obtained by superimposing the single-stained images as described in Example 2.

FVIII is co-localized with HSPGs on the surface of LRP-expressing hepatic cells. We previously found that injection of $^{125}$I-fVIII/vWf complex into mice led to accumulation of most of the radioactivity in liver (Examples 3 and 4; Saenko, E. L., et al., *J. Biol. Chem.* 274:37685–37692 (1999)), where LRP is present in high abundance (Moestrup, S. K., et al., *Cell Tissue Res.* 269:375–382 (1992)). To elucidate whether HSPGs are involved in the initial fVIII binding to the liver cells, we performed direct visualization of fVIII, HSPGs and LRP in hepatic cells HEP G2, expressing both LRP and HSPGs (Butzow, R., et al., *J. Cell. Biol.* 122:721–727 (1993)). The cells were incubated with fVIII/vWf complex at 4° C. followed by triple-label immunofluorescent staining for fVIII, LRP and HSPGs (FIGS. 9A–9L). For each preparation, the distribution of fVIII, HSPGs or LRP is shown in red, blue and green images, respectively. For control cells, individual staining for fVIII, HSPGs and LRP are represented by the images in FIGS. 9A, 9B, and 9C, respectively. FVIII was distributed on the cell surface in a grainy pattern, typical for cell surface but not for cytoplasmic staining. The merged image in FIG. 9D demonstrates that fVIII co-localized predominantly with HSPGs as seen by the purple areas resulting from superimposing red and blue staining for fVIII and HSPGs, respectively. Co-localization of surface-bound fVIII with LRP was negligible, since large areas in the merged image remained green but not yellow, as would be expected for superimposed red and green images. Consistent with this, treatment of the cells by heparinase to remove glycosamine residues from HSPGs (FIG. 9F) led to a dramatic reduction of bound fVIII (FIG. 9E) and to a lack of purple areas on the merged image (FIG. 9H). In contrast, blocking of LRP by RAP (FIGS. 9I–9L) did not appreciably alter fVIII binding (FIG. 9I) compared to the control cells (FIG. 9A). In the merged image (FIG. 9L) fVIII remained colocalized with HSPGs, consistent with a negligible role of LRP in the initial surface binding of fVIII/vWf complex. Thus, the microscopy study confirms that HSPGs are the major receptors responsible for initial binding of fVIII/vWf complex to the surface of LRP expressing cells.

Discussion

In the present study we found that cell surface HSPGs facilitate LRP-mediated catabolism of fVIII from its complex with vWf in cell culture and in vivo. In LRP-expressing cells, the bulk of initial binding of fVIII/vWf complex to the cells occurs via HSPGs, which cooperate with LRP receptor in the subsequent internalization of the fVIII molecule. In mice, the simultaneous blocking of HSPGs and LRP led to a significant prolongation of the fVIII half-life, compared to the fVIII half-life when HSPGs and LRP were individually blocked.

The interaction of fVIII/vWf complex with HSPGs occurs via the A2 domain of fVIII, based on observations that in LRP-expressing cells (i) the A2 subunit, but not other portions of fVIII or isolated vWf, strongly inhibited this binding; (ii) A2 subunit and fVIII/vWf complex bind to the cell surface with similar affinities; and (iii) A2 and fVIII have similar affinities for binding to heparin in a purified system. Although vWf was previously shown to interact with heparin, the apparent lack of its contribution to the binding is consistent with its weak affinity for heparin ($K_d$ 2 µM, 78 µM (Poletti, L. F., et al., *Arterioscler. Thromb. Vasc. Biol.* 17:925–931 (1997); Maruch, D., et al., *Thromb. Haemost.* 71:141–146 (1994)), which is two to three orders of magnitude lower than the affinity determined in the present study for the fVIII and A2 interactions with heparin (~28 nM). The A2 site involved in binding to heparin was localized to the region 558–565 based on the ability of the synthetic peptide encompassing this region to inhibit A2 binding to heparin. Noteworthy, the peptide 484–509, which corresponds to the previously localized LRP binding site (Examples 4–5; Saenko, E. L., et al., *J. Biol. Chem.* 274: 37685–37692 (1999)), did not appreciably inhibit the binding, showing that the A2 domain sites responsible for binding to LRP and HSPGs are distinct.

Heparin-binding sites of proteins are commonly represented by cationic clusters formed by Arg and/or Lys, which interact with the anionic portion of the heparan-sulfate glycosaminoglycans molecule (Mann, D., et al., *J. Biol. Chem.* 269:23661–23667 (1994)). Within the 558–565 region and in the close proximity to it, there are Lys[556], Lys[562], Lys[570] and Arg[571] exposed on the A2 surface according to the previously published 3D model of the A2 domain (Pemberton, S., et al., *Blood* 89:2413–2421 (1997)). Although we found another heparin binding site of fVIII within its LCh, this low affinity-binding site does not significantly contribute to interaction of fVIII with HSPGs, and in addition, may be blocked by vWf, which binds to LCh of fVIII (Saenko, E. L. and Scandella, D., *J. Biol. Chem.* 272:18007–18014 (1997)).

Cooperation of HSPGs with LRP in catabolizing fVIII is similar to their role in the catabolism of most heparin-binding LRP ligands (Warshawsky, I., et al., *Proc. Natl. Acad. Sci. U.S.A.* 91:6664–6668 (1994); Chappell, D. A., et al., *J. Biol. Chem.* 268:14168–14175 (1993); Knauer, M. F., et al., *J. Biol. Chem.* 274:275–281 (1999); Kounnas, M. Z., et al., *J. Biol. Chem.* 270:9307–9312 (1995); Knauer, M. F., et al., *J. Biol. Chem.* 272:29039–29045 (1997); Mikhailenko, I., et al., *J. Biol. Chem.* 272:6784–6791 (1997)). The proposed role of HSPGs to in concentrating the ligands on the cell surface and in facilitating their subsequent internalization by presenting them to LRP (Strickland, D. K., et al., *FASEB J.* 9:890–898 (1995); Knauer, M. F., et al., *J. Biol. Chem.* 274:275–281 (1999)) is consistent with our data, since the affinity of fVIII/vWf complex for HSPGs and heparin ($K_d$=15–30 nM) is higher than that for LRP ($K_d$=116 nM (Saenko, E. L., et al., *J. Biol. Chem.* 274:37685–37692 (1999))).

Figure 10:
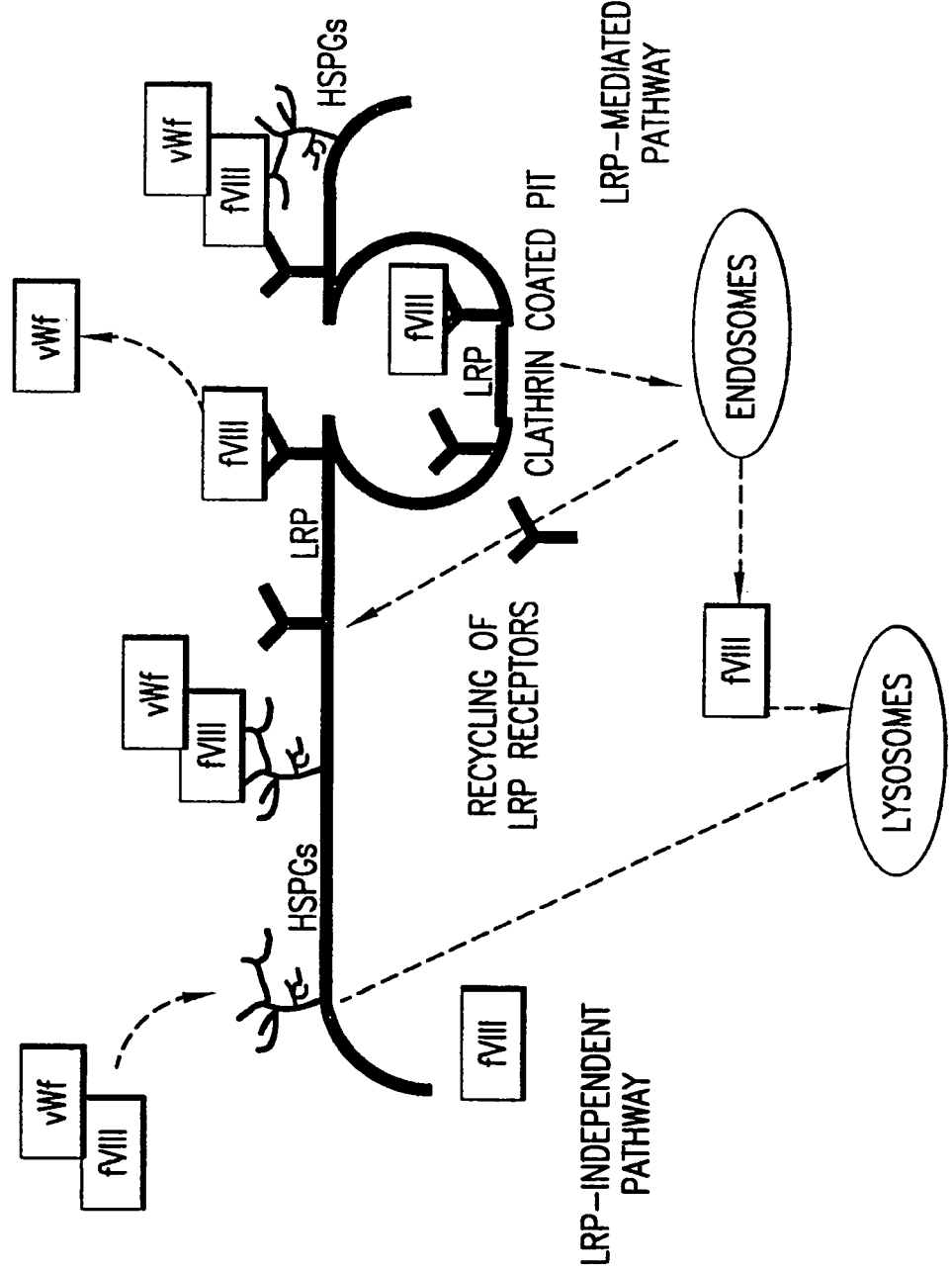
FIG. 10. Molecular model of cell surface binding of fVIII/vWf complex and subsequent catabolism of fVIII. Initial binding of fVIII/vWf complex occurs mainly via an interaction with HSPGs, followed by LRP-mediated endocytosis occurring via clathrin-coated pits (Chen, W. J., et al., *J. Biol. Chem.* 265:3116–3123 (1990)) and LRP-independent endocytosis which is directly mediated by HSPGs. Since vWf does not follow fVIII in the endocytic pathway in the cell culture experiments (Saenko, E. L., et al., *J. Biol. Chem.* 274:37685–37692 (1999)), it apparently dissociates from fVIII prior to entry of the complex into endosomal compartments.

The fact that in LRP-expressing cells, RAP effectively inhibited internalization and degradation of fVIII is consistent with our previous data that LRP is involved in the catabolism of fVIII (Saenko, E. L., et al., *J. Biol. Chem.* 274:37685–37692 (1999)). At the same time, the finding that LRP-deficient cells were also able to internalize and degrade fVIII and that this process was strongly inhibited by heparinase, shows the existence of a LRP-independent pathway of fVIII catabolism that also is mediated by HSPGs. This is consistent with the biphasic clearance of fVIII in vivo, which reflects the existence of two different pathways of fVIII catabolism. According to our findings, both pathways involve HSPGs, as shown by the inhibition of both fast and slow phases of fVIII clearance by protamine. Since the fast phase of the fVIII clearance is also RAP-sensitive, we conclude that in this phase the fVIII/vWf complex binds to cell surface HSPGs, followed by endocytosis of fVIII that is mediated by LRP. The slow phase of fVIII clearance is LRP-independent but is also facilitated by HSPGS, similar to the LRP-independent pathway in cell culture. Noteworthy, simultaneous blocking of HSPGs and LRP by protamine and RAP, respectively, did not completely block the fVIII clearance in mice. The role of HSPGs based on the experiments in a cell model system and in vivo is depicted in FIG. 10, where catabolism of fVIII from its complex with vWf occurs via initial binding of the complex to HSPGs, followed by both the LRP-mediated and LRP-independent endocytosis and degradation of fVIII. The model indicates that vWf dissociates prior to fVIII internalization, since we had previously shown that vWf does not follow fVIII in the endocytic pathway (Saenko, E. L., et al., *J. Biol. Chem.* 274:37685–37692 (1999)).

The finding that isolated A2 domain of fVIII can be catabolized by HSPGs- and LRP-mediated mechanisms reflects the existence of specific pathways of clearance of activated fVIII. Heterotrimeric fVIIIa (A1/A2/A3-C1-C2) is an unstable molecule due to its rapid but reversible dissociation into the A2 and A1/A3-C1-C2 portions (Fay, P. J., et al., *J. Biol. Chem.* 266:8957–8962 (1991); Fay, P. J. and Smudzin, T. M., *J. Biol. Chem.* 267:13246–13250 (1992)). Since the A2 subunit may reassemble with A1/A3-A3-C1 and restore fVIIIa activity and isolated A2 retains a weak fVIIIa-like ability to support Xase, clearance of the isolated A2 subunit has evolved as a mechanism for preventing formation of the Xase complex at inappropriate sites in the vasculature.

In summary, we demonstrated that fVIII catabolism from its complex with vWf involves initial binding of the complex to cell surface HSPGs, which is due to the interaction between polysaccharide portions of HSPGs and the heparin-binding site in the fVIII A2 domain. Upon binding of the fVIII/vWf complex to HSPGs, the fVIII molecule is catabolized via two pathways, LRP-mediated and LRP-independent. Finally, both HSPGs and LRP are involved in fVIII clearance in vivo, since simultaneous blocking of these receptors dramatically prolonged the half-life of fVIII in circulation.

Example 3

Activated factor VIII (fVIIIa) functions in the intrinsic pathway of blood coagulation as a cofactor for factor IXa in the conversion of factor X to activated factor X (Xa). When IXa is bound to membrane and fVIII the rate of factor X to IXa conversion increases 100,000–1,000,000 fold. The procoagulant activity of fVIIIa is regulated by rapid and potentially reversible dissociation of the A2 subunit from the A1/A3C1C2 dimer and by activated protein C (APC) proteolysis of the residual fVIIIa. Removal of the A2 and A1/A3C1C2 fragments is an additional in vivo mechanism to control factor VIIIa activity at the site of blood coagulation.

This was tested in a model system using mouse embryonic fibroblasts (MEF) that express low density lipoprotein receptor related protein (LRP) a multi ligand endocytic receptor and PEA 13 fibroblasts that are genetically deficient in LRP. Using the above model system the mechanisms of cellular uptake and degradation of thrombin activated fVIII subunits was studied to evaluate the role of these mechanisms in regulating fVIIIa levels.

Methods

Cell mediated ligand internalization and degradation assays. Cells were seeded into 24 well dishes and allowed to grow for 24 hours at 37° C. 5% $CO_2$ MEF and PEA 13 cells were incubated for selected time intervals at 37° C. with $^{125}$I-labeled fVIIIa fragments in the presence and absence of unlabeled competitors as described in the figure legends. Radioactivity appearing in the cell culture medium that was soluble after precipitation with 10% trichloroacetic acid (TCA) was taken to represent degraded ligand. Total ligand degradation was corrected by subtracting the amount of 10% TCA soluble radioactivity occurred in control wells lacking cells. The amount of labeled ligand bound to the cell surface or that was internalized by cells was determined as follows. Cells were washed with cold phosphate buffered saline and treated with a trypsin EDTA proteinase K solution. Surface bound material was defined as the amount of radioactive ligand released by this treatment and the amount of internalized ligand was defined as the amount of radioactivity which remained associated with the cell pellet following the treatment.

Determining of the A2 affinity for LRP. LRP (3.5 µg/ml) in 0.1 M $NaHCO_3$, pH 9.6 was incubated in Immulon I microtiter well strips for 16 hours at 4° C. After washing with TBS, 5 mM $CaCl_2$, 0.05% Tween 20 buffer (TBS-T) and blocking with 3% BSA, $^{125}$I-A2 (5 nM) and increasing concentrations unlabeled A2 (0–1750 nM) were added. Following the incubation for 1 hour at 37° C. and washing with TBS-T, the radioactivity bound to the wells was counted. $^{125}$I-A2 binding in the presence of unlabeled A2 was plotted using the computer program "Ligand." The $K_d$ value for A2/LRP binding was calculated from the displacement curve, showing a best fit of the data to a single class of sites.

Effect of RAP on the clearance of $^{125}$I-A2 domain from the plasma of mice. To elucidate the role of LRP receptor in the clearance of the A2 domain from plasma in vivo we tested the plasma level of $^{125}$I-labeled A2 in the presence and absence of RAP after tail vein injection in mice. 250 µl samples of A2 (36 nM), in the presence and absence of RAP (267 µM) were injected into the tail vein of BALB/c mice. At the indicated times, blood (50 µl) was collected into 10 µl of 0.5 M EDTA and counted for its $^{125}$I content. RAP significantly delays the plasma elimination of A2 domain. This experiment indicates that a RAP dependent hepatic receptor, LRP, plays a major role in the removal of A2 from circulation.

LRP receptor mediated internalization and degradation of the $^{125}$I-A2 domain by fibroblast cells. The cellular uptake and degradation of activated factor VIII fragments was studied using mouse embryonic fibroblast (MEF) cells expressing low density lipoprotein receptor—related protein (LRP), a multi ligand endocytic receptor, and PEA 13 cells represents fibroblasts lacking LRP. The fVIIIa subunit's interaction with MEF and PEA 13 cells represents an adequate model for in vivo processes because fibroblast cells became exposed to coagulation site upon vascular injury. LRP mediated internalization and degradation of some proteins (Thrombin:ATIII complex and other complexes of thrombin with inhibitors, tissue factor pathway inhibitor (TFPI)) involved in the coagulation cascade is known.

$^{125}$I-A2 (10 nM) was incubated with cells for the indicated times and the amount of surface bound, internalized and degraded $^{125}$I-labeled protein were determined as described under "Methods." The A2 domain was internalized and degraded by MEF cells but not by PEA 13 cells suggesting that expression of LRP receptor is required for these processes. The internalization and degradation of A2 was blocked by RAP, an inhibitor of LRP binding to its ligand.

Internalization of the $^{125}$I-A2 and APC cleaved A2 domain, by LRP presenting MEF cells and control PEA 13 cells, lacking LRP. Inactivation of fVIIIa by APC leads to a cleavage of the A2 at $Arg^{562}$. Since cofactor activity cannot be reconstituted from $A2_N/A2_C$ and A1/A3C1C2 dimer, we proposed that $A2_N/A2_C$ removal from circulation may occur by a mechanism different from that for intact A2. To examine the effect of proteolysis by APC on cellular internalization of the A2 domain, we compared the $^{125}$I-A2 and $^{125}$I-$A2_N/A2_C$ uptake by MEF and PEA 13 cells. We found that in contrast to A2 domain, the internalization of $_{125}$I-$A2_N/A2_C$ is not mediated by LRP receptor.

Binding the A2 domain to the immobilized LRP. To the microtiter wells with immobilized LRP, $^{125}$I-A2 (5 nM) and increasing concentrations of unlabeled A2 (0–1750 nM) were added. After incubation for 1 hour at 37° C., the wells were washed with TBS-T and radioactivity bound to the wells was counted. $^{125}$I-A2 binding in the presence of unlabeled A2 is expressed as the percentage of $^{125}$I-A2 binding, when no competitor was added. The data was analyzed using the computer program "Ligand". The $K_d$ value for A2/LRP binding calculated from the displacement data was 130 nM.

Internalization of $^{125}$I-labeled A1/A3C1C2 and $A1^{336}$/A3C1C2 by fibroblast cells. We proposed that a phospholipid binding site previously localized to the C2 domain of fVIII light chain mediates the cellular surface binding and internalization of A1/A3C1C2 and $A1^{336}$/A3C1C2 dimers. To test this hypothesis we determined internalization $^{125}$I-A1/A3C1C2 and $^{125}$I-$A1^{336}$/A3C1C2 by MEF cells in the presence and absence of anti-C2 domain monoclonal antibody NMC-VIII/5, which blocks the membrane binding sites of the C2 domain.

Wells containing 2×10$^5$ MEF cells were incubated with 3 nM of $^{125}$I-A1/A3C1C2 or 3 nM of $^{125}$I-$A1^{336}$/A3C1C2 at 37° C. in the presence or abs of 30 nM monoclonal antibody NMC-VIII/5. In the control experiments, PEA 13 cells lacking LRP were incubated as above with $^{125}$I-A1/A3C1C2 and $^{125}$I-A1/A3C1C2. At several times internalization of the dimers was measured as described under "Methods."

Since internalization of both $^{125}$I-A1/A3C1C2 and $^{125}$I-$A1^{336}$/A3C1C2 dimers was completely inhibited hy monoclonal antibody NMC-VIII/5, which recognizes the membrane binding site of fVIII C2 domain, we concluded that membrane binding of C2 is an important step required for internalization of the above dimers. The rate of internalization was similar for MEF and PEA 13 cells, which shows that LRP receptor is not involved in this process.

Degradation of $^{125}$I-A1/A3C1C2 and $^{125}$I-$A1^{336}$/A3C1C2 by MEF cells. MEF cells were incubated with $^{125}$I-A1/A3C1C2 (3 nM) or $^{125}$I-$A1^{336}$/A3C1C2 (3 nM) for 22 hours at 37° C. in the presence and absence PAP (1 µM). The degradation of dimers was measured as described under "Methods".

The degradation of A1/A3C1C2 dimer is RAP dependent. In contrast, degradation of APC cleaved $A1^{336}$/A3C1C2 dimer is RAP independent and does not correlate with LRP expression.

Conclusions

The A2 domain was internalized and degraded by mouse embryonic fibroblasts (MEF) which are expressing low density lipoprotein receptor-related protein (LRP), a multi ligand endocytic receptor. The internalization and degradation of A2 was blocked by RAP, an inhibitor of LRP binding to its ligands. In vivo clearance studies in mice demonstrated that RAP inhibited the clearance of $^{125}$I-A2 from circulation. The radioactivity was preferentially accumulated in liver in the absence but not in the presence of RAP. This indicates that a RAP sensitive hepatic receptor most likely LRP, plays a major role in the removal of $^{125}$I-A2 from the circulation.

The phospholipid binding site previously localized to the C2 domain of fVIII light chain mediates the cellular membrane binding and internalization of A1/A3C1C2 and $A1^{336}$/A3C1C2 dimers.

LRP receptor does not participate in cellular uptake and degradation of fragments $A2_N/A2_C$ and $A1^{336}$/A3C1C2, produced by irreversible inactivation of fVIIIa by APC. A2 and A1/A3C1C2 fragments produced by reversible inactivation of fVIIIa are removed by LRP-mediated and LRP-independent mechanisms, respectively. LRP is involved in the regulation of coagulation processes in vivo, by removal of A2 domain and A1/A3C1C2 dimer, the fragments from which active factor VIIIa can be reconstituted.

Example 4

The plasma glycoprotein factor VIII (fVIII) serves as a cofactor for the factor X activation complex in the intrinsic pathway of blood coagulation. FVIII circulates in plasma in a tight noncovalent complex with its carrier protein von Willebrand factor (vWf). Although the complex formation of fVIII with vWf is critical for maintenance of a normal half-life and level of fVIII in circulation, the mechanisms associated with fVIII turnover are not well defined. In the present study, we found that catabolism of fVIII is mediated by the low density lipoprotein receptor-related protein/$α_2$-macroglobulin receptor (LRP), a liver endocytic receptor responsible for in vivo clearance of a number of structurally unrelated ligands. A specific binding between fVIII and LRP was demonstrated by homologous ligand competition experiments, where a $K_d$ of 116 nM was determined for fVIII binding to LRP. A 39 kDa receptor-associated protein (RAP), an antagonist of ligand binding by LRP, completely inhibited fVIII binding to purified LRP. The region of fVIII involved in its binding to LRP was localized to the A2 domain residues 484–509, based on the ability of the isolated A2 domain and the synthetic A2 domain peptide 484–509 to prevent fVIII interaction with LRP. Since vWf did not inhibit fVIII binding to LRP, we proposed that LRP receptor may internalize fVIII from its complex with vWf. In agreement with this, mouse embryonic fibroblasts (MEF) that express LRP, but not fibroblasts genetically deficient in LRP (PEA 13), were able to internalize and degrade $^{125}$I-fVIII/vWf complex. The latter processes were competed by RAP and the A2 subunit of fVIII, indicating that cellular internalization and subsequent degradation were mediated by interaction of the A2 domain of fVIII with LRP. MEF cells were not able to internalize $^{125}$I-vWf from $^{125}$I-vWf/fVIII complex. This indicates that vWf does not follow fVIII in the LRP-mediated pathway and dissociates from fVIII at the early stage of endocytosis. In vivo clearance studies of $^{125}$I-fVIII/vWf complex in mice demonstrated that RAP prolonged the half-life of $^{125}$I-fVIII in circulation by 2.5-fold, indicating that a RAP-sensitive receptor, most likely LRP, is responsible for the plasma clearance of fVIII.

Introduction

Figure 11:
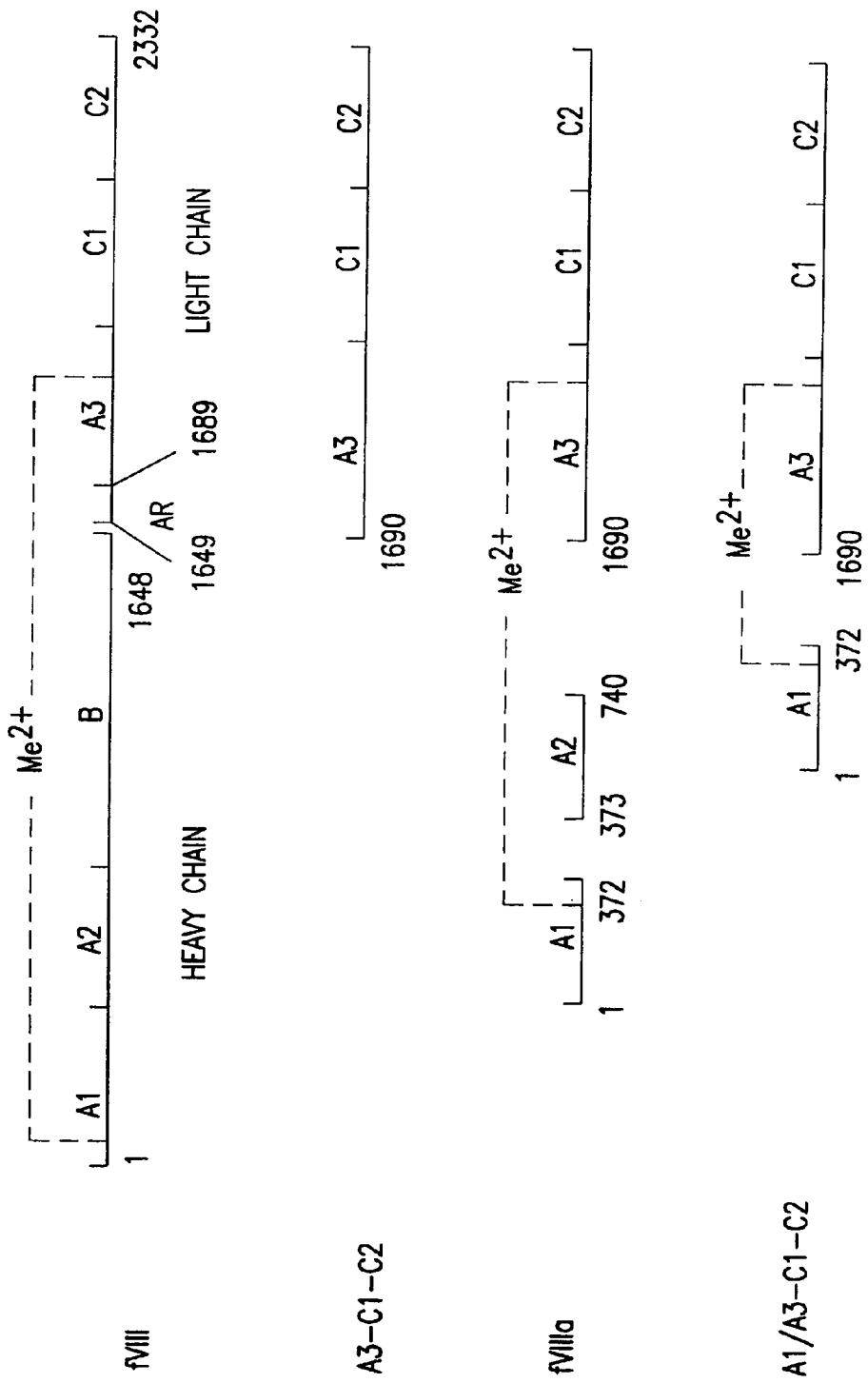
FIG. 11. Domain structure of fVIII and its fragments. The domain structure of mature fVIII protein is shown in line 1. The LCh acidic region is labeled as AR. Thrombin-cleaved LCh (A3-C1-C2), heterotrimeric fVIIIa (A1/A2/3-C1-C2) and heterodimer A1/A3-C1-C2 are shown in lines 2, 3 and 4.

The plasma glycoprotein factor VIII (fVIII) functions as a cofactor for the factor X activation enzyme complex in the intrinsic pathway of blood coagulation, and it is decreased or nonfunctional in patients with hemophilia A. The fVIII protein consists of a homologous A and C domains and a unique B domain which are arranged in the order A1-A2-B-A3-C1-C2 (Vehar, G. A., et al., Nature 312:337–340 (1984)). It is processed to a series of $Me^{2+}$ linked heterodimers produced by cleavage at the B-A3 junction (Fay, P. J., et al., Biochem. Biophys. Acta. 871:268–278 (1986)), generating a light chain (LCh) consisting of an acidic region (AR) and A3, C1, and C2 domains and a heavy chain (HCh) which consists of the A1, A2, and B domains (FIG. 11).

Transplantational studies both in animals and in humans demonstrated that the liver hepatocytes are the major fVIII-producing cells (Lewis, J. H., et al., N. Engl. J. Med 312:1189–1191 (1985); Bontempo, F. A., et al., Blood 69:1721–1724 (1987)). Immediately after release into circulation, fVIII binds with high affinity ($K_d$<0.5 nM (MacGregor, I. R., et al., Vox. Sang. 69:319–327 (1995); Saenko, E. L. and Scandella, D., J. Biol Chem 272:18007–18014 (1995)) to its carrier protein vWf to form a tight, noncovalent complex, which is required for maintenance of a normal fVIII level in the circulation. Complex formation with vWf stabilizes association of the LCh and HCh within fVIII molecule (Wise, R. J., et al., J. Biol. Chem. 266:21948–21955 (1991)) and prevents fVIII from C2-domain mediated binding to phospholipid membranes (Gilbert, G. E., et al., J. Biol. Chem. 267:1586115868 (1992)), activation by activated factor X (Koppelman, S. J., et al., J. Lab. Clin. Med. 123:585–593 (1994)) and from protein C-catalyzed inactivation (Fay, P. J., et al., J. Biol. Chem 266: 2172–2177 (1991)). vWf comprises a series of high molecular weight, disulfide-bonded multimers with molecular weight values as high as $2 \times 10^7$ Da (Hoyer, L. W. and Shainoff, J. R., Blood 55:1056–1059 (1980)) and circulates in plasma at 10 µg/ml or 50 nM, assuming a molecular mass of 270 kDa for vWf monomers (Girma, J.-P., et al., Biochemistry 25:3156–3163 (1986)). Since the concentration of fVIII in plasma is approximately 1 nM (Wion, K., et al., Nature 317:726–730 (1985)), one fVIII molecule is bound per 50 vWf monomers (Vlot, A. J., et al., Blood 85:3150–3157 (1995)).

Activation of fVIII by thrombin leads to dissociation of activated fVIII (fVIIIa) from vWf and to at least 100-fold increase of the cofactor activity. The fVIIIa is a A1/A2/A3-C1-C2 heterotrimer (Fay, P. J., et al., J. Biol. Chem 266: 8957–8962 (1991)) in which domains A1 and A3 retain the metal ion linkage (FIG. 1) and the stable dimer A1/A3-C1-C2 is weakly associated with the A2 subunit through electrostatic forces (Fay, P. J., et al., J. Biol. Chem 266:8957–8962 (1991)). Spontaneous dissociation of the A2 subunit from the heterotrimer results in non-proteolytic inactivation of fVIIIa.

Infusion of fVIII/vWf complex or purified plasma or recombinant fVIII into patients with severe hemophilia A who do not have fVIII (Fijnvandraat, K., et al., Thromb. Haemostas. 77:298–302 (1997); Morfini, M., et al., Thromb. Haemostas. 68:433–435 (1992)) or in normal individuals (Over, J., et al., J. Clin. Invest. 62:223–234 (1978)) results in a similar fVIII disappearance with a half-life of 12–14 hours. Although the complex between fVIII and vWf is crucial for normal half-life and level of fVIII in the circulation, the mechanisms associated with turnover of fVIII/vWf complex are not well defined. We proposed that fVIII/vWf complex is eliminated from plasma via clearance receptor and tested the possibility that this receptor is low density lipoprotein related protein receptor (LRP). Cellular endocytosis mediated by LRP was shown to be a mechanism of removal of a number of structurally unrelated ligands including several proteins related to coagulation or fibrilolysis. These ligands are: complexes of thrombin with antithrombin III (ATIII), heparin cofactor II (HC11) (Kounnas, M. Z., et al., J. Biol. Chem. 271:6523–6529 (1996)), protease nexin I (Knauer, M. F., et al., J. Biol. Chem. 272: 12261–12264 (1997)), complexes of urokinase-type and tissue-type plasminogen activators (u-PA and t-PA, respectively) with plasminogen activator inhibitor (PAI-1) (Nykjaer, A., et al., J. Biol. Chem. 267:14543–14546 (1992); Orth, K., et al., Proc. Natl. Acad. Sci. 89:7422–7426 (1992)), thrombospondin (Mikhailenko, I., et al., J. Biol. Chem. 272:6784–6791 (1997)), tissue factor pathway inhibitor (TFPI) (Warshawsky, I., et al., Proc. Natl. Acad. Sci. 91:6664–6668 (1994)), and factor Xa (Narita, M., et al., Blood 91:555–560 (1998); Ho, G., et al., J. Biol. Chem 271:9497–9502 (1996)).

LRP, a large cell-surface glycoprotein identical to $\alpha_2$-macroglobulin receptor (Strickland, D. K., et al., J. Biol. Chem. 265:17401–17404 (1990)), is a member of the low density lipoprotein (LDL) receptor family which also includes the LDL receptor, very low density lipoprotein (VLDL) receptor, vitellogenin receptor and glycoprotein 330 receptor. LRP receptor consists of the non-covalently linked 515 kDa α-chain (Herz, J., et al., EMBO J. 7:4119–4127 (1988)) containing binding sites for LRP ligands, and the 85 kDa transmembrane β-chain. Within the α-chain, cluster of cysteine-rich class A repeats is responsible for ligand binding (Moestrup, S. K., et al., J. Biol. Chem 268:13691–13696 (1993)). In contrast to the acidic ligand binding region in LRP, its ligands expose regions rich in positively charged amino acid residues (Moestrup, S. K., Biochim. Biophys. Acta 1197:197–213 (1994)). This type of binding and 31 class A repeats present in LRP may be responsible for its wide ligand diversity and ability to serve as a multi-ligand clearance receptor. LRP is expressed in many cell types and tissues including placenta, lung and brain (Moestrup, S. K., et al., *Cell Tissue Res.* 269:375–382 (1992)) and is a major endocytic receptor in the liver (Strickland, D. K., et al., *FASEB J.* 9:890–898 (1995)). A 39 kDa receptor-associated protein (RAP) binds to LRP with high affinity ($K_d$=4 nM (27)) and inhibits binding and LRP-mediated internalization and degradation of all ligands (Moestrup, S. K. *Biochim. Biophys. Acta* 1197:197–213 (1994); Williams, S. E., et al., *J. Biol. Chem.* 267:9035–9040 (1992)), therefore serving as a useful tool for testing whether LRP is involved in endocytosis of a given ligand.

In the present study we demonstrated that fVIII specifically binds to LRP, and that LRP mediates the internalization and subsequent degradation of fVIII in cultured fibroblasts and appears to be responsible for in vivo clearance of fVIII from circulation. We also demonstrated that interaction of the A2 domain of fVIII with LRP is responsible for mediating catabolism of fVIII.

Experimental Procedures

Monoclonal Antibodies. The monoclonal antibodies (mAbs) C4 (epitope within the fVIII light chain residues 1670–1684 (Foster, P. A., et al., *J. Biol. Chem* 263:5230–5234 (1988))), C5 (epitope within A1 residues 351–361) and T5 (epitope within the residues 701–740 (Fulcher, C. A., et al., *J. Clin. Invest.* 76:117–124 (1985))) were kindly provided by Dr. Carol Fulcher (Scripps Clinic and Research Foundation, La Jolla, Calif.). The anti-A2 mAb 8860 was generously provided by Baxter/Hyland. Mab 413 (epitope within A2 domain residues 484–509 (Healey, et al., J. F., *J. Biol. Chem* 270:14505–14509 (1995))) was prepared as described previously (Saenko, E. L., et al., *J. Biol. Chem* 269:11601–11605 (1994)).

Proteins. LRP was isolated from human placenta as described (Ashcom, J. D., et al., *J. Cell Biol.* 110:1041–1048 (1990)). Human RAP was expressed in bacteria and purified as described (Williams, S. E., et al., *J. Biol. Chem.* 267: 9035–9040 (1992)). fVIII was purified from therapeutic concentrates of Method M, American Red Cross (Saenko, E. L., et al., *J. Biol. Chem* 271:27424–27431 (1996)). HCh and LCh were prepared from fVIII as described previously (Saenko, E. L. and Scandella, D., *J. Biol Chem* 272, 18007–18014 (1995)). Purification of the A1/A3-C1-C2 dimer and A2 subunit was performed using ion exchange chromatography of thrombin activated fVIII on a Resource S column (Pharmacia) (Fay, P. T., et al., *J. Biol. Chem* 268, 17861–17866 (1993)). Residual A2 present in the A1/A3-C1-C2 preparation was removed by its passage over an immobilized mAb 8860 column equilibrated in 20 mM Tris, pH 7.4, 0.15 M NaCl, 5 mM CaCl$_2$.

Radiolabeling of fVIII and synthetic peptides. Prior to iodination fVIII and A2 were dialyzed into 0.2 M sodium acetate, 5 mM calcium nitrate, pH 6.8 (iodination buffer). Five µg of fVIII in 30 µl of iodination buffer were added to lactoperoxidase beads (Worthington Biochemical Corp.), 5 µl of Na$^{125}$I (100 mCi/ml, Amersham), and 5 µl of 0.03% H$_2$O$_2$ (Mallincrodt) and incubated for 4 min. Free Na$^{125}$I was removed by chromatography on a PD10 column (Pharmacia). The specific radioactivity of fVIII and A2 was 3.5–5 µCi/µg of protein. The activity of $^{125}$I-fVIII determined in the one-stage clotting assay (3740 units/µg) was similar to that of unlabeled fVIII.

Solid-phase binding assays. Homologous and heterologous ligand displacement assays were performed as previously described (Williams, S. E., et al., *J. Biol. Chem.* 267:9035–9040 (1992)). Microtiter wells were coated with purified LRP or BSA (3 µg/ml) in 50 mM Tr-is, 0.15 M NaCl, pH 8.0, for 16 h and then blocked with 3% BSA in TBS. Coated wells were incubated with $^{125}$I-A2 or $^{125}$I-fVIII in 20 mM Tris-buffered saline pH 7.4, containing 5 mM CaCl$_2$, 0.05% Tween-20 in the presence or absence of unlabeled competitors for 1 h at 37° C. The radioactivity bound to the wells was counted using a γ-counter (Pharmacia). Affinity constants were derived from homologous and heterologous displacement data using the computer program LIGAND (Munson, P T and Rodbard, D. *Anal. Biochem.* 107:220–239 (1980)).

Cell-mediated ligand internalization and degradation assays. A normal mouse embryonic fibroblast line (MEF) and a mouse embryonic fibroblast cell line that is genetically deficient in LRP biosynthesis (PEA 13) were obtained from Dr. Joachim Herz (University of Texas Southwestern Medical Center, Dallas, Tex.) and maintained as described (Willnow, T. E. and Herz, J., *J. Cell Sci.* 107:719–726 (1994)). Cells were seeded at 1×10$^5$ cells/well and allowed to grow for 24 h at 37° C., 5% CO$_2$. Cellular internalization and degradation assays were conducted as described previously (Kounnas, M. Z., et al., *J. Biol. Chem.* 270:9307–9312 (1995)). Internalization and degradation of the $^{125}$I-labeled fVIII and A2 was measured after incubation for indicated time intervals at 37° C. in 0.5 ml of Dulbecco's modified medium (Gibco BRL) containing 2% BSA. Internalization was defined as radioactivity that is resistant to release from cells by trypsin (50 µg/ml) and proteinase K (50 µg/ml) (Sigma) in a buffer containing 5 mM EDTA. This treatment was previously shown to release radioligand bound to cell surface (Kounnas, M. Z., et al., *J. Biol. Chem.* 270:9307–9312 (1995)) and therefore the ligand remained associated with cells after this treatment was considered as internalized. Degradation was defined as radioactivity in the medium that is soluble in 10% trichloroacetic acid. The value of degradation was corrected for non-cellular mediated degradation by subtracting the amount of degradation products generated in parallel wells lacking cells.

Clearance of $^{125}$I-A2 domain and $^{125}$I-fVIII/vWf complex from mouse plasma. The complex of $^{125}$I-labeled fVIII with vWf in the presence or absence of RAP (in a total volume 250 µl) was injected in a tail vein of BALB/C mice over a period of approximately 20 seconds. At selected time intervals following injection (1, 3, 6, and 18 min), blood (50 µl) was withdrawn from the orbital plexus into 10 µl of 100 mM EDTA, and the radioactivity of the aliquot was determined. The percentage of ligand remaining in circulation was calculated considering radioactivity of the aliquot taken at 1 min after injection as 100%. The clearance of each preparation was examined in two mice and the results were averaged. At the end of experiment, animals were sacrificed, liver lobules and kidneys were excised and weighed, followed by measuring the radioactivity in these tissues.

Results

Figure 15A:
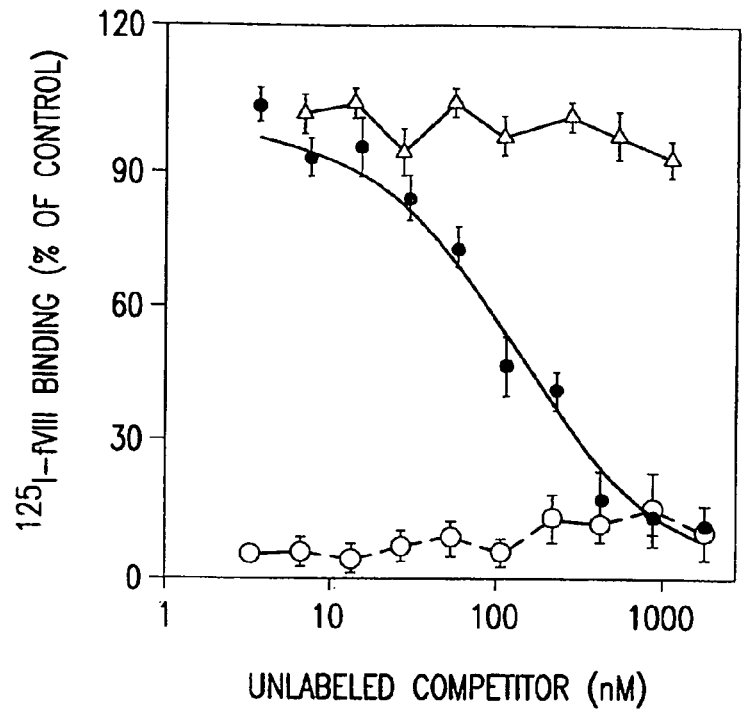
FIGS. 15A–15B. Binding of $^{125}$I-fVIII to purified LRP by ligand competition assay. $^{125}$I-fVIII (1 nM) was incubated for 1 h at 37° C. in wells coated with LRP (●) or BSA (○) in the presence of increasing concentrations of unlabeled competitors, fVIII (●, ○) or vWf (Δ) (FIG. 15A) and RAP (●, ○) (FIG. 15B). In the experiment (Δ), $^{125}$I-fVIII was preincubated with vWf for 30 min at 37° C., prior to its addition to the wells. Following incubation, the wells were washed and $^{125}$I-fVIII binding was determined. Binding of $^{125}$I-fVIII in the presence of unlabeled fVIII, vWf, or RAP is expressed as the percentage of $^{125}$fVIII binding, when no competitor was added. Each point represents the mean value of triplicates and the error bars display the standard deviation. The curves show a best fit of the data to a model describing heterologous ligand displacement from a single class of binding sites using the program LIGAND.

Factor VIII binds to LRP and its binding is prevented by RAP. The ability of fVIII to bind to LRP in vitro was examined in homologous displacement binding assay. In the assay, binding of $^{125}$I-fVIII (1 nM) to purified LRP, but not to BSA-coated wells, was competed (>90%) by an excess of unlabeled fVIII (FIG. 15A). The quantitative data regarding fVIII interaction with LRP were derived from the homologous displacement of $^{125}$I-fVIII by unlabeled fVIII, which was adequately described by a model containing a single class of fVIII binding sites with $K_d$ of 116 nM. To elucidate whether fVIII in a complex with vWf is also able to bind to LRP, we tested the effect of vWf on $^{125}$I-fVIII binding to immobilized LRP. In this experiment, $^{125}$I-fVIII was preincubated with vWf for 30 min at 37° C. to allow complex formation prior to its addition to LRP coated wells. As shown in FIG. 15A, $^{125}$I-fVIII binding to LRP was not inhibited by vWf up to the concentration of 1000 nM, which is 20-fold higher than its concentration in plasma (50 mM (Vlot, A. J., et al., Blood 85:3150–3157 (1995))). This indicates that the complex formation with vWf does not affect fVIII ability to bind to LRP.

Figure 15B:
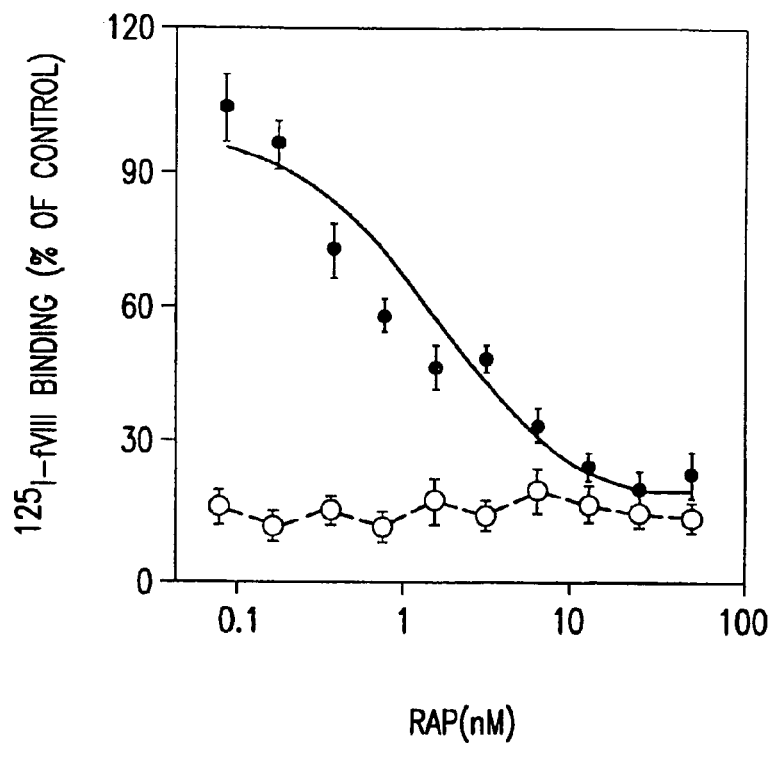

RAP, the antagonist of LRP-ligand binding, completely inhibited the binding of $^{125}$I-fVIII to LRP-coated wells with $K_i$ of 2.5 nM (FIG. 15B), a value similar to the previously determined affinity (4 nM) of RAP for LRP (Strickland, D. K., et al., J. Biol. Chem. 265:17401–17404 (1990)). Together, these results demonstrate specific fVIII binding to LRP.

Figure 16:
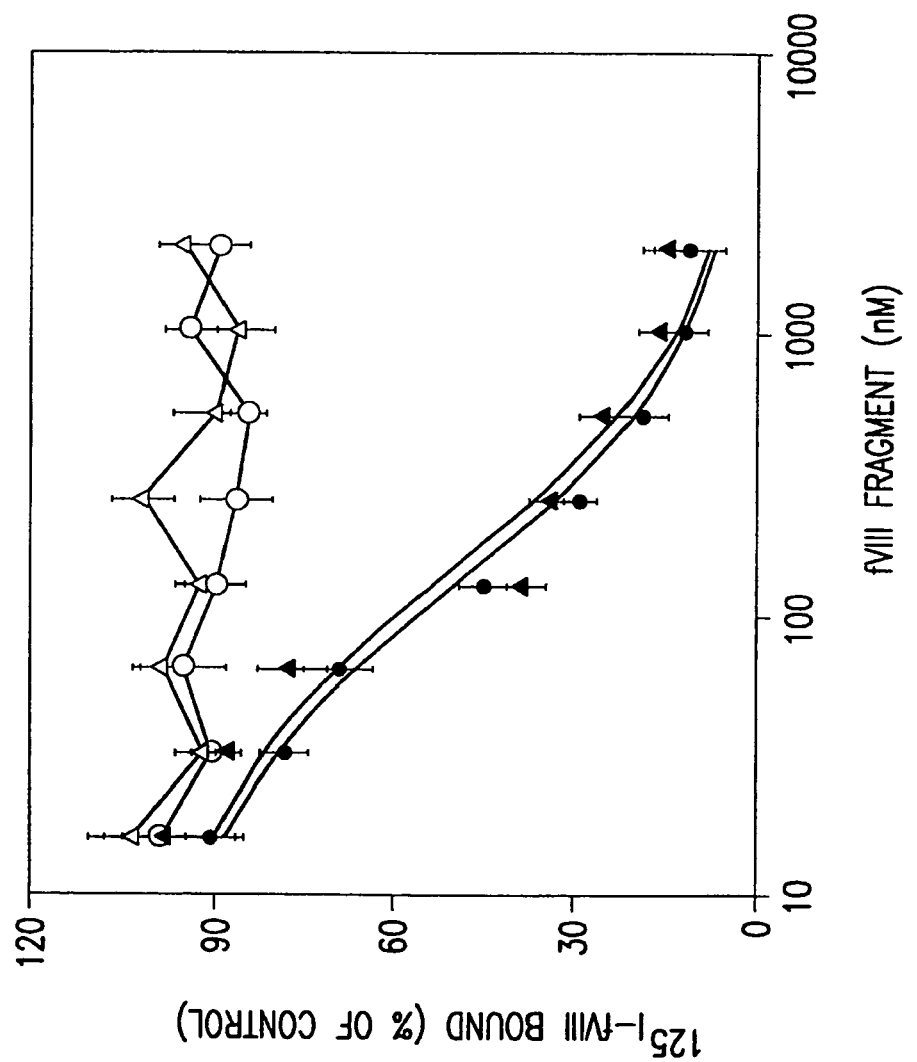
FIG. 16. Effect of fragments of fVIII on its binding to LRP. $^{125}$fVIII (1 nM) and increasing concentrations of unlabeled HCh (●), A2 (▲), LCh (○) or A1/A3-C1-C2 (Δ) were incubated with LRP as described in FIG. 15. Each point represents the mean value and the standard deviation of the triplicates. The data were fitted as in FIGS. 15A–15B to a model describing heterologous ligand displacement from a single class of binding sites with $K_i$ values of 120 and 132 nM for HCh and A2, respectively.

The amino acid residues 484–509 within the fVIII A2 domain are responsible for fVIII binding to purified LRP. In order to localize fVIII region(s) involved in interaction with LRP, binding between $^{125}$I-fVIII and immobilized LRP was competed by unlabeled fVIII fragments. As shown in FIG. 16, HCh and A2 domain of fVIII, but not LCh (AR-A3-C1-C2) or A1/A3-C1-C2 dimer, displaced $^{125}$I-fVIII from LRP in the heterologous ligand displacement assay. The $K_i$ values determined for the HCh and A2 were similar, 120 nM and 132 nM, respectively. The similarity of the above $K_d$ value for fVIII binding to LRP and the $K_i$ value for inhibition of this binding by isolated A2 subunit indicates that A2 domain of HCh is responsible for fVIII binding to LRP.

Figure 17A:
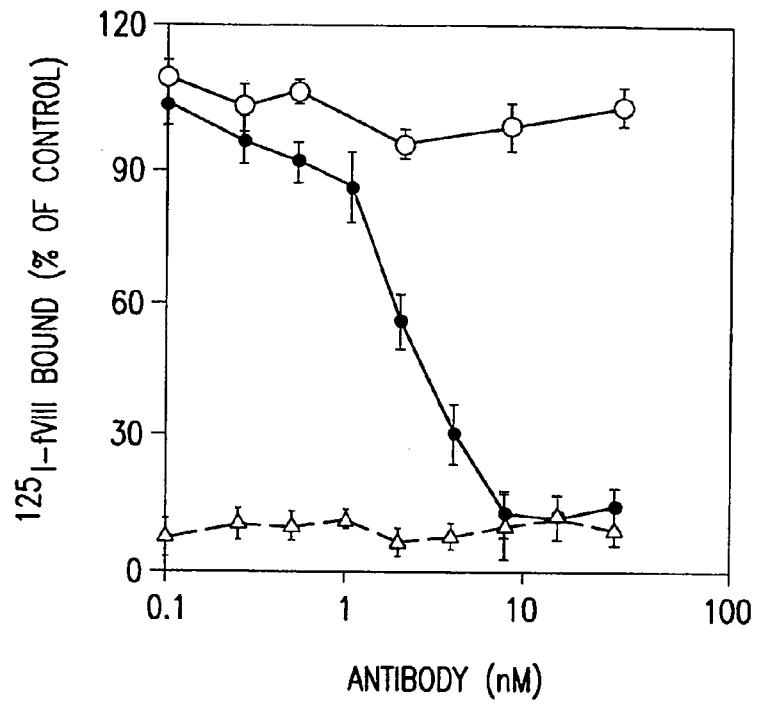
FIGS. 17A–17B. Effect of monoclonal antibodies and synthetic peptides on $^{125}$fVIII binding to purified LRP.

To localize the region of the A2 domain responsible for the interaction with LRP, we tested the effect of anti-A2 monoclonal antibodies with known epitopes on fVIII/LRP binding. FIG. 17A shows that mAb 413 (epitope within the A2 domain residues 484–509 (Healey, J. F., et al., J. Biol. Chem 270:14505–14509 (1995))) but not mAb T5 (epitope within the A2 domain residues 701–740 (Fulcher, C. A., et al., J. Clin. Invest. 76:117–124 (1985))) is able to block fVIII/LRP interaction. The concentration of mAb 413 required for 50% inhibition of $^{125}$I-fVIII/LRP binding was 2.5 nM. The low molar excess (2.5-fold) of mAb 413 over fVIII required for 50% inhibition of fVIII/LRP binding is consistent with a previously reported high affinity of mAb 413 for fVIII (Lollar, P., et al., J. Clin. Invest. 93:2497–2504 (1994)). In a control experiment, mAbs C5 (epitope within A1 residues 351–361) and C4 (epitope within LCh residues 1670–1684 (Foster, P. A., et al., J. Biol. Chem 263:5230–5234 (1988))) did not have any effect on fVIII binding to LRP (data not shown), which is consistent with the lack of participation of A1 and LCh in fVIII binding to LRP.

Figure 17B:
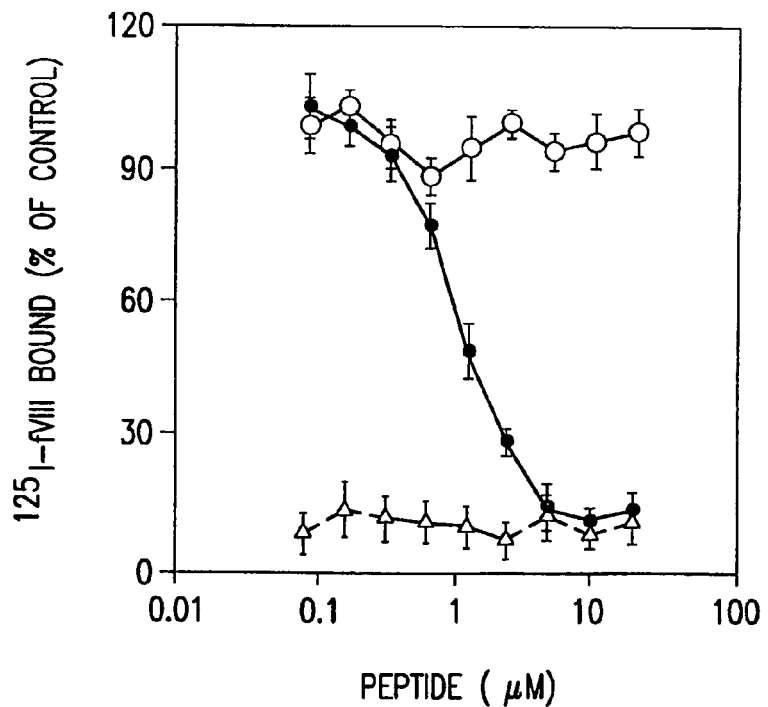

Since it was previously demonstrated that mAb 413 recognizes synthetic peptide with a human fVIII sequence 484–509 (Healey, J. F., et al., J. Biol. Chem 270:14505–14509 (1995)), we tested if the region of the A2 domain encompassed by peptide 484–509 is involved in binding to LRP. As seen from FIG. 17B, the synthetic peptide 484–509, but not the control A2 peptide 432–456, inhibited fVIII binding to LRP in a dose-dependent fashion, indicating that the region 484–509 of the A2 domain contains important residues for fVIII binding to LRP. In a control experiment, no binding of $^{125}$I-fVIII to BSA-coated wells was observed in the presence of peptide 484–509 (FIG. 17B).

Figure 18A:
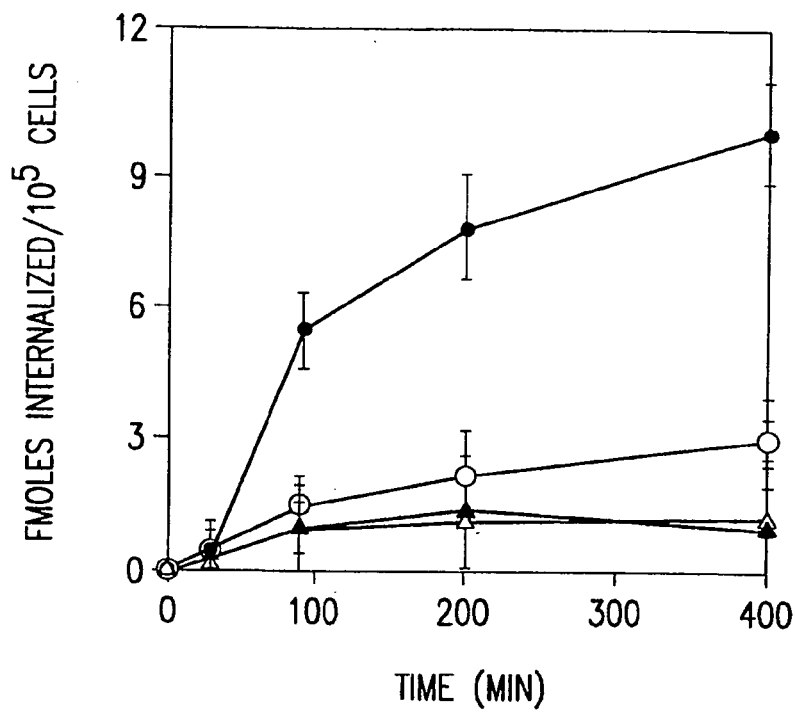
FIGS. 18A–18B. Internalization and degradation of $^{125}$I-fVIII/vWf complex by LRP-expressing (MEF) and LRP-deficient (PEA 13) fibroblasts. Wells containing 2×10$^5$ of each MEF (○, ●) or PEA 13 cells (Δ, ▲) were incubated with 1 nM $^{125}$I-fVIII/vWf in the absence (closed symbols) or presence (opened symbols) of RAP (1 μM). $^{125}$I-fVIII/vWf complex was prepared by incubation of $^{125}$I-fVIII with unlabeled vWf at a molar ratio 1:50 for 30 min at 37° C. At the indicated times, the amounts of internalized $^{125}$I-fVIII (FIG. 18A) and degraded $^{125}$I-fVIII (FIG. 18B) by the MEF and PEA 13 fibroblasts were determined as described under Experimental Procedures of Example 2. In the experiment (∇), degradation of $^{125}$I-fVIII (1 nM) by MEF cells in the presence of (0.1 mM) chloroquine is shown. Each data point represents the mean and standard deviation of duplicate determinations.
Figure 18B:
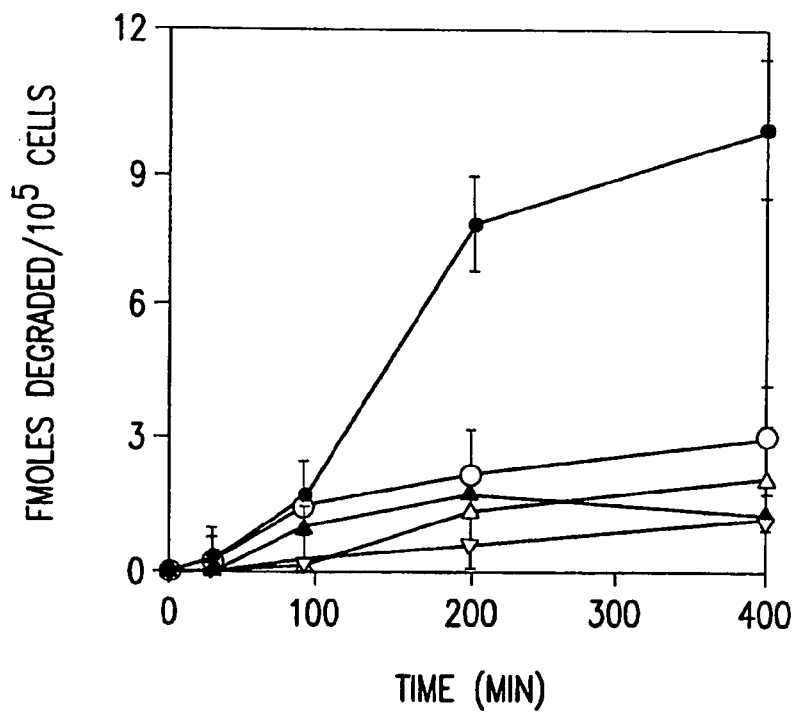

Internalization and degradation of $^{125}$I-fVIII complex with vWf by cultured fibroblasts is mediated by LRP. Since the data presented above demonstrated specific interaction between fVIII and LRP, and vWf does not interfere with this interaction, we hypothesized that LRP may be also capable of mediating the cellular internalization of $^{125}$I-fVIII from its complex with vWf. To examine this hypothesis, cellular uptake and degradation experiments were conducted in mouse embryonal fibroblasts (MEF) which express LRP and in PEA 13 fibroblasts that are genetically deficient in LRP (Willnow, T. E. and Herz, J. J. Cell Sci. 107:719–726 (1994)). The $^{125}$I-fVIII/vWf complex was prepared by 30 min (37° C.) incubation of $^{125}$I-fVIII with vWf at their plasma concentrations of 1 nM and 50 nM, respectively. As shown in FIGS. 18A–18B, MEF cells, but not PEA 13 cells lacking LRP, were capable of internalizing and degrading $^{125}$I-fVIII in the presence of vWf. Further, internalization and degradation of $^{125}$I-fVIII by MEF but not by PEA 13 fibroblasts was inhibited by RAP, an antagonist of ligand binding to LRP. The ability of RAP to block the uptake and degradation of $^{125}$I-fVIII/vWf in MEF cells and inability of PEA 13 cells to efficiently mediate uptake and degradation indicates that LRP is the mediator of $^{125}$I-fVIII/vWf catabolism. To further characterize the degradation pathway of fVIII in the MEF cells, we tested the effect of chloroquine (an agent that blocks lysosomal degradation) on $^{125}$I-fVIII degradation. As seen from FIG. 18B, the degradation of $^{125}$I-fVIII is completely inhibited by chloroquine.

Figure 19A:
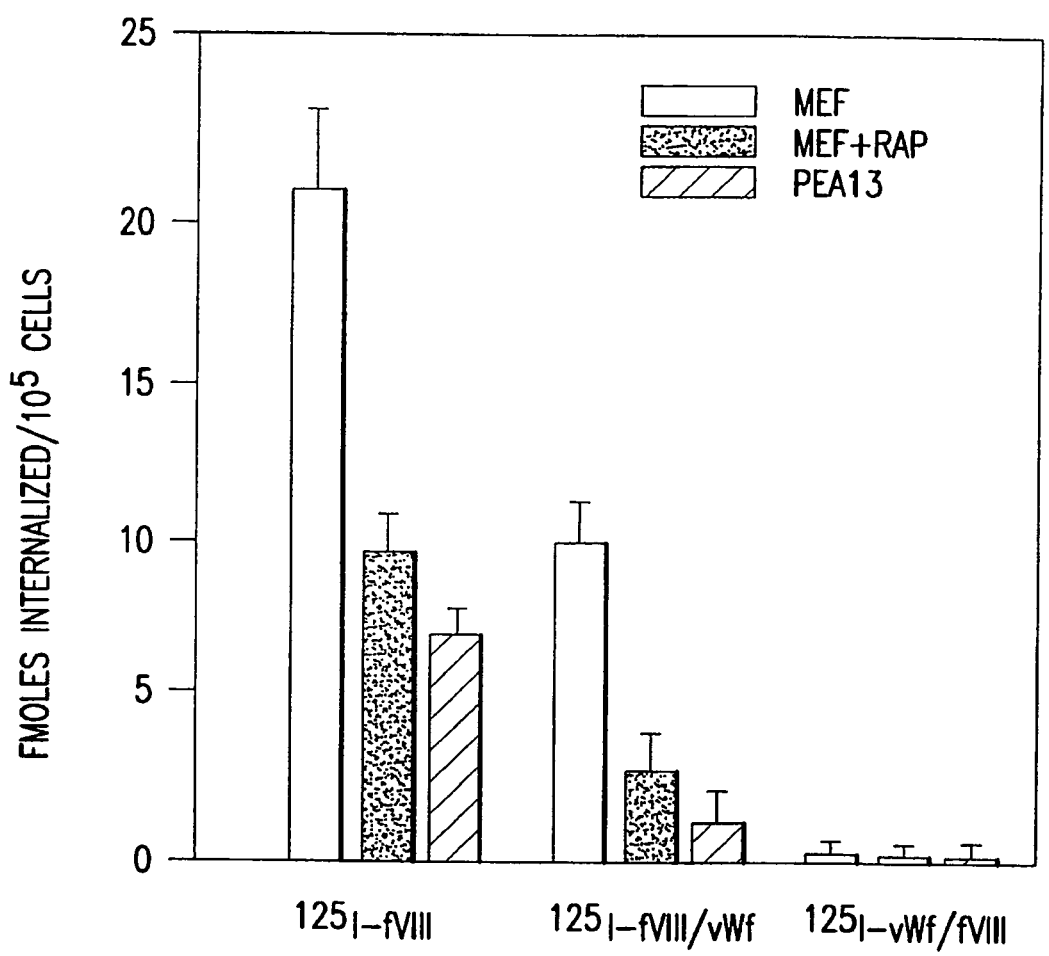
FIGS. 19A–19B. Comparison of internalization of isolated $^{125}$I-fVIII and components of fVIII/vWf complex. Wells containing 2×10$^5$ of each MEF and PEA 13 cells were incubated with 1 nM of isolated $^{125}$I-fVIII or 1 nM of fVIII/vWf complex formed by mixing either $^{125}$I-fVIII (1 nM) with unlabeled vWf (50 nM) or $^{125}$I-vWf (50 nM) with unlabeled fVIII (1 nM). Following incubation for 6 hours with MEF cells in the absence of RAP (open bars) or in the presence of 1 μM RAP (solid bars) or after incubation with PEA 13 cells (hatched bars) the amounts of internalized (FIG. 19A) and degraded (FIG. 19B) isolated $^{125}$I-fVIII, and $^{125}$I-fVIII or $^{125}$I-vWf from the fVIII/vWf complex were determined as described in FIGS. 18A–18B. The data shown are an average of duplicate determinations ±standard deviation.
Figure 19B:
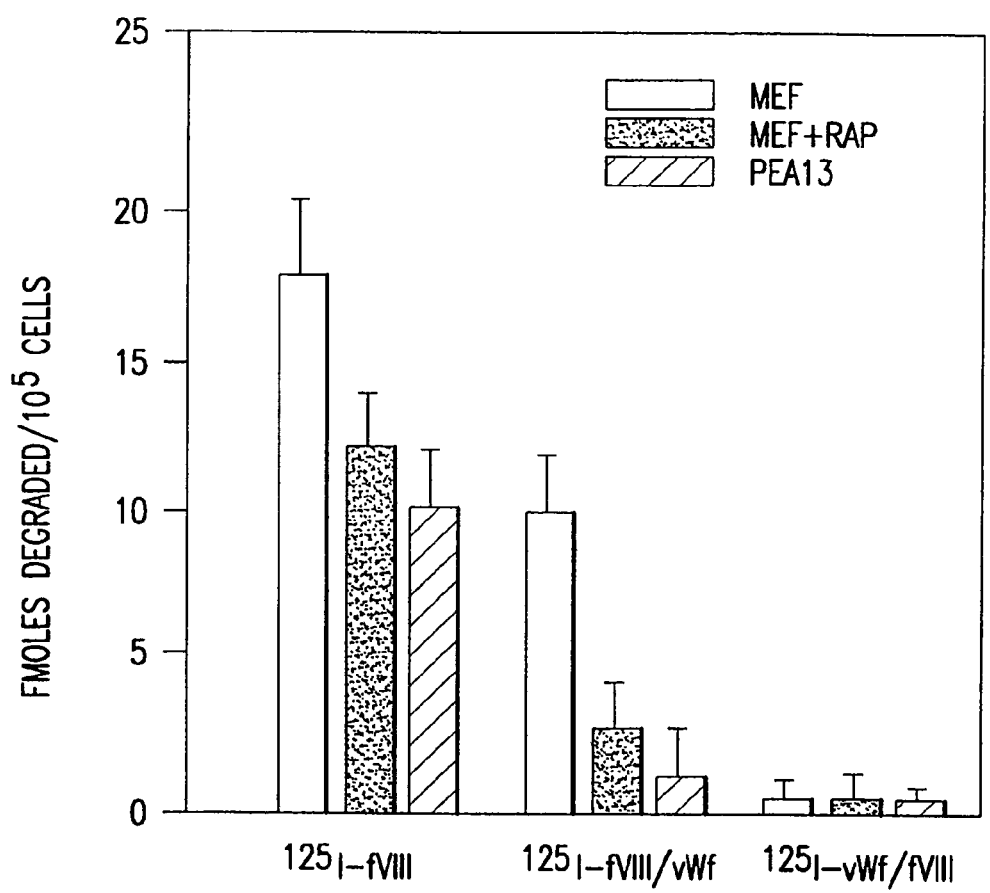

To elucidate if fVIII internalization in the absence of vWf is also mediated by LRP, we measured the internalization and degradation of isolated $^{125}$I-fVIII (FIGS. 19A–19B). As seen from FIGS. 19A–19B, both internalization and degradation of isolated $^{125}$I-fVIII by MEF fibroblasts is approximately 2-fold higher than that in the presence of vWf. RAP inhibited the internalization and degradation of $^{125}$I-fVIII to a lesser degree than those of $^{125}$I-fVIII/vWf complex and, in addition, LRP-deficient PEA 13 fibroblasts were able to internalize and degrade isolated $^{125}$I-fVIII. This indicates that the LRP-mediated pathway is not the sole mechanism of fVIII internalization and degradation in the absence of vWf.

To determine whether vWf bound to fVIII is also internalized and degraded by MEF cells, internalization and degradation of $^{125}$I-labeled vWf complexed with fVIII was measured. As shown in FIGS. 19A–19B, the amounts of internalized and degraded $^{125}$I-vWf by both MEF and PEA 13 cells were less than 5% of the corresponding amounts of $^{125}$I-fVIII catabolized from its complex with vWf under the same experimental conditions. This indicates that vWf does not follow fVIII in the LRP-mediated pathway and possibly dissociates from fVIII at an early stage of endocytosis, prior to entry of the complex into endosomal compartments.

Figure 20A:
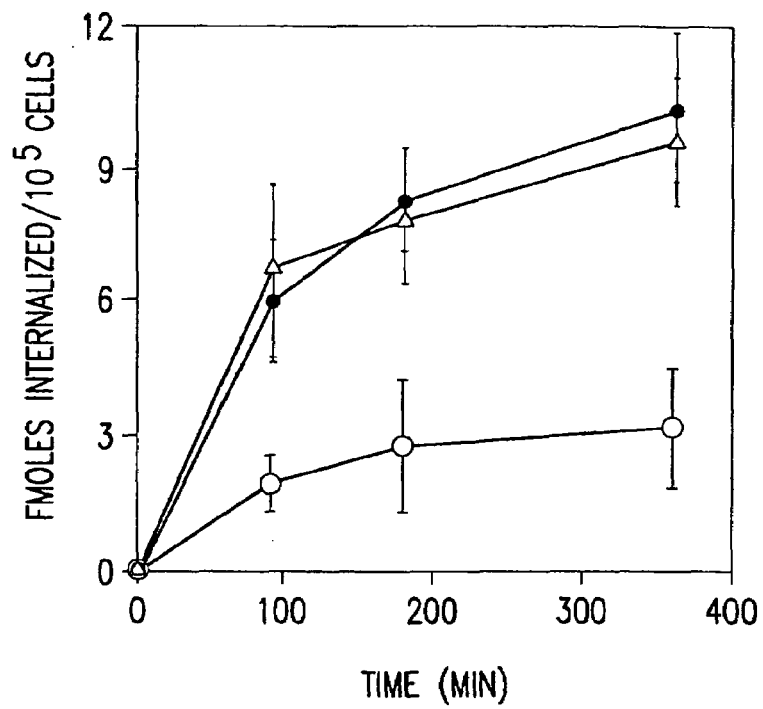
FIGS. 20A–20B. The A2 domain of fVIII inhibits the internalization and degradation of $^{125}$I-fVIII/vWf complex by MEF fibroblasts. One nM of $^{125}$I-fVIII/vWf complex was prepared as in FIGS. 18A–18B and incubated with 2×10$^5$ of MEF cells in presence of 1 μM of A2 (○), 1 μM of A1/A3-C1-C2 (Δ), or in the absence of any competitor (●). At the indicated times, the amounts of internalized (FIG. 20A) and degraded $^{125}$I-fVIII (FIG. 20B) were determined as in FIGS. 18A–18B. Each data point represents the mean and standard deviation of duplicate determinations.
Figure 20B:
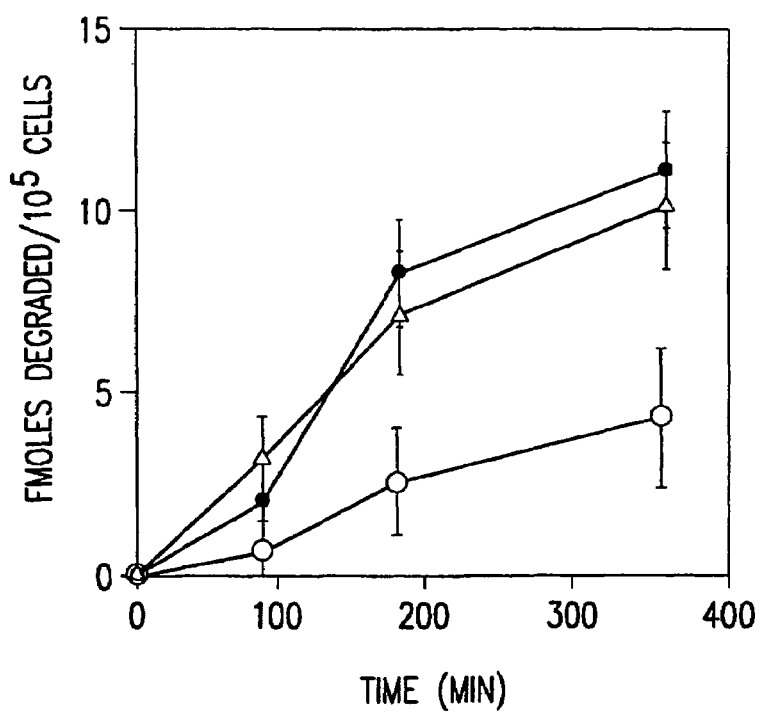

The A2 subunit of fVIII inhibits endocytosis and degradation of $^{125}$I-fVIII/vWf by MEF cells. Since we have demonstrated above that the A2 subunit of fVIII prevents an in vitro interaction between LRP and fVIII, we examined if A2 can also inhibit LRP-mediated internalization and degradation of fVIII/vWf complex by MEF cells. FIGS. 20A–20B demonstrate that a 1000-fold excess of A2 subunit over $^{125}$I-fVIII/vWf complex effectively inhibit internalization (by >70% after 4 hours) and degradation (by >60% after 4 hours) of this complex. In contrast, A1/A3-C1-C2 heterodimer, which did not inhibit fVIII interaction with purified LRP in the above experiments, did not have any effect on $^{125}$I-fVIII endocytosis and degradation by MEF cells (FIGS. 20A–20B).

Figure 21A:
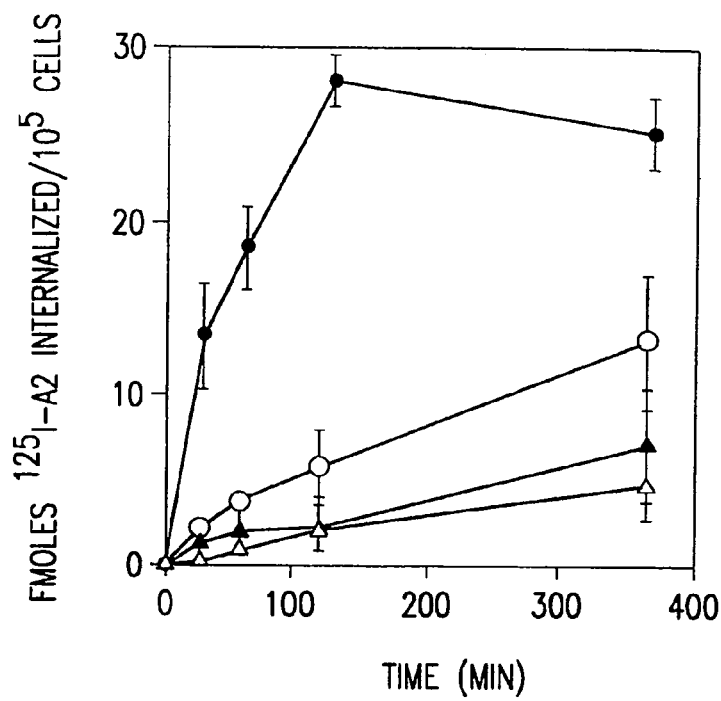
FIGS. 21A–D. Internalization and degradation of $^{125}$I-A2 by MEF fibroblasts and by LRP-expressing smooth muscle cells (SMC) and alveolar epithelial cells (T2).
Figure 21B:
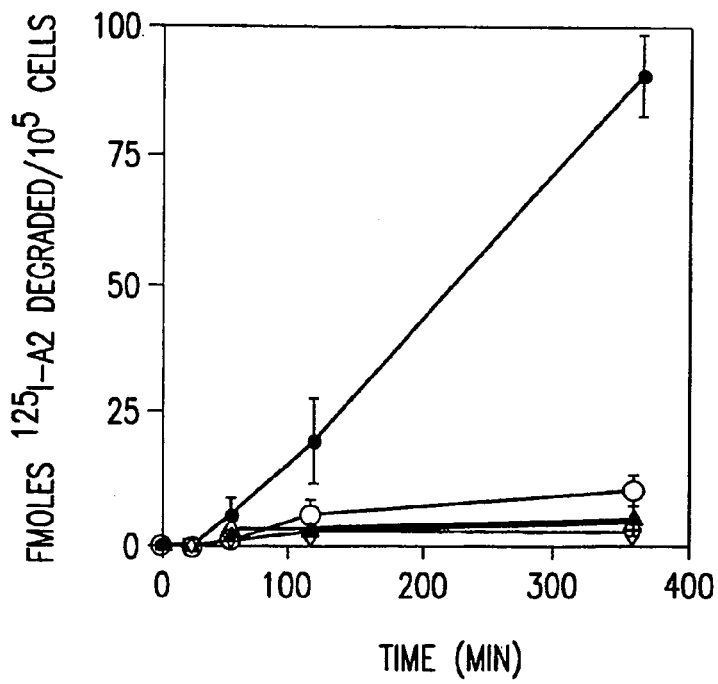
Figure 21C:
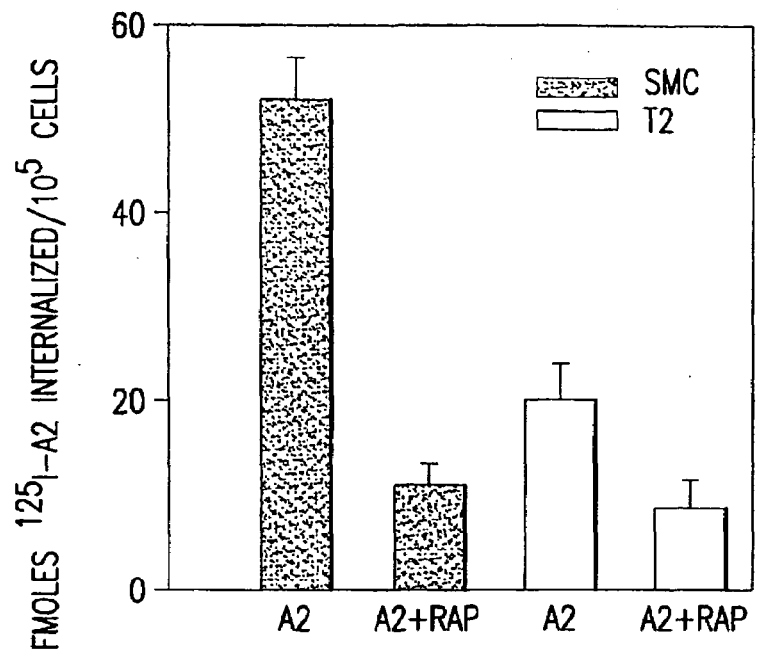
Figure 21D:
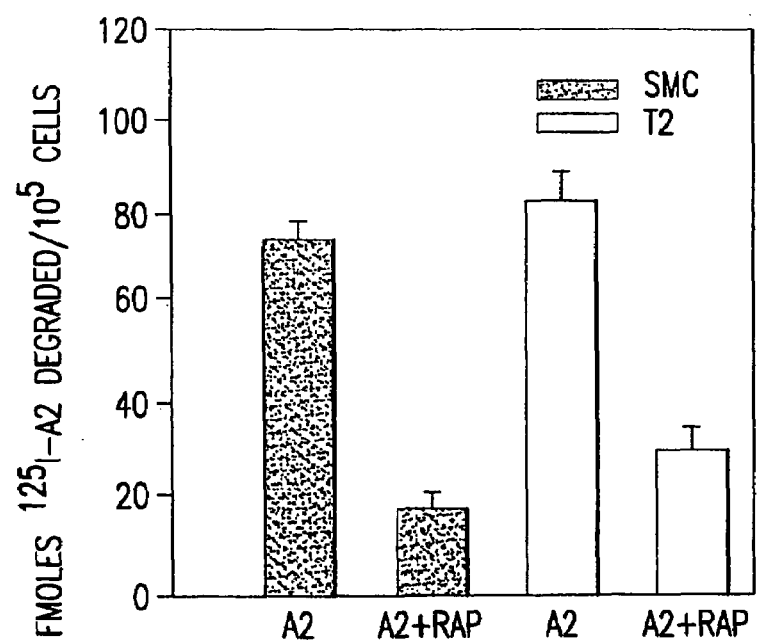

To confirm that the inhibitory effect of the A2 subunit results from its direct competition with $^{125}$I-fVIII/vWf complex for LRP-mediated internalization and degradation, we tested whether MEF cells are able to internalize and degrade isolated A2 subunit. As shown in FIGS. 21A–21B, $^{125}$I-A2 is readily internalized and degraded by LRP-expressing MEF cells. Both the internalization and degradation of the $^{125}$I-labeled A2 were blocked in the presence of RAP. In contrast, LRP-deficient PEA 13 cells were unable to internalize or degrade $^{125}$I-A2 (FIGS. 21A–21B), confirming that catabolism of the A2 subunit is LRP-mediated.

To verify that LRP-mediated internalization and degradation of the A2 domain was not the unique feature of the MEF cells, we tested $^{125}$I-labeled A2 internalization and degradation by smooth muscle cells (SMC) and alveolar epithelial cells (T2), which also express LRP on their surfaces (Moestrup, S. K., *Cell Tissue Res.* 269:375–382 (1992)). As shown in FIGS. 11C and D, RAP effectively inhibited both internalization of $^{125}$I-A2 by SMC and T2 (by 81% and 64%, respectively), and its degradation (by 78% and 68%), indicating that these processes were mediated by LRP.

Thus, the data shown in FIGS. 20A–20B and 21A–21B demonstrate that LRP is capable of binding fVIII via its A2 domain and of mediating fVIII endocytosis leading to lysosomal degradation.

Figure 22A:
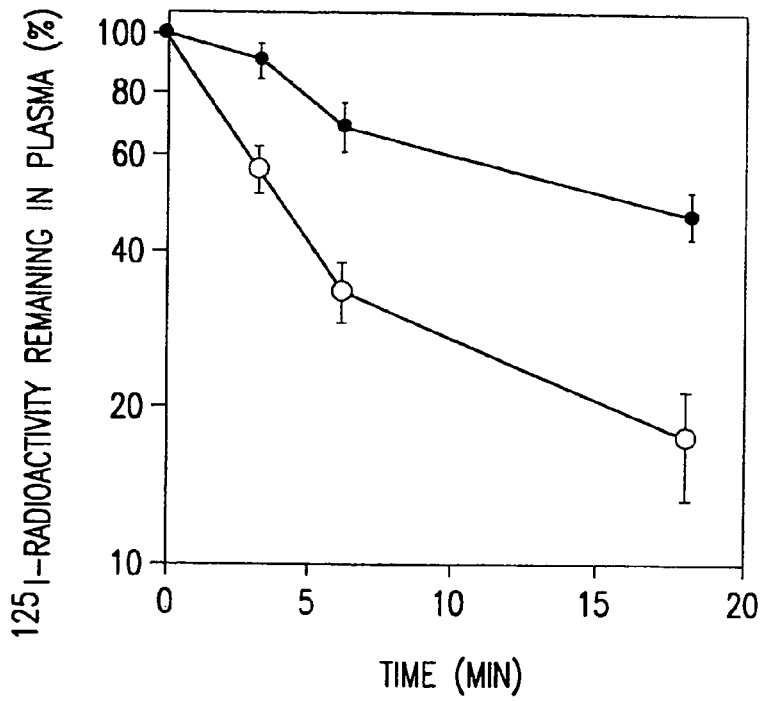
FIGS. 22A–22B. The effect of RAP on clearance of $^{125}$I-A2 (A) or $^{125}$I-fVIII/vWf (B) from plasma of mice. BALB/c mice were injected into the tail vein by sample containing $^{125}$I-A2 (36 nM) (FIG. 22A) or $^{125}$I-fVIII/vWf (20 nM) (FIG. 22B) in the absence (●) or presence (○) of RAP (267 μM). At indicated time points, blood (50 μl) was collected into 10 μl of 100 mM EDTA and an aliquot (50 μl) was counted for radioactivity. The percentage of ligand remaining in circulation was calculated considering radioactivity of the aliquot taken at 1 min after injection as 100%. The clearance of each preparation was examined in two mice, and the data plotted represent the average value ±standard deviation.
Figure 22B:
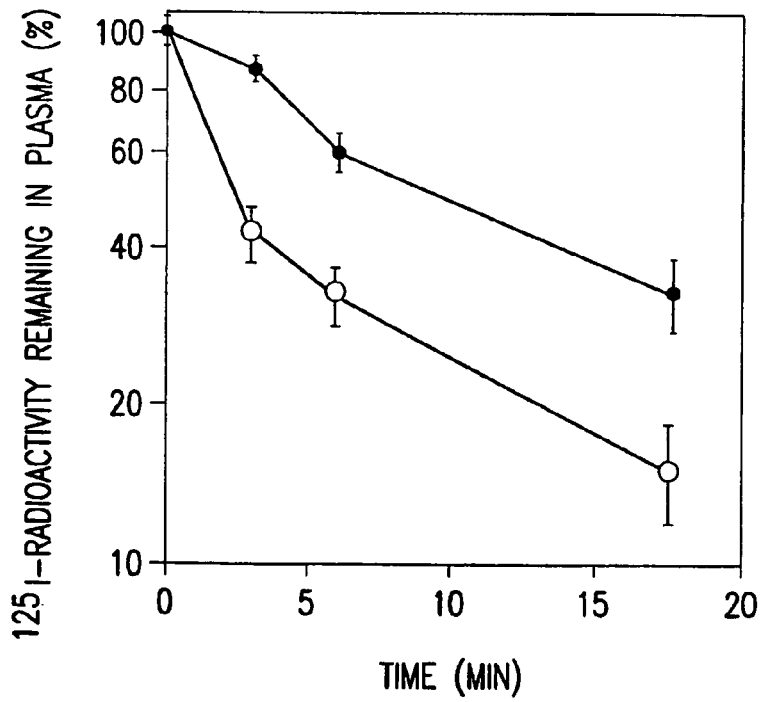

Effect of RAP on the plasma clearance of $^{125}$I-fVIII and $^{125}$I-A2. To determine whether LRP is capable of catabolizing the isolated fVIII A2 subunit and whole fVIII from its complex with vWf in vivo, the effect of RAP on the clearance rates in mice of $^{125}$I-fVIII/vWf complex and $^{125}$I-A2 was tested. As shown in FIG. 22A, RAP increased the half-life of both $^{125}$I-A2 and $^{125}$I-fVIII in mouse plasma by approximately 4 and 2.5-fold, respectively. In addition, in the absence of RAP, most of radioactivity was found in the liver but not in kidney, consistent with LRP presence in high abundance in hepatic tissues (Strickland, D. K., et al., *FASEB J.* 9:890–898 (1995)). Thus, our data show that a RAP-sensitive hepatic receptor, LRP, plays a major role in the removal of fVIII and its A2 subunit from circulation.

Discussion

In the present study we demonstrated that LRP mediates the internalization and degradation of human fVIII in a model system using LRP-expressing cells and that it is responsible for fVIII clearance in vivo. This conclusion is based on several independent observations. First, we found that fVIII directly binds to purified LRP immobilized on microtiter wells, and that this binding is competed by RAP, an antagonist of ligand binding to LRP. Second, $^{125}$I-fVIII, is internalized from its complex with vWf by mouse fibroblasts expressing LRP (MEF cells), but not by mouse fibroblasts genetically deficient in LRP (PEA 13 cells). Third, we demonstrated that RAP effectively inhibited the cellular uptake and degradation of $^{125}$I-fVIII from its complex with vWf by MEF cells and the in vivo clearance of $^{125}$I-fVIII from circulation in mice.

Our studies revealed that the A2 domain of fVIII is responsible for its interaction with LRP, since only A2 domain and HCh, which contains the A2 domain, were able to inhibit the interaction of $^{125}$I-fVIII with LRP in a purified system. Thus, it was concluded that A2 is responsible for fVIII binding to LRP. Based on the observation that vWf did not inhibit fVIII binding to LRP, we proposed that LRP may internalize fVIII from its complex with vWf. Indeed, mouse embryonic fibroblasts (MEF) that express LRP, but not fibroblasts genetically deficient in LRP, were able to internalize and degrade $^{125}$I-fVIII in the presence of vWf. These processes were competed by RAP and the A2 subunit of fVIII, indicating that cellular internalization and degradation were mediated by the interaction of the A2 domain of fVIII with LRP. The physiological relevance of the observations utilizing the LRP-expressing cell model system was supported by in vivo clearance studies of $^{125}$I-fVIII/vWf complex in mice which demonstrated that RAP prolonged the half-life of $^{125}$I-fVIII in circulation by 2.5-fold, indicating that a RAP-sensitive receptor, most likely LRP, is responsible for the clearance of fVIII from plasma.

Further localization of the region in the A2 domain responsible for binding to purified LRP was initiated by the finding that a monoclonal antibody with an epitope within A2 domain residues 484–509 completely inhibited fVIII interaction with LRP. Inhibition of fVIII/LRP binding by synthetic peptide with a human fVIII sequence 484–509 indicated that the region of the A2 domain is likely to be directly involved in fVIII binding to purified LRP.

The region 484–509 contains 6 positively charged residues, Lys at positions 493, 496 and 499 and Arg at positions 484, 489 and 490. Basic residues in lipoprotein lipase (Chappell, D. A., et al., *J. Biol. Chem.* 268:14168–14175 (1993)), u-PA-PAI-1 complex (Rodenburg, K. W., et al., *Biochem. J.* 329:55–63 (1998)), and $\alpha_2$-macroglobulin (Howard, G. C., et al., *J. Biol. Chem* 271:14105–14111 (1996)) were previously shown to be critical for electrostatic interaction with LRP. Alanine substitution of the basic amino acid residues in lipoprotein lipase (Williams, S. E., et al., *J. Biol. Chem.* 269:8653–8658 (1994)), u-PA/PAI-I complex (Rodenburg, K. W., et al., *Biochem. J.* 329:55–63 (1998)) and in the receptor binding fragment from $\alpha_2$-macroglobulin (Howard, G. C., et al., *J. Biol. Chem* 271: 14105–14111 (1996)) lead to a considerable reduction of affinity for ligand binding to LRP and partial (Rodenburg, K. W., et al., *Biochem. J.* 329:55–63 (1998)) or complete (Howard, G. C., et al., *J. Biol. Chem* 271:14105–14111 (1996)) inhibition of internalization and degradation of the mutants. Therefore, Ala or other amino acid substitutions within the 484–509 region of the recombinant fVIII are useful for reduction of the rate of its LRP-mediated endocytosis and generation of the fVIII mutants with a longer life in the circulation.

FVIII binds to purified LRP with an affinity of 116 nM, which is much lower than the concentration of fVIII/vWf complex in plasma (1 nM; Wion, K., et al., *Nature* 317: 726–730 (1985)). FVIII affinity for LRP is similar to that of the complexes of serine proteases with inhibitors such as ATIII/thrombin (Kounnas, M. Z., et al., *J. Biol. Chem.* 271:6523–6529 (1996)), HCII/thrombin and $\alpha_1$-antitrypsin/trypsin (Kounnas, M. Z., et al., *J. Biol. Chem.* 271:6523–6529 (1996)), which also bind to LRP with affinities of 80–120 nM, and weaker than measured for other LRP ligands. It was shown (Kounnas, M. Z., et al., *J. Biol. Chem.* 271:6523–6529 (1996)) that internalization and degradation of the above low affinity LRP ligands at their 1 nM concentration by MEF cells occur at a lower rate than that of the u-PA/PAI-I complex which binds to LRP with high affinity ($K_d$<1 nM). Therefore, relatively low affinity of fVIII for LRP is responsible for a slow rate of fVIII internalization and degradation by MEF cells, which is comparable to the rate of ATIII/thrombin, HCII/thrombin and $\alpha$1-antitrypsin/trypsin degradation at 1 nM concentration of each ligand. The low affinity of fVIII for LRP may also be a necessary requirement for the relatively long fVIII half-life (12–14 h) in plasma of normal individuals (Over, J., et al., *J. Clin. Invest.* 62:223–234 (1978)). Alternatively, the low fVIII affinity for LRP may be compensated by concentration of fVIII molecules on the membrane of LRP-expressing cells, for example, via interaction with cell-surface proteoglycans which have been shown to facilitate the uptake of a number of LRP ligands including lipoprotein lipase (Chappell, D. A., et al., *J. Biol. Chem.* 268:14168–14175 (1993)), hepatic lipase (Kounnas, M. Z., et al., *J. Biol. Chem.* 270:9307–9312 (1995)), and thrombospondin (Mikhailenko, I., et al., *J. Biol.*

Chem. 270:9543–9549 (1995); Mikhailenko, I., et al., *J. Biol. Chem.* 272:6784–6791 (1997)).

We found that internalization and degradation of isolated fVIII by MEF cells was greater than the corresponding processes for fVIII bound to vWf. In addition, catabolism of the isolated fVIII by MEF cells was only partially inhibited by RAP, indicating that LRP-mediated endocytosis of fVIII is not the sole mechanism of fVIII clearance in the absence of vWf. Our data suggest that in the presence of vWf, which blocks C2 domain-mediated fVIII binding to phospholipid membranes (Saenko, E. L. and Scandella, D., *J. Biol. Chem* 270:13826–13833 (1995)), fVIII binds only to LRP, whereas in the absence of vWf, fVIII binds both to LRP and to an unidentified cell membrane component. The latter binding may lead to fVIII internalization via a RAP-independent pathway, which may be mediated by unidentified receptor as it was previously proposed for hepatic lipase (Kounnas, M. Z., et al., *J. Biol. Chem.* 270:9307–9312 (1995)). Since we found that $^{125}$I-vWf is not internalized by MEF cells, we propose a model for fVIII endocytosis where fVIII/vWf complex binds to LRP and then vWf dissociates from fVIII during the early stage of fVIII endocytosis, i.e. during the formation of coated pits. Since the half-life for the dissociation of fVIII/vWf complex is about 1 hour (Saenko, E. L. and Scandella, D., *J. Biol Chem* 272, 18007–18014 (1995)), vWf may delay LRP-mediated endocytosis of fVIII according to the proposed model.

Faster catabolism of fVIII in the absence of vWf is consistent with a demonstrated shorter half-life of fVIII in patients with severe von Willebrand disease (vWD) lacking plasma vWf than that in hemophilia A patients, who have normal levels of vWf (Morfini, M., et al., *Thromb. Haemostas.* 70:270–272 (1993); Lethagen, S., et al., *Ann. Hematol.* 65:253–259 (1992)). Moreover, the half-life of fVIII in vWD patients was prolonged by the presence of vWf in the infused fVIII preparation (Lethagen, S., et al., *Ann. Hematol.* 65:253–259 (1992)). The above observations were previously explained by vWf-mediated stabilization of fVIII by binding to vWf (Wise, R. J., et al., *J. Biol. Chem.* 266: 21948–21955 (1991)) and via secondary vWf-mediated release of endogenous fVIII (Wise, R. J., et al., *J. Biol. Chem.* 266:21948–21955 (1991); Kaufman, R. J., *Mol. Cell. Biol.* 9:1233–1242 (1989)). Our data suggest that in addition to the above effects, vWf may reduce the rate of fVIII clearance by preventing a LRP-independent pathway and limiting fVIII clearance to a LRP-mediated pathway.

The activity of the factor X activation complex (factor Xase), consisting of membrane-bound activated fVIIIa and factor IXa, can be down regulated by inactivation of fVIIIa. The latter occurs via proteolytic degradation of fVIII by activated protein C, factor Xa and factor IXa, and via spontaneous but reversible dissociation of the A2 subunit from fVIIIa heterotrimer (Fay, P. J. and Smudzin, T. M., *J. Biol. Chem* 267:13246–13250 (1992)). Dissociation of the fVIIIa heterotrimer may be accelerated by LRP mediated internalization of the A2 domain, and therefore complement regulation of fVIIIa activity at the sites of coagulation. This hypothesis is supported by the availability of LRP at these sites, since LRP is exposed on the surface of monocytes and macrophages (Moestrup, S. K., et al., *Exp. Cell. Res.* 190: 195–203 (1990); Moestrup, S. K., et al., *Cell Tissue Res.* 269:375–382 (1992)) and upon vascular injury on fibroblasts and smooth muscle cells (Moestrup, S. K., et al., *Cell Tissue Res.* 269:375–382 (1992)). In addition, it was recently shown that isolated A2 but not isolated A1 and A3-C1-C2 subunits of activated fVIII is able to accelerate factor IXa-catalyzed conversion of factor X by approximately 100-fold (Fay, P. J. and Koshibu, K., *Blood* 92:353a (abstract) (1998)). Even though acceleration of the factor X activation by A2 is only 1% of that in the presence of heterotrimeric activated fVIII (A1/A2/A3-C1-C2) (Fay, P. J. and Koshibu, K., *Blood* 92:353a (abstract) (1998)), it is possible that LRP-mediated removal of A2, dissociated from fVIIIa bound to a phospholipid membrane at the site of coagulation, is important to prevent activation of factor X not in the place of the coagulation event.

In summary, the current study demonstrates that LRP can bind fVIII/vWf complex and mediate uptake of fVIII from it. In vivo clearance studies shows that LRP indeed functions to remove fVIII from plasma.

Example 5

Experiments on the development of recombinant fVIII molecule with extended lifetime in circulation. Since recombinant fVIII products are widely used for fVIII replacement therapy in hemophiliacs who have decreased or nonfunctional fVIII, the generation of mutant(s) with a prolonged lifetime is a promising approach to increase the efficacy and reduce the cost of fVIII infusion therapy. A 39 kDa receptor associated protein (RAP) binds reversibly to LRP and inhibits the binding of other ligands and therefore serves as a useful tool for testing whether LRP is involved in endocytosis of a given ligand. We found that fVIII binding to LRP is inhibited by RAP, confirming the specificity of this interaction. Since von Willebrand factor (vWf), bound to fVIII in the circulation, does not inhibit fVIII binding to purified LRP, we proposed that the removal of fVIII/vWf complex from circulation may also be LRP-mediated. This role of LRP was supported by our finding that the half-life of human $^{125}$I-fVIII/vWf complex in mice was 2.5-times prolonged in the presence of RAP.

Based on our finding that fVIII amino acids 484–509 were important for fVIII binding to LRP, these amino acids are also important for LRP-mediated endocytosis. To identify the key fVIII amino acids required for endocytosis, single residues 484–509 are mutated to Ala in the B-domain deleted fVIII (B(−) fVIII). Since the basic residues are commonly involved in ligand binding to LRP, six basic residues within 484–509 (3 Lys and 3 Arg) are mutated. U.S. Pat. No. 5,859,204 discloses the substitution to Ala of three of these residues (Arg$^{484}$, Lys$^{493}$ and Arg$^{490}$); however the other 3 residues—Arg$^{490}$, Lys$^{496}$ and Lys$^{499}$—were not substituted. Thus, these residues, individually and in combination, are mutated to Ala. In particular, each of three Arg and each of three Lys are mutated by pairs (this implies preparation of 9 additional fVIII Ala double-mutants).

It is then determined whether the endocytosis by LRP-expressing cells of vWf complexes with B(−) fVIII mutant(s) is reduced compared to that of wild-type B(−) fVIII/vWf. Some mutations result in a decreased rate of internalization and a longer in vivo half-life of the complex of the B-fVIII mutant with vWf in plasma of mice compared to that of wild type B-fVIII/vWf complex. The data of the in vivo experiments performed in normal and fVIII-deficient mice is mathematically analyzed using biphasic time-course clearance model and equations approximating interspecies scaling which allow the prediction fVIII half-life in humans (*Toxicology and Applied Pharmacology* 136:75–78 (1996)).

Clearance of mutant fVIII in vWf-deficient mice which lack fVIII in circulation (a mouse model for severe von Willebrand disease is described in *Proc. Natl. Acad. Sci. USA* 95:9524–9529 (1998)) is also analyzed. These experiments are aimed at determining mutant fVIII's prolonged half-life in the absence of vWf. Factor VIII interaction with endothelial cells is also analyzed, since this interaction leads to fVIII internalization. In experiments using fluorescent microscopy techniques we observed uptake of fVIII by endothelial cells. Since a fine equilibrium exists in circulation between fVIII bound to vWf and fVIII bound and internalized by endothelial cells, fVIII interaction with the phospholipid endothelial cell membrane is an important factor influencing the concentration of fVIII (and hence its half-life) in circulation following fVIII injection.

Therefore, individual amino acids that play a role in fVIII binding to vWf and to phospholipid are identified within the previously localized fVIII phospholipid binding site (C2 domain region 2303–2332). We identify the amino acids playing an important role in fVIII binding to phospholipid but not to vWf. The amino acids which participate in fVIII binding to vWf and to phospholipids are selected based on the following observations. The homology search between the C2 domain of fVIII and the corresponding region of the discoidin and a family of homologous proteins, containing the so called DS domain, has revealed the fVIII C2 domain sequences involved in the formation of β-structures. In addition, it has been shown that the synthetic fVIII peptide 2310–2320 in which residues 2310 and 2320 are covalently linked to reproduce the corresponding loop structure within the C2 domain, competes for fVIII binding with vWf or phospholipid. Therefore, residues within the 2311–2319 region are mutated to Ala, and other amino acids. Since fV, a fVIII homolog, does not bind to vWf, we mutate only five residues which are unique within the 2311–2319 region of fVIII. The mutants are tested for binding to vWf and phospholipid, which identifies the fVIII residues playing a key role in binding to these ligand.

Clearance of the fVIII mutants with reduced phospholipid binding is compared with that of wt-fVIII in normal and hemophilic mice to determine the contribution of the phospholipid-dependent fVIII clearance component to total fVIII clearance.

The mutations within the C2 domain region 2310–2320 prove to be effective for extension of fVIII lifetime in circulation, so we generate mutant fVIII in which both the C2 domain mutation(s) (positions 2310–2320) and mutation(s) within the A2 (positions 484–509) are combined.

To test the designed extended lifetime fVIII for gene therapy purposes, the mutated fVIII gene is inserted in a virus-based vector, and delivered into hemophilia A mice. The time course of the fVIII in vivo expression level is assessed as follows: the number of the gene copies per cell (hepatic), the gene transcription level, fVIII activity and the antigen level are determined. Since it was shown that high titer antibodies increase clearance of fVIII (*Br. J. Hematol.* 93:688–693 (1996)), we examine the immune response against the extended lifetime fVIII. We also compare its half-life in circulation in hemophilia A mice which formed antibodies against wild type fVIII.

---

What is claimed is:

1. A mutant factor VIII comprising an amino acid substitution at one or more positions selected from the group consisting of a position corresponding to Lys(377) and Lys(466) of SEQ ID NO:5, and optionally at one or more positions selected from the group consisting of a substitution at a position corresponding to Lys(380), Ser(488), Arg(489), Arg(490), Leu(491), Lys(493), Lys(496), His(497), Lys(499), Lys(512), Lys(523), and Lys(556) of SEQ ID NO:5, wherein the mutant factor VIII has procoagulant activity.

2. A pharmaceutically acceptable composition comprising the mutant factor VIII of claim 1.

3. A method of treating hemophilia comprising administering to a patient in need thereof an effective amount of the composition of claim 2.

4. The mutant factor VIII of claim 1, further comprising an amino acid substitution at one or more additional positions in the A2 domain.

5. A pharmaceutically acceptable composition comprising the mutant factor VIII of claim 4.

6. A method of treating hemophilia comprising administering to a patient in need thereof an effective amount of the composition of claim 5.

7. A mutant factor VIII comprising an amino acid substitution at one or more positions selected from the group consisting of a position corresponding to Lys(377) and Lys(466) of SEQ ID NO:2, and optionally at one or more substitutions selected from the group consisting of a substitution at a position corresponding to Lys(380), Ser(488), Arg(489), Arg(490), Leu(491), Lys(493), Lys(496), His(497), Lys(499), Lys(512), Lys(523), and Lys(556) of SEQ ID NO:2, wherein the mutant factor VIII has procoagulant activity.

8. A pharmaceutically acceptable composition comprising the mutant factor VIII of claim 7.

9. A method of treating hemophilia comprising administering to a patient in need thereof an effective amount of the composition of claim 8.

10. The mutant factor VIII of claim 7, further comprising an amino acid substitution at one or more additional positions in the A2 domain.

11. A pharmaceutically acceptable composition comprising the mutant factor VIII of claim 10.

12. A method of treating hemophilia comprising administering to a patient in need thereof an effective amount of the composition of claim 11.

* * * * *

SEQUENCE LISTING

```
<160> NUMBER OF SEQ ID NOS: 9

<210> SEQ ID NO 1
<211> LENGTH: 8967
<212> TYPE: DNA
<213> ORGANISM: Homo sapiens
<220> FEATURE:
<221> NAME/KEY: sig_peptide
<222> LOCATION: (110)..(166)
<220> FEATURE:
<221> NAME/KEY: CDS
<222> LOCATION: (110)..(7162)
<220> FEATURE:
<221> NAME/KEY: mat_peptide
<222> LOCATION: (167)..(7162)

<400> SEQUENCE: 1
cttttcatta aatcagaaat tttacttttt tccctcctg ggagctaaag atattttaga        60
gaagaattaa cctttttgctt ctccagttga acatttgtag caataagtc atg caa ata      118
                                                        Met Gln Ile gag ctc tcc acc tgc ttc ttt ctg tgc ctt ttg cga ttc tgc ttt agt        166
Glu Leu Ser Thr Cys Phe Phe Leu Cys Leu Leu Arg Phe Cys Phe Ser
    -15                 -10                  -5                 -1 gcc acc aga aga tac tac ctg ggt gca gtg gaa ctg tca tgg gac tat        214
Ala Thr Arg Arg Tyr Tyr Leu Gly Ala Val Glu Leu Ser Trp Asp Tyr
  1               5                  10                  15 atg caa agt gat ctc ggt gag ctg cct gtg gac gca aga ttt cct cct        262
Met Gln Ser Asp Leu Gly Glu Leu Pro Val Asp Ala Arg Phe Pro Pro
                 20                  25                  30 aga gtg cca aaa tct ttt cca ttc aac acc tca gtc gtg tac aaa aag        310
Arg Val Pro Lys Ser Phe Pro Phe Asn Thr Ser Val Val Tyr Lys Lys
             35                  40                  45 act ctg ttt gta gaa ttc acg gat cac ctt ttc aac atc gct aag cca        358
```

```
                Thr Leu Phe Val Glu Phe Thr Asp His Leu Phe Asn Ile Ala Lys Pro
                    50                  55                  60 agg cca ccc tgg atg ggt ctg cta ggt cct acc atc cag gct gag gtt          406
Arg Pro Pro Trp Met Gly Leu Leu Gly Pro Thr Ile Gln Ala Glu Val
 65                  70                  75                  80 tat gat aca gtg gtc att aca ctt aag aac atg gct tcc cat cct gtc          454
Tyr Asp Thr Val Val Ile Thr Leu Lys Asn Met Ala Ser His Pro Val
                 85                  90                  95 agt ctt cat gct gtt ggt gta tcc tac tgg aaa gct tct gag gga gct          502
Ser Leu His Ala Val Gly Val Ser Tyr Trp Lys Ala Ser Glu Gly Ala
                100                 105                 110 gaa tat gat gat cag acc agt caa agg gag aaa gaa gat gat aaa gtc          550
Glu Tyr Asp Asp Gln Thr Ser Gln Arg Glu Lys Glu Asp Asp Lys Val
            115                 120                 125 ttc cct ggt gga agc cat aca tat gtc tgg cag gtc ctg aaa gag aat          598
Phe Pro Gly Gly Ser His Thr Tyr Val Trp Gln Val Leu Lys Glu Asn
130                 135                 140 ggt cca atg gcc tct gac cca ctg tgc ctt acc tac tca tat ctt tct          646
Gly Pro Met Ala Ser Asp Pro Leu Cys Leu Thr Tyr Ser Tyr Leu Ser
145                 150                 155                 160 cat gtg gac ctg gta aaa gac ttg aat tca ggc ctc att gga gcc cta          694
His Val Asp Leu Val Lys Asp Leu Asn Ser Gly Leu Ile Gly Ala Leu
                165                 170                 175 cta gta tgt aga gaa ggg agt ctg gcc aag gaa aag aca cag acc ttg          742
Leu Val Cys Arg Glu Gly Ser Leu Ala Lys Glu Lys Thr Gln Thr Leu
            180                 185                 190 cac aaa ttt ata cta ctt ttt gct gta ttt gat gaa ggg aaa agt tgg          790
His Lys Phe Ile Leu Leu Phe Ala Val Phe Asp Glu Gly Lys Ser Trp
        195                 200                 205 cac tca gaa aca aag aac tcc ttg atg cag gat agg gat gct gca tct          838
His Ser Glu Thr Lys Asn Ser Leu Met Gln Asp Arg Asp Ala Ala Ser
    210                 215                 220 gct cgg gcc tgg cct aaa atg cac aca gtc aat ggt tat gta aac agg          886
Ala Arg Ala Trp Pro Lys Met His Thr Val Asn Gly Tyr Val Asn Arg
225                 230                 235                 240 tct ctg cca ggt ctg att gga tgc cac agg aaa tca gtc tat tgg cat          934
Ser Leu Pro Gly Leu Ile Gly Cys His Arg Lys Ser Val Tyr Trp His
                245                 250                 255 gtg att gga atg ggc acc act cct gaa gtg cac tca ata ttc ctc gaa          982
Val Ile Gly Met Gly Thr Thr Pro Glu Val His Ser Ile Phe Leu Glu
            260                 265                 270 ggt cac aca ttt ctt gtg agg aac cat cgc cag gcg tcc ttg gaa atc         1030
Gly His Thr Phe Leu Val Arg Asn His Arg Gln Ala Ser Leu Glu Ile
        275                 280                 285 tcg cca ata act ttc ctt act gct caa aca ctc ttg atg gac ctt gga         1078
Ser Pro Ile Thr Phe Leu Thr Ala Gln Thr Leu Leu Met Asp Leu Gly
    290                 295                 300 cag ttt cta ctg ttt tgt cat atc tct tcc cac caa cat gat ggc atg         1126
Gln Phe Leu Leu Phe Cys His Ile Ser Ser His Gln His Asp Gly Met
305                 310                 315                 320 gaa gct tat gtc aaa gta gac agc tgt cca gag gaa ccc caa cta cga         1174
Glu Ala Tyr Val Lys Val Asp Ser Cys Pro Glu Glu Pro Gln Leu Arg
                325                 330                 335 atg aaa aat aat gaa gaa gcg gaa gac tat gat gat gat ctt act gat         1222
Met Lys Asn Asn Glu Glu Ala Glu Asp Tyr Asp Asp Asp Leu Thr Asp
            340                 345                 350 tct gaa atg gat gtg gtc agg ttt gat gat gac aac tct cct tcc ttt         1270
Ser Glu Met Asp Val Val Arg Phe Asp Asp Asp Asn Ser Pro Ser Phe
        355                 360                 365
```

-continued

| | | |
|---|---|---|
| atc caa att cgc tca gtt gcc aag aag cat cct aaa act tgg gta cat<br>Ile Gln Ile Arg Ser Val Ala Lys Lys His Pro Lys Thr Trp Val His<br>370 375 380 | 1318 | |
| tac att gct gct gaa gag gag gac tgg gac tat gct ccc tta gtc ctc<br>Tyr Ile Ala Ala Glu Glu Glu Asp Trp Asp Tyr Ala Pro Leu Val Leu<br>385 390 395 400 | 1366 | |
| gcc ccc gat gac aga agt tat aaa agt caa tat ttg aac aat ggc cct<br>Ala Pro Asp Asp Arg Ser Tyr Lys Ser Gln Tyr Leu Asn Asn Gly Pro<br>405 410 415 | 1414 | |
| cag cgg att ggt agg aag tac aaa aaa gtc cga ttt atg gca tac aca<br>Gln Arg Ile Gly Arg Lys Tyr Lys Lys Val Arg Phe Met Ala Tyr Thr<br>420 425 430 | 1462 | |
| gat gaa acc ttt aag act cgt gaa gct att cag cat gaa tca gga atc<br>Asp Glu Thr Phe Lys Thr Arg Glu Ala Ile Gln His Glu Ser Gly Ile<br>435 440 445 | 1510 | |
| ttg gga cct tta ctt tat ggg gaa gtt gga gac aca ctg ttg att ata<br>Leu Gly Pro Leu Leu Tyr Gly Glu Val Gly Asp Thr Leu Leu Ile Ile<br>450 455 460 | 1558 | |
| ttt aag aat caa gca agc aga cca tat aac atc tac cct cac gga atc<br>Phe Lys Asn Gln Ala Ser Arg Pro Tyr Asn Ile Tyr Pro His Gly Ile<br>465 470 475 480 | 1606 | |
| act gat gtc cgt cct ttg tat tca agg aga tta cca aaa ggt gta aaa<br>Thr Asp Val Arg Pro Leu Tyr Ser Arg Arg Leu Pro Lys Gly Val Lys<br>485 490 495 | 1654 | |
| cat ttg aag gat ttt cca att ctg cca gga gaa ata ttc aaa tat aaa<br>His Leu Lys Asp Phe Pro Ile Leu Pro Gly Glu Ile Phe Lys Tyr Lys<br>500 505 510 | 1702 | |
| tgg aca gtg act gta gaa gat ggg cca act aaa tca gat cct cgg tgc<br>Trp Thr Val Thr Val Glu Asp Gly Pro Thr Lys Ser Asp Pro Arg Cys<br>515 520 525 | 1750 | |
| ctg acc cgc tat tac tct agt ttc gtt aat atg gag aga gat cta gct<br>Leu Thr Arg Tyr Tyr Ser Ser Phe Val Asn Met Glu Arg Asp Leu Ala<br>530 535 540 | 1798 | |
| tca gga ctc att ggc cct ctc ctc atc tgc tac aaa gaa tct gta gat<br>Ser Gly Leu Ile Gly Pro Leu Leu Ile Cys Tyr Lys Glu Ser Val Asp<br>545 550 555 560 | 1846 | |
| caa aga gga aac cag ata atg tca gac aag agg aat gtc atc ctg ttt<br>Gln Arg Gly Asn Gln Ile Met Ser Asp Lys Arg Asn Val Ile Leu Phe<br>565 570 575 | 1894 | |
| tct gta ttt gat gag aac cga agc tgg tac ctc aca gag aat ata caa<br>Ser Val Phe Asp Glu Asn Arg Ser Trp Tyr Leu Thr Glu Asn Ile Gln<br>580 585 590 | 1942 | |
| cgc ttt ctc ccc aat cca gct gga gtg cag ctt gag gat cca gag ttc<br>Arg Phe Leu Pro Asn Pro Ala Gly Val Gln Leu Glu Asp Pro Glu Phe<br>595 600 605 | 1990 | |
| caa gcc tcc aac atc atg cac agc atc aat ggc tat gtt ttt gat agt<br>Gln Ala Ser Asn Ile Met His Ser Ile Asn Gly Tyr Val Phe Asp Ser<br>610 615 620 | 2038 | |
| ttg cag ttg tca gtt tgt ttg cat gag gtg gca tac tgg tac att cta<br>Leu Gln Leu Ser Val Cys Leu His Glu Val Ala Tyr Trp Tyr Ile Leu<br>625 630 635 640 | 2086 | |
| agc att gga gca cag act gac ttc ctt tct gtc ttc ttc tct gga tat<br>Ser Ile Gly Ala Gln Thr Asp Phe Leu Ser Val Phe Phe Ser Gly Tyr<br>645 650 655 | 2134 | |
| acc ttc aaa cac aaa atg gtc tat gaa gac aca ctc acc cta ttc cca<br>Thr Phe Lys His Lys Met Val Tyr Glu Asp Thr Leu Thr Leu Phe Pro<br>660 665 670 | 2182 | |
| ttc tca gga gaa act gtc ttc atg tcg atg gaa aac cca ggt cta tgg<br>Phe Ser Gly Glu Thr Val Phe Met Ser Met Glu Asn Pro Gly Leu Trp<br>675 680 685 | 2230 | |

-continued

| | | |
|---|---|---|
| att ctg ggg tgc cac aac tca gac ttt cgg aac aga ggc atg acc gcc<br>Ile Leu Gly Cys His Asn Ser Asp Phe Arg Asn Arg Gly Met Thr Ala<br>690                        695                    700 | 2278 | |
| tta ctg aag gtt tct agt tgt gac aag aac act ggt gat tat tac gag<br>Leu Leu Lys Val Ser Ser Cys Asp Lys Asn Thr Gly Asp Tyr Tyr Glu<br>705                        710                    715                    720 | 2326 | |
| gac agt tat gaa gat att tca gca tac ttg ctg agt aaa aac aat gcc<br>Asp Ser Tyr Glu Asp Ile Ser Ala Tyr Leu Leu Ser Lys Asn Asn Ala<br>                  725                    730                    735 | 2374 | |
| att gaa cca aga agc ttc tcc cag aat tca aga cac cgt agc act agg<br>Ile Glu Pro Arg Ser Phe Ser Gln Asn Ser Arg His Arg Ser Thr Arg<br>        740                    745                    750 | 2422 | |
| caa aag caa ttt aat gcc acc aca att cca gaa aat gac ata gag aag<br>Gln Lys Gln Phe Asn Ala Thr Thr Ile Pro Glu Asn Asp Ile Glu Lys<br>755                        760                    765 | 2470 | |
| act gac cct tgg ttt gca cac aga aca cct atg cct aaa ata caa aat<br>Thr Asp Pro Trp Phe Ala His Arg Thr Pro Met Pro Lys Ile Gln Asn<br>770                        775                    780 | 2518 | |
| gtc tcc tct agt gat ttg ttg atg ctc ttg cga cag agt cct act cca<br>Val Ser Ser Ser Asp Leu Leu Met Leu Leu Arg Gln Ser Pro Thr Pro<br>785                        790                    795                    800 | 2566 | |
| cat ggg cta tcc tta tct gat ctc caa gaa gcc aaa tat gag act ttt<br>His Gly Leu Ser Leu Ser Asp Leu Gln Glu Ala Lys Tyr Glu Thr Phe<br>                  805                    810                    815 | 2614 | |
| tct gat gat cca tca cct gga gca ata gac agt aat aac agc ctg tct<br>Ser Asp Asp Pro Ser Pro Gly Ala Ile Asp Ser Asn Asn Ser Leu Ser<br>        820                    825                    830 | 2662 | |
| gaa atg aca cac ttc agg cca cag ctc cat cac agt ggg gac atg gta<br>Glu Met Thr His Phe Arg Pro Gln Leu His His Ser Gly Asp Met Val<br>835                        840                    845 | 2710 | |
| ttt acc cct gag tca ggc ctc caa tta aga tta aat gag aaa ctg ggg<br>Phe Thr Pro Glu Ser Gly Leu Gln Leu Arg Leu Asn Glu Lys Leu Gly<br>850                        855                    860 | 2758 | |
| aca act gca gca aca gag ttg aag aaa ctt gat ttc aaa gtt tct agt<br>Thr Thr Ala Ala Thr Glu Leu Lys Lys Leu Asp Phe Lys Val Ser Ser<br>865                        870                    875                    880 | 2806 | |
| aca tca aat aat ctg att tca aca att cca tca gac aat ttg gca gca<br>Thr Ser Asn Asn Leu Ile Ser Thr Ile Pro Ser Asp Asn Leu Ala Ala<br>                  885                    890                    895 | 2854 | |
| ggt act gat aat aca agt tcc tta gga ccc cca agt atg cca gtt cat<br>Gly Thr Asp Asn Thr Ser Ser Leu Gly Pro Pro Ser Met Pro Val His<br>        900                    905                    910 | 2902 | |
| tat gat agt caa tta gat acc act cta ttt ggc aaa aag tca tct ccc<br>Tyr Asp Ser Gln Leu Asp Thr Thr Leu Phe Gly Lys Lys Ser Ser Pro<br>915                        920                    925 | 2950 | |
| ctt act gag tct ggt gga cct ctg agc ttg agt gaa gaa aat aat gat<br>Leu Thr Glu Ser Gly Gly Pro Leu Ser Leu Ser Glu Glu Asn Asn Asp<br>930                        935                    940 | 2998 | |
| tca aag ttg tta gaa tca ggt tta atg aat agc caa gaa agt tca tgg<br>Ser Lys Leu Leu Glu Ser Gly Leu Met Asn Ser Gln Glu Ser Ser Trp<br>945                        950                    955                    960 | 3046 | |
| gga aaa aat gta tcg tca aca gag agt ggt agg tta ttt aaa ggg aaa<br>Gly Lys Asn Val Ser Ser Thr Glu Ser Gly Arg Leu Phe Lys Gly Lys<br>                  965                    970                    975 | 3094 | |
| aga gct cat gga cct gct ttg ttg act aaa gat aat gcc tta ttc aaa<br>Arg Ala His Gly Pro Ala Leu Leu Thr Lys Asp Asn Ala Leu Phe Lys<br>        980                    985                    990 | 3142 | |
| gtt agc atc tct ttg tta aag aca    aac aaa act tcc aat    aat tca gca<br>Val Ser Ile Ser Leu Leu Lys Thr    Asn Lys Thr Ser Asn    Asn Ser Ala | 3190 | |

|  |  |  |  |  |  |  |  |  |  |  |  |  |  |  |
|---|---|---|---|---|---|---|---|---|---|---|---|---|---|---|
|  | 995 |  |  |  | 1000 |  |  |  |  | 1005 |  |  |  |  |
| act | aat | aga | aag | act | cac | att | gat | ggc | cca | tca | tta | tta | att | gag | 3235 |
| Thr | Asn | Arg | Lys | Thr | His | Ile | Asp | Gly | Pro | Ser | Leu | Leu | Ile | Glu |  |
|  | 1010 |  |  |  | 1015 |  |  |  |  | 1020 |  |  |  |  |
| aat | agt | cca | tca | gtc | tgg | caa | aat | ata | tta | gaa | agt | gac | act | gag | 3280 |
| Asn | Ser | Pro | Ser | Val | Trp | Gln | Asn | Ile | Leu | Glu | Ser | Asp | Thr | Glu |  |
|  | 1025 |  |  |  | 1030 |  |  |  |  | 1035 |  |  |  |  |
| ttt | aaa | aaa | gtg | aca | cct | ttg | att | cat | gac | aga | atg | ctt | atg | gac | 3325 |
| Phe | Lys | Lys | Val | Thr | Pro | Leu | Ile | His | Asp | Arg | Met | Leu | Met | Asp |  |
|  | 1040 |  |  |  | 1045 |  |  |  |  | 1050 |  |  |  |  |
| aaa | aat | gct | aca | gct | ttg | agg | cta | aat | cat | atg | tca | aat | aaa | act | 3370 |
| Lys | Asn | Ala | Thr | Ala | Leu | Arg | Leu | Asn | His | Met | Ser | Asn | Lys | Thr |  |
|  | 1055 |  |  |  | 1060 |  |  |  |  | 1065 |  |  |  |  |
| act | tca | tca | aaa | aac | atg | gaa | atg | gtc | caa | cag | aaa | aaa | gag | ggc | 3415 |
| Thr | Ser | Ser | Lys | Asn | Met | Glu | Met | Val | Gln | Gln | Lys | Lys | Glu | Gly |  |
|  | 1070 |  |  |  | 1075 |  |  |  |  | 1080 |  |  |  |  |
| ccc | att | cca | cca | gat | gca | caa | aat | cca | gat | atg | tcg | ttc | ttt | aag | 3460 |
| Pro | Ile | Pro | Pro | Asp | Ala | Gln | Asn | Pro | Asp | Met | Ser | Phe | Phe | Lys |  |
|  | 1085 |  |  |  | 1090 |  |  |  |  | 1095 |  |  |  |  |
| atg | cta | ttc | ttg | cca | gaa | tca | gca | agg | tgg | ata | caa | agg | act | cat | 3505 |
| Met | Leu | Phe | Leu | Pro | Glu | Ser | Ala | Arg | Trp | Ile | Gln | Arg | Thr | His |  |
|  | 1100 |  |  |  | 1105 |  |  |  |  | 1110 |  |  |  |  |
| gga | aag | aac | tct | ctg | aac | tct | ggg | caa | ggc | ccc | agt | cca | aag | caa | 3550 |
| Gly | Lys | Asn | Ser | Leu | Asn | Ser | Gly | Gln | Gly | Pro | Ser | Pro | Lys | Gln |  |
|  | 1115 |  |  |  | 1120 |  |  |  |  | 1125 |  |  |  |  |
| tta | gta | tcc | tta | gga | cca | gaa | aaa | tct | gtg | gaa | ggt | cag | aat | ttc | 3595 |
| Leu | Val | Ser | Leu | Gly | Pro | Glu | Lys | Ser | Val | Glu | Gly | Gln | Asn | Phe |  |
|  | 1130 |  |  |  | 1135 |  |  |  |  | 1140 |  |  |  |  |
| ttg | tct | gag | aaa | aac | aaa | gtg | gta | gta | gga | aag | ggt | gaa | ttt | aca | 3640 |
| Leu | Ser | Glu | Lys | Asn | Lys | Val | Val | Val | Gly | Lys | Gly | Glu | Phe | Thr |  |
|  | 1145 |  |  |  | 1150 |  |  |  |  | 1155 |  |  |  |  |
| aag | gac | gta | gga | ctc | aaa | gag | atg | gtt | ttt | cca | agc | agc | aga | aac | 3685 |
| Lys | Asp | Val | Gly | Leu | Lys | Glu | Met | Val | Phe | Pro | Ser | Ser | Arg | Asn |  |
|  | 1160 |  |  |  | 1165 |  |  |  |  | 1170 |  |  |  |  |
| cta | ttt | ctt | act | aac | ttg | gat | aat | tta | cat | gaa | aat | aat | aca | cac | 3730 |
| Leu | Phe | Leu | Thr | Asn | Leu | Asp | Asn | Leu | His | Glu | Asn | Asn | Thr | His |  |
|  | 1175 |  |  |  | 1180 |  |  |  |  | 1185 |  |  |  |  |
| aat | caa | gaa | aaa | aaa | att | cag | gaa | gaa | ata | gaa | aag | aag | gaa | aca | 3775 |
| Asn | Gln | Glu | Lys | Lys | Ile | Gln | Glu | Glu | Ile | Glu | Lys | Lys | Glu | Thr |  |
|  | 1190 |  |  |  | 1195 |  |  |  |  | 1200 |  |  |  |  |
| tta | atc | caa | gag | aat | gta | gtt | ttg | cct | cag | ata | cat | aca | gtg | act | 3820 |
| Leu | Ile | Gln | Glu | Asn | Val | Val | Leu | Pro | Gln | Ile | His | Thr | Val | Thr |  |
|  | 1205 |  |  |  | 1210 |  |  |  |  | 1215 |  |  |  |  |
| ggc | act | aag | aat | ttc | atg | aag | aac | ctt | ttc | tta | ctg | agc | act | agg | 3865 |
| Gly | Thr | Lys | Asn | Phe | Met | Lys | Asn | Leu | Phe | Leu | Leu | Ser | Thr | Arg |  |
|  | 1220 |  |  |  | 1225 |  |  |  |  | 1230 |  |  |  |  |
| caa | aat | gta | gaa | ggt | tca | tat | gac | ggg | gca | tat | gct | cca | gta | ctt | 3910 |
| Gln | Asn | Val | Glu | Gly | Ser | Tyr | Asp | Gly | Ala | Tyr | Ala | Pro | Val | Leu |  |
|  | 1235 |  |  |  | 1240 |  |  |  |  | 1245 |  |  |  |  |
| caa | gat | ttt | agg | tca | tta | aat | gat | tca | aca | aat | aga | aca | aag | aaa | 3955 |
| Gln | Asp | Phe | Arg | Ser | Leu | Asn | Asp | Ser | Thr | Asn | Arg | Thr | Lys | Lys |  |
|  | 1250 |  |  |  | 1255 |  |  |  |  | 1260 |  |  |  |  |
| cac | aca | gct | cat | ttc | tca | aaa | aaa | ggg | gag | gaa | gaa | aac | ttg | gaa | 4000 |
| His | Thr | Ala | His | Phe | Ser | Lys | Lys | Gly | Glu | Glu | Glu | Asn | Leu | Glu |  |
|  | 1265 |  |  |  | 1270 |  |  |  |  | 1275 |  |  |  |  |
| ggc | ttg | gga | aat | caa | acc | aag | caa | att | gta | gag | aaa | tat | gca | tgc | 4045 |
| Gly | Leu | Gly | Asn | Gln | Thr | Lys | Gln | Ile | Val | Glu | Lys | Tyr | Ala | Cys |  |
|  | 1280 |  |  |  | 1285 |  |  |  |  | 1290 |  |  |  |  |
| acc | aca | agg | ata | tct | cct | aat | aca | agc | cag | cag | aat | ttt | gtc | acg | 4090 |

```
                Thr Thr Arg Ile Ser Pro Asn Thr Ser Gln Gln Asn Phe Val Thr
                    1295                1300                1305 caa cgt agt aag aga gct ttg aaa caa ttc aga ctc cca cta gaa             4135
Gln Arg Ser Lys Arg Ala Leu Lys Gln Phe Arg Leu Pro Leu Glu
1310                1315                1320 gaa aca gaa ctt gaa aaa agg ata att gtg gat gac acc tca acc             4180
Glu Thr Glu Leu Glu Lys Arg Ile Ile Val Asp Asp Thr Ser Thr
1325                1330                1335 cag tgg tcc aaa aac atg aaa cat ttg acc ccg agc acc ctc aca             4225
Gln Trp Ser Lys Asn Met Lys His Leu Thr Pro Ser Thr Leu Thr
1340                1345                1350 cag ata gac tac aat gag aag gag aaa ggg gcc att act cag tct             4270
Gln Ile Asp Tyr Asn Glu Lys Glu Lys Gly Ala Ile Thr Gln Ser
1355                1360                1365 ccc tta tca gat tgc ctt acg agg agt cat agc atc cct caa gca             4315
Pro Leu Ser Asp Cys Leu Thr Arg Ser His Ser Ile Pro Gln Ala
1370                1375                1380 aat aga tct cca tta ccc att gca aag gta tca tca ttt cca tct             4360
Asn Arg Ser Pro Leu Pro Ile Ala Lys Val Ser Ser Phe Pro Ser
1385                1390                1395 att aga cct ata tat ctg acc agg gtc cta ttc caa gac aac tct             4405
Ile Arg Pro Ile Tyr Leu Thr Arg Val Leu Phe Gln Asp Asn Ser
1400                1405                1410 tct cat ctt cca gca gca tct tat aga aag aaa gat tct ggg gtc             4450
Ser His Leu Pro Ala Ala Ser Tyr Arg Lys Lys Asp Ser Gly Val
1415                1420                1425 caa gaa agc agt cat ttc tta caa gga gcc aaa aaa aat aac ctt             4495
Gln Glu Ser Ser His Phe Leu Gln Gly Ala Lys Lys Asn Asn Leu
1430                1435                1440 tct tta gcc att cta acc ttg gag atg act ggt gat caa aga gag             4540
Ser Leu Ala Ile Leu Thr Leu Glu Met Thr Gly Asp Gln Arg Glu
1445                1450                1455 gtt ggc tcc ctg ggg aca agt gcc aca aat tca gtc aca tac aag             4585
Val Gly Ser Leu Gly Thr Ser Ala Thr Asn Ser Val Thr Tyr Lys
1460                1465                1470 aaa gtt gag aac act gtt ctc ccg aaa cca gac ttg ccc aaa aca             4630
Lys Val Glu Asn Thr Val Leu Pro Lys Pro Asp Leu Pro Lys Thr
1475                1480                1485 tct ggc aaa gtt gaa ttg ctt cca aaa gtt cac att tat cag aag             4675
Ser Gly Lys Val Glu Leu Leu Pro Lys Val His Ile Tyr Gln Lys
1490                1495                1500 gac cta ttc cct acg gaa act agc aat ggg tct cct ggc cat ctg             4720
Asp Leu Phe Pro Thr Glu Thr Ser Asn Gly Ser Pro Gly His Leu
1505                1510                1515 gat ctc gtg gaa ggg agc ctt ctt cag gga aca gag gga gcg att             4765
Asp Leu Val Glu Gly Ser Leu Leu Gln Gly Thr Glu Gly Ala Ile
1520                1525                1530 aag tgg aat gaa gca aac aga cct gga aaa gtt ccc ttt ctg aga             4810
Lys Trp Asn Glu Ala Asn Arg Pro Gly Lys Val Pro Phe Leu Arg
1535                1540                1545 gta gca aca gaa agc tct gca aag act ccc tcc aag cta ttg gat             4855
Val Ala Thr Glu Ser Ser Ala Lys Thr Pro Ser Lys Leu Leu Asp
1550                1555                1560 cct ctt gct tgg gat aac cac tat ggt act cag ata cca aaa gaa             4900
Pro Leu Ala Trp Asp Asn His Tyr Gly Thr Gln Ile Pro Lys Glu
1565                1570                1575 gag tgg aaa tcc caa gag aag tca cca gaa aaa aca gct ttt aag             4945
Glu Trp Lys Ser Gln Glu Lys Ser Pro Glu Lys Thr Ala Phe Lys
1580                1585                1590
```

```
                                          -continued
aaa aag gat acc att ttg tcc ctg aac gct tgt gaa agc aat cat      4990
Lys Lys Asp Thr Ile Leu Ser Leu Asn Ala Cys Glu Ser Asn His
    1595                1600                1605 gca ata gca gca ata aat gag gga caa aat aag ccc gaa ata gaa      5035
Ala Ile Ala Ala Ile Asn Glu Gly Gln Asn Lys Pro Glu Ile Glu
1610                1615                1620 gtc acc tgg gca aag caa ggt agg act gaa agg ctg tgc tct caa      5080
Val Thr Trp Ala Lys Gln Gly Arg Thr Glu Arg Leu Cys Ser Gln
1625                1630                1635 aac cca cca gtc ttg aaa cgc cat caa cgg gaa ata act cgt act      5125
Asn Pro Pro Val Leu Lys Arg His Gln Arg Glu Ile Thr Arg Thr
1640                1645                1650 act ctt cag tca gat caa gag gaa att gac tat gat gat acc ata      5170
Thr Leu Gln Ser Asp Gln Glu Glu Ile Asp Tyr Asp Asp Thr Ile
    1655                1660                1665 tca gtt gaa atg aag aag gaa gat ttt gac att tat gat gag gat      5215
Ser Val Glu Met Lys Lys Glu Asp Phe Asp Ile Tyr Asp Glu Asp
1670                1675                1680 gaa aat cag agc ccc cgc agc ttt caa aag aaa aca cga cac tat      5260
Glu Asn Gln Ser Pro Arg Ser Phe Gln Lys Lys Thr Arg His Tyr
1685                1690                1695 ttt att gct gca gtg gag agg ctc tgg gat tat ggg atg agt agc      5305
Phe Ile Ala Ala Val Glu Arg Leu Trp Asp Tyr Gly Met Ser Ser
    1700                1705                1710 tcc cca cat gtt cta aga aac agg gct cag agt ggc agt gtc cct      5350
Ser Pro His Val Leu Arg Asn Arg Ala Gln Ser Gly Ser Val Pro
1715                1720                1725 cag ttc aag aaa gtt gtt ttc cag gaa ttt act gat ggc tcc ttt      5395
Gln Phe Lys Lys Val Val Phe Gln Glu Phe Thr Asp Gly Ser Phe
1730                1735                1740 act cag ccc tta tac cgt gga gaa cta aat gaa cat ttg gga ctc      5440
Thr Gln Pro Leu Tyr Arg Gly Glu Leu Asn Glu His Leu Gly Leu
    1745                1750                1755 ctg ggg cca tat ata aga gca gaa gtt gaa gat aat atc atg gta      5485
Leu Gly Pro Tyr Ile Arg Ala Glu Val Glu Asp Asn Ile Met Val
1760                1765                1770 act ttc aga aat cag gcc tct cgt ccc tat tcc ttc tat tct agc      5530
Thr Phe Arg Asn Gln Ala Ser Arg Pro Tyr Ser Phe Tyr Ser Ser
1775                1780                1785 ctt att tct tat gag gaa gat cag agg caa gga gca gaa cct aga      5575
Leu Ile Ser Tyr Glu Glu Asp Gln Arg Gln Gly Ala Glu Pro Arg
    1790                1795                1800 aaa aac ttt gtc aag cct aat gaa acc aaa act tac ttt tgg aaa      5620
Lys Asn Phe Val Lys Pro Asn Glu Thr Lys Thr Tyr Phe Trp Lys
1805                1810                1815 gtg caa cat cat atg gca ccc act aaa gat gag ttt gac tgc aaa      5665
Val Gln His His Met Ala Pro Thr Lys Asp Glu Phe Asp Cys Lys
1820                1825                1830 gcc tgg gct tat ttc tct gat gtt gac ctg gaa aaa gat gtg cac      5710
Ala Trp Ala Tyr Phe Ser Asp Val Asp Leu Glu Lys Asp Val His
    1835                1840                1845 tca ggc ctg att gga ccc ctt ctg gtc tgc cac act aac aca ctg      5755
Ser Gly Leu Ile Gly Pro Leu Leu Val Cys His Thr Asn Thr Leu
1850                1855                1860 aac cct gct cat ggg aga caa gtg aca gta cag gaa ttt gct ctg      5800
Asn Pro Ala His Gly Arg Gln Val Thr Val Gln Glu Phe Ala Leu
1865                1870                1875 ttt ttc acc atc ttt gat gag acc aaa agc tgg tac ttc act gaa      5845
Phe Phe Thr Ile Phe Asp Glu Thr Lys Ser Trp Tyr Phe Thr Glu
    1880                1885                1890
```

-continued

| | |
|---|---|
| aat atg gaa aga aac tgc agg gct ccc tgc aat atc cag atg gaa<br>Asn Met Glu Arg Asn Cys Arg Ala Pro Cys Asn Ile Gln Met Glu<br>1895                                   1900                           1905 | 5890 |
| gat ccc act ttt aaa gag aat tat cgc ttc cat gca atc aat ggc<br>Asp Pro Thr Phe Lys Glu Asn Tyr Arg Phe His Ala Ile Asn Gly<br>1910                                   1915                           1920 | 5935 |
| tac ata atg gat aca cta cct ggc tta gta atg gct cag gat caa<br>Tyr Ile Met Asp Thr Leu Pro Gly Leu Val Met Ala Gln Asp Gln<br>1925                                 1930                           1935 | 5980 |
| agg att cga tgg tat ctg ctc agc atg ggc agc aat gaa aac atc<br>Arg Ile Arg Trp Tyr Leu Leu Ser Met Gly Ser Asn Glu Asn Ile<br>1940                               1945                          1950 | 6025 |
| cat tct att cat ttc agt gga cat gtg ttc act gta cga aaa aaa<br>His Ser Ile His Phe Ser Gly His Val Phe Thr Val Arg Lys Lys<br>1955                               1960                          1965 | 6070 |
| gag gag tat aaa atg gca ctg tac aat ctc tat cca ggt gtt ttt<br>Glu Glu Tyr Lys Met Ala Leu Tyr Asn Leu Tyr Pro Gly Val Phe<br>1970                               1975                          1980 | 6115 |
| gag aca gtg gaa atg tta cca tcc aaa gct gga att tgg cgg gtg<br>Glu Thr Val Glu Met Leu Pro Ser Lys Ala Gly Ile Trp Arg Val<br>1985                               1990                          1995 | 6160 |
| gaa tgc ctt att ggc gag cat cta cat gct ggg atg agc aca ctt<br>Glu Cys Leu Ile Gly Glu His Leu His Ala Gly Met Ser Thr Leu<br>2000                               2005                          2010 | 6205 |
| ttt ctg gtg tac agc aat aag tgt cag act ccc ctg gga atg gct<br>Phe Leu Val Tyr Ser Asn Lys Cys Gln Thr Pro Leu Gly Met Ala<br>2015                               2020                          2025 | 6250 |
| tct gga cac att aga gat ttt cag att aca gct tca gga caa tat<br>Ser Gly His Ile Arg Asp Phe Gln Ile Thr Ala Ser Gly Gln Tyr<br>2030                               2035                          2040 | 6295 |
| gga cag tgg gcc cca aag ctg gcc aga ctt cat tat tcc gga tca<br>Gly Gln Trp Ala Pro Lys Leu Ala Arg Leu His Tyr Ser Gly Ser<br>2045                               2050                          2055 | 6340 |
| atc aat gcc tgg agc acc aag gag ccc ttt tct tgg atc aag gtg<br>Ile Asn Ala Trp Ser Thr Lys Glu Pro Phe Ser Trp Ile Lys Val<br>2060                               2065                          2070 | 6385 |
| gat ctg ttg gca cca atg att att cac ggc atc aag acc cag ggt<br>Asp Leu Leu Ala Pro Met Ile Ile His Gly Ile Lys Thr Gln Gly<br>2075                               2080                          2085 | 6430 |
| gcc cgt cag aag ttc tcc agc ctc tac atc tct cag ttt atc atc<br>Ala Arg Gln Lys Phe Ser Ser Leu Tyr Ile Ser Gln Phe Ile Ile<br>2090                               2095                          2100 | 6475 |
| atg tat agt ctt gat ggg aag aag tgg cag act tat cga gga aat<br>Met Tyr Ser Leu Asp Gly Lys Lys Trp Gln Thr Tyr Arg Gly Asn<br>2105                               2110                          2115 | 6520 |
| tcc act gga acc tta atg gtc ttc ttt ggc aat gtg gat tca tct<br>Ser Thr Gly Thr Leu Met Val Phe Phe Gly Asn Val Asp Ser Ser<br>2120                               2125                          2130 | 6565 |
| ggg ata aaa cac aat att ttt aac cct cca att att gct cga tac<br>Gly Ile Lys His Asn Ile Phe Asn Pro Pro Ile Ile Ala Arg Tyr<br>2135                               2140                          2145 | 6610 |
| atc cgt ttg cac cca act cat tat agc att cgc agc act ctt cgc<br>Ile Arg Leu His Pro Thr His Tyr Ser Ile Arg Ser Thr Leu Arg<br>2150                               2155                          2160 | 6655 |
| atg gag ttg atg ggc tgt gat tta aat agt tgc agc atg cca ttg<br>Met Glu Leu Met Gly Cys Asp Leu Asn Ser Cys Ser Met Pro Leu<br>2165                               2170                          2175 | 6700 |
| gga atg gag agt aaa gca ata tca gat gca cag att act gct tca<br>Gly Met Glu Ser Lys Ala Ile Ser Asp Ala Gln Ile Thr Ala Ser | 6745 |

-continued

| | | | | | | | | | | | | | | |
|---|---|---|---|---|---|---|---|---|---|---|---|---|---|---|
| | | | 2180 | | | | | 2185 | | | | | 2190 | |
| tcc | tac | ttt | acc | aat | atg | ttt | gcc | acc | tgg | tct | cct | tca | aaa | gct | 6790 |
| Ser | Tyr | Phe | Thr | Asn | Met | Phe | Ala | Thr | Trp | Ser | Pro | Ser | Lys | Ala | |
| | 2195 | | | | | 2200 | | | | | 2205 | | | | |
| cga | ctt | cac | ctc | caa | ggg | agg | agt | aat | gcc | tgg | aga | cct | cag | gtg | 6835 |
| Arg | Leu | His | Leu | Gln | Gly | Arg | Ser | Asn | Ala | Trp | Arg | Pro | Gln | Val | |
| | 2210 | | | | | 2215 | | | | | 2220 | | | | |
| aat | aat | cca | aaa | gag | tgg | ctg | caa | gtg | gac | ttc | cag | aag | aca | atg | 6880 |
| Asn | Asn | Pro | Lys | Glu | Trp | Leu | Gln | Val | Asp | Phe | Gln | Lys | Thr | Met | |
| | 2225 | | | | | 2230 | | | | | 2235 | | | | |
| aaa | gtc | aca | gga | gta | act | act | cag | gga | gta | aaa | tct | ctg | ctt | acc | 6925 |
| Lys | Val | Thr | Gly | Val | Thr | Thr | Gln | Gly | Val | Lys | Ser | Leu | Leu | Thr | |
| | 2240 | | | | | 2245 | | | | | 2250 | | | | |
| agc | atg | tat | gtg | aag | gag | ttc | ctc | atc | tcc | agc | agt | caa | gat | ggc | 6970 |
| Ser | Met | Tyr | Val | Lys | Glu | Phe | Leu | Ile | Ser | Ser | Ser | Gln | Asp | Gly | |
| | 2255 | | | | | 2260 | | | | | 2265 | | | | |
| cat | cag | tgg | act | ctc | ttt | ttt | cag | aat | ggc | aaa | gta | aag | gtt | ttt | 7015 |
| His | Gln | Trp | Thr | Leu | Phe | Phe | Gln | Asn | Gly | Lys | Val | Lys | Val | Phe | |
| | 2270 | | | | | 2275 | | | | | 2280 | | | | |
| cag | gga | aat | caa | gac | tcc | ttc | aca | cct | gtg | gtg | aac | tct | cta | gac | 7060 |
| Gln | Gly | Asn | Gln | Asp | Ser | Phe | Thr | Pro | Val | Val | Asn | Ser | Leu | Asp | |
| | 2285 | | | | | 2290 | | | | | 2295 | | | | |
| cca | ccg | tta | ctg | act | cgc | tac | ctt | cga | att | cac | ccc | cag | agt | tgg | 7105 |
| Pro | Pro | Leu | Leu | Thr | Arg | Tyr | Leu | Arg | Ile | His | Pro | Gln | Ser | Trp | |
| | 2300 | | | | | 2305 | | | | | 2310 | | | | |
| gtg | cac | cag | att | gcc | ctg | agg | atg | gag | gtt | ctg | ggc | tgc | gag | gca | 7150 |
| Val | His | Gln | Ile | Ala | Leu | Arg | Met | Glu | Val | Leu | Gly | Cys | Glu | Ala | |
| | 2315 | | | | | 2320 | | | | | 2325 | | | | |
| cag | gac | ctc | tac | tgagggtggc | | cactgcagca | | cctgccactg | | ccgtcacctc | | | | | 7202 |
| Gln | Asp | Leu | Tyr | | | | | | | | | | | | |
| | 2330 | | | | | | | | | | | | | | |

| | | |
|---|---|---|
| tccctcctca gctccagggc agtgtccctc cctggcttgc cttctacctt tgtgctaaat | | 7262 |
| cctagcagac actgccttga agcctcctga attaactatc atcagtcctg catttctttg | | 7322 |
| gtgggggggcc aggagggtgc atccaattta acttaactct tacctatttt ctgcagctgc | | 7382 |
| tcccagatta ctccttcctt ccaatataac taggcaaaaa gaagtgagga gaaacctgca | | 7442 |
| tgaaagcatt cttccctgaa aagttaggcc tctcagagtc accacttcct ctgttgtaga | | 7502 |
| aaaactatgt gatgaaactt tgaaaaagat atttatgatg ttaacatttc aggttaagcc | | 7562 |
| tcatacgttt aaaataaaac tctcagttgt ttattatcct gatcaagcat ggaacaaagc | | 7622 |
| atgtttcagg atcagatcaa tacaatcttg gagtcaaaag gcaaatcatt tggacaatct | | 7682 |
| gcaaaatgga gagaatacaa taactactac agtaaagtct gtttctgctt ccttacacat | | 7742 |
| agatataatt atgttatttt gtcattatga ggggcacatt cttatctcca aaactagcat | | 7802 |
| tcttaaactg agaattatag atggggttca agaatcccta agtcccctga aattatataa | | 7862 |
| ggcattctgt ataaatgcaa atgtgcattt ttctgacgag tgtccataga tataaagcca | | 7922 |
| tttggtctta attctgacca ataaaaaaat aagtcaggag gatgcaattg ttgaaagctt | | 7982 |
| tgaaataaaa taacaatgtc ttcttgaaat ttgtgatggc caagaaagaa aatgatgatg | | 8042 |
| acattaggct tctaaaggac atacatttaa tatttctgtg gaaatatgag gaaaatccat | | 8102 |
| ggttatctga gataggagat acaaactttg taattctaat aatgcactca gtttactctc | | 8162 |
| tccctctact aatttcctgc tgaaaataac acaacaaaaa tgtaacaggg gaaattatat | | 8222 |
| accgtgactg aaaactagag tcctacttac atagttgaaa tatcaaggag gtcagaagaa | | 8282 |
| aattggactg gtgaaaacag aaaaaacact ccagtctgcc atatcaccac acaataggat | | 8342 |

```
ccccctcctt gccctccacc cccataagat tgtgaagggt ttactgctcc ttccatctgc      8402 ctgaccccttt cactatgact acacagaatc tcctgatagt aaaggggggct ggaggcaagg     8462 ataagttata gagcagttgg aggaagcatc caaagattgc aacccagggc aaatggaaaa      8522
caggagatcc taatatgaaa gaaaaatgga tcccaatctg agaaaaggca aagaatggc       8582 tacttttttc tatgctggag tattttctaa taatcctgct tgacccttat ctgacctctt      8642
tggaaactat aacatagctg tcacagtata gtcacaatcc acaaatgatg caggtgcaaa     8702
tggtttatag ccctgtgaag ttcttaaagt ttagaggcta acttacagaa atgaataagt     8762
tgttttgttt tatagcccgg tagaggagtt aaccccaaag gtgatatggt tttatttcct    8822
gttatgttta acttgataat cttattttgg cattcttttc ccattgacta tatacatctc    8882
tatttctcaa atgttcatgg aactagctct tttattttcc tgctggtttc ttcagtaatg    8942
agttaaataa aacattgaca catac                                           8967
```

<210> SEQ ID NO 2
<211> LENGTH: 2351
<212> TYPE: PRT
<213> ORGANISM: Homo sapiens

<400> SEQUENCE: 2

```
Met Gln Ile Glu Leu Ser Thr Cys Phe Phe Leu Cys Leu Leu Arg Phe
            -15                 -10                  -5

Cys Phe Ser Ala Thr Arg Arg Tyr Tyr Leu Gly Ala Val Glu Leu Ser
     -1   1               5                  10

Trp Asp Tyr Met Gln Ser Asp Leu Gly Glu Leu Pro Val Asp Ala Arg
     15                  20                  25

Phe Pro Pro Arg Val Pro Lys Ser Phe Pro Phe Asn Thr Ser Val Val
 30                  35                  40                  45

Tyr Lys Lys Thr Leu Phe Val Glu Phe Thr Asp His Leu Phe Asn Ile
                 50                  55                  60

Ala Lys Pro Arg Pro Pro Trp Met Gly Leu Leu Gly Pro Thr Ile Gln
             65                  70                  75

Ala Glu Val Tyr Asp Thr Val Val Ile Thr Leu Lys Asn Met Ala Ser
             80                  85                  90

His Pro Val Ser Leu His Ala Val Gly Val Ser Tyr Trp Lys Ala Ser
         95                 100                 105

Glu Gly Ala Glu Tyr Asp Asp Gln Thr Ser Gln Arg Glu Lys Glu Asp
110                 115                 120                 125

Asp Lys Val Phe Pro Gly Gly Ser His Thr Tyr Val Trp Gln Val Leu
                130                 135                 140

Lys Glu Asn Gly Pro Met Ala Ser Asp Pro Leu Cys Leu Thr Tyr Ser
             145                 150                 155

Tyr Leu Ser His Val Asp Leu Val Lys Asp Leu Asn Ser Gly Leu Ile
             160                 165                 170

Gly Ala Leu Leu Val Cys Arg Glu Gly Ser Leu Ala Lys Glu Lys Thr
         175                 180                 185

Gln Thr Leu His Lys Phe Ile Leu Leu Phe Ala Val Phe Asp Glu Gly
190                 195                 200                 205

Lys Ser Trp His Ser Glu Thr Lys Asn Ser Leu Met Gln Asp Arg Asp
                210                 215                 220

Ala Ala Ser Ala Arg Ala Trp Pro Lys Met His Thr Val Asn Gly Tyr
             225                 230                 235
```

-continued

```
Val Asn Arg Ser Leu Pro Gly Leu Ile Gly Cys His Arg Lys Ser Val
        240                 245                 250

Tyr Trp His Val Ile Gly Met Gly Thr Thr Pro Glu Val His Ser Ile
        255                 260                 265

Phe Leu Glu Gly His Thr Phe Leu Val Arg Asn His Arg Gln Ala Ser
270                 275                 280                 285

Leu Glu Ile Ser Pro Ile Thr Phe Leu Thr Ala Gln Thr Leu Leu Met
                290                 295                 300

Asp Leu Gly Gln Phe Leu Leu Phe Cys His Ile Ser Ser His Gln His
                305                 310                 315

Asp Gly Met Glu Ala Tyr Val Lys Val Asp Ser Cys Pro Glu Glu Pro
        320                 325                 330

Gln Leu Arg Met Lys Asn Asn Glu Glu Ala Glu Asp Tyr Asp Asp Asp
        335                 340                 345

Leu Thr Asp Ser Glu Met Asp Val Val Arg Phe Asp Asp Asn Ser
350                 355                 360                 365

Pro Ser Phe Ile Gln Ile Arg Ser Val Ala Lys Lys His Pro Lys Thr
                370                 375                 380

Trp Val His Tyr Ile Ala Ala Glu Glu Asp Trp Asp Tyr Ala Pro
        385                 390                 395

Leu Val Leu Ala Pro Asp Asp Arg Ser Tyr Lys Ser Gln Tyr Leu Asn
        400                 405                 410

Asn Gly Pro Gln Arg Ile Gly Arg Lys Tyr Lys Lys Val Arg Phe Met
        415                 420                 425

Ala Tyr Thr Asp Glu Thr Phe Lys Thr Arg Glu Ala Ile Gln His Glu
430                 435                 440                 445

Ser Gly Ile Leu Gly Pro Leu Leu Tyr Gly Glu Val Gly Asp Thr Leu
                450                 455                 460

Leu Ile Ile Phe Lys Asn Gln Ala Ser Arg Pro Tyr Asn Ile Tyr Pro
                465                 470                 475

His Gly Ile Thr Asp Val Arg Pro Leu Tyr Ser Arg Arg Leu Pro Lys
                480                 485                 490

Gly Val Lys His Leu Lys Asp Phe Pro Ile Leu Pro Gly Glu Ile Phe
        495                 500                 505

Lys Tyr Lys Trp Thr Val Thr Val Glu Asp Gly Pro Thr Lys Ser Asp
510                 515                 520                 525

Pro Arg Cys Leu Thr Arg Tyr Tyr Ser Ser Phe Val Asn Met Glu Arg
                530                 535                 540

Asp Leu Ala Ser Gly Leu Ile Gly Pro Leu Leu Ile Cys Tyr Lys Glu
                545                 550                 555

Ser Val Asp Gln Arg Gly Asn Gln Ile Met Ser Asp Lys Arg Asn Val
        560                 565                 570

Ile Leu Phe Ser Val Phe Asp Glu Asn Arg Ser Trp Tyr Leu Thr Glu
575                 580                 585

Asn Ile Gln Arg Phe Leu Pro Asn Pro Ala Gly Val Gln Leu Glu Asp
590                 595                 600                 605

Pro Glu Phe Gln Ala Ser Asn Ile Met His Ser Ile Asn Gly Tyr Val
                610                 615                 620

Phe Asp Ser Leu Gln Leu Ser Val Cys Leu His Glu Val Ala Tyr Trp
                625                 630                 635

Tyr Ile Leu Ser Ile Gly Ala Gln Thr Asp Phe Leu Ser Val Phe Phe
        640                 645                 650

Ser Gly Tyr Thr Phe Lys His Lys Met Val Tyr Glu Asp Thr Leu Thr
```

-continued

```
                655                 660                 665
Leu Phe Pro Phe Ser Gly Glu Thr Val Phe Met Ser Met Glu Asn Pro
670                 675                 680                 685

Gly Leu Trp Ile Leu Gly Cys His Asn Ser Asp Phe Arg Asn Arg Gly
                690                 695                 700

Met Thr Ala Leu Leu Lys Val Ser Ser Cys Asp Lys Asn Thr Gly Asp
                705                 710                 715

Tyr Tyr Glu Asp Ser Tyr Glu Asp Ile Ser Ala Tyr Leu Leu Ser Lys
                720                 725                 730

Asn Asn Ala Ile Glu Pro Arg Ser Phe Ser Gln Asn Ser Arg His Arg
735                 740                 745

Ser Thr Arg Gln Lys Gln Phe Asn Ala Thr Thr Ile Pro Glu Asn Asp
750                 755                 760                 765

Ile Glu Lys Thr Asp Pro Trp Phe Ala His Arg Thr Pro Met Pro Lys
                770                 775                 780

Ile Gln Asn Val Ser Ser Asp Leu Met Leu Leu Arg Gln Ser
                785                 790                 795

Pro Thr Pro His Gly Leu Ser Leu Ser Asp Leu Gln Glu Ala Lys Tyr
                800                 805                 810

Glu Thr Phe Ser Asp Asp Pro Ser Pro Gly Ala Ile Asp Ser Asn Asn
815                 820                 825

Ser Leu Ser Glu Met Thr His Phe Arg Pro Gln Leu His His Ser Gly
830                 835                 840                 845

Asp Met Val Phe Thr Pro Glu Ser Gly Leu Gln Leu Arg Leu Asn Glu
                850                 855                 860

Lys Leu Gly Thr Thr Ala Ala Thr Glu Leu Lys Lys Leu Asp Phe Lys
                865                 870                 875

Val Ser Ser Thr Ser Asn Asn Leu Ile Ser Thr Ile Pro Ser Asp Asn
                880                 885                 890

Leu Ala Ala Gly Thr Asp Asn Thr Ser Ser Leu Gly Pro Pro Ser Met
895                 900                 905

Pro Val His Tyr Asp Ser Gln Leu Asp Thr Thr Leu Phe Gly Lys Lys
910                 915                 920                 925

Ser Ser Pro Leu Thr Glu Ser Gly Gly Pro Leu Ser Leu Ser Glu Glu
                930                 935                 940

Asn Asn Asp Ser Lys Leu Leu Glu Ser Gly Leu Met Asn Ser Gln Glu
                945                 950                 955

Ser Ser Trp Gly Lys Asn Val Ser Ser Thr Glu Ser Gly Arg Leu Phe
                960                 965                 970

Lys Gly Lys Arg Ala His Gly Pro Ala Leu Leu Thr Lys Asp Asn Ala
975                 980                 985

Leu Phe Lys Val Ser Ile Ser Leu Leu Lys Thr Asn Lys Thr Ser Asn
990                 995                 1000                1005

Asn Ser Ala Thr Asn Arg Lys Thr His Ile Asp Gly Pro Ser Leu
                1010                1015                1020

Leu Ile Glu Asn Ser Pro Ser Val Trp Gln Asn Ile Leu Glu Ser
                1025                1030                1035

Asp Thr Glu Phe Lys Lys Val Thr Pro Leu Ile His Asp Arg Met
                1040                1045                1050

Leu Met Asp Lys Asn Ala Thr Ala Leu Arg Leu Asn His Met Ser
                1055                1060                1065

Asn Lys Thr Thr Ser Ser Lys Asn Met Glu Met Val Gln Gln Lys
                1070                1075                1080
```

-continued

```
Lys Glu Gly Pro Ile Pro Pro Asp Ala Gln Asn Pro Asp Met Ser
            1085                1090                1095
Phe Phe Lys Met Leu Phe Leu Pro Glu Ser Ala Arg Trp Ile Gln
            1100                1105                1110
Arg Thr His Gly Lys Asn Ser Leu Asn Ser Gly Gln Gly Pro Ser
            1115                1120                1125
Pro Lys Gln Leu Val Ser Leu Gly Pro Glu Lys Ser Val Glu Gly
            1130                1135                1140
Gln Asn Phe Leu Ser Glu Lys Asn Lys Val Val Gly Lys Gly
            1145                1150                1155
Glu Phe Thr Lys Asp Val Gly Leu Lys Glu Met Val Phe Pro Ser
            1160                1165                1170
Ser Arg Asn Leu Phe Leu Thr Asn Leu Asp Asn Leu His Glu Asn
            1175                1180                1185
Asn Thr His Asn Gln Glu Lys Lys Ile Gln Glu Glu Ile Glu Lys
            1190                1195                1200
Lys Glu Thr Leu Ile Gln Glu Asn Val Val Leu Pro Gln Ile His
            1205                1210                1215
Thr Val Thr Gly Thr Lys Asn Phe Met Lys Asn Leu Phe Leu Leu
            1220                1225                1230
Ser Thr Arg Gln Asn Val Glu Gly Ser Tyr Asp Gly Ala Tyr Ala
            1235                1240                1245
Pro Val Leu Gln Asp Phe Arg Ser Leu Asn Asp Ser Thr Asn Arg
            1250                1255                1260
Thr Lys Lys His Thr Ala His Phe Ser Lys Lys Gly Glu Glu Glu
            1265                1270                1275
Asn Leu Glu Gly Leu Gly Asn Gln Thr Lys Gln Ile Val Glu Lys
            1280                1285                1290
Tyr Ala Cys Thr Thr Arg Ile Ser Pro Asn Thr Ser Gln Gln Asn
            1295                1300                1305
Phe Val Thr Gln Arg Ser Lys Arg Ala Leu Lys Gln Phe Arg Leu
            1310                1315                1320
Pro Leu Glu Glu Thr Glu Leu Glu Lys Arg Ile Ile Val Asp Asp
            1325                1330                1335
Thr Ser Thr Gln Trp Ser Lys Asn Met Lys His Leu Thr Pro Ser
            1340                1345                1350
Thr Leu Thr Gln Ile Asp Tyr Asn Glu Lys Glu Lys Gly Ala Ile
            1355                1360                1365
Thr Gln Ser Pro Leu Ser Asp Cys Leu Thr Arg Ser His Ser Ile
            1370                1375                1380
Pro Gln Ala Asn Arg Ser Pro Leu Pro Ile Ala Lys Val Ser Ser
            1385                1390                1395
Phe Pro Ser Ile Arg Pro Ile Tyr Leu Thr Arg Val Leu Phe Gln
            1400                1405                1410
Asp Asn Ser Ser His Leu Pro Ala Ala Ser Tyr Arg Lys Lys Asp
            1415                1420                1425
Ser Gly Val Gln Glu Ser Ser His Phe Leu Gln Gly Ala Lys Lys
            1430                1435                1440
Asn Asn Leu Ser Leu Ala Ile Leu Thr Leu Glu Met Thr Gly Asp
            1445                1450                1455
Gln Arg Glu Val Gly Ser Leu Gly Thr Ser Ala Thr Asn Ser Val
            1460                1465                1470
```

-continued

```
Thr Tyr Lys Lys Val  Glu Asn Thr Val Leu  Pro Lys Pro Asp Leu
            1475                 1480                 1485

Pro Lys Thr Ser Gly  Lys Val Glu Leu Leu  Pro Lys Val His Ile
            1490                 1495                 1500

Tyr Gln Lys Asp Leu  Phe Pro Thr Glu Thr  Ser Asn Gly Ser Pro
            1505                 1510                 1515

Gly His Leu Asp Leu  Val Glu Gly Ser Leu  Leu Gln Gly Thr Glu
            1520                 1525                 1530

Gly Ala Ile Lys Trp  Asn Glu Ala Asn Arg  Pro Gly Lys Val Pro
            1535                 1540                 1545

Phe Leu Arg Val Ala  Thr Glu Ser Ser Ala  Lys Thr Pro Ser Lys
            1550                 1555                 1560

Leu Leu Asp Pro Leu  Ala Trp Asp Asn His  Tyr Gly Thr Gln Ile
            1565                 1570                 1575

Pro Lys Glu Glu Trp  Lys Ser Gln Glu Lys  Ser Pro Glu Lys Thr
            1580                 1585                 1590

Ala Phe Lys Lys Lys  Asp Thr Ile Leu Ser  Leu Asn Ala Cys Glu
            1595                 1600                 1605

Ser Asn His Ala Ile  Ala Ala Ile Asn Glu  Gly Gln Asn Lys Pro
            1610                 1615                 1620

Glu Ile Glu Val Thr  Trp Ala Lys Gln Gly  Arg Thr Glu Arg Leu
            1625                 1630                 1635

Cys Ser Gln Asn Pro  Pro Val Leu Lys Arg  His Gln Arg Glu Ile
            1640                 1645                 1650

Thr Arg Thr Thr Leu  Gln Ser Asp Gln Glu  Glu Ile Asp Tyr Asp
            1655                 1660                 1665

Asp Thr Ile Ser Val  Glu Met Lys Lys Glu  Asp Phe Asp Ile Tyr
            1670                 1675                 1680

Asp Glu Asp Glu Asn  Gln Ser Pro Arg Ser  Phe Gln Lys Lys Thr
            1685                 1690                 1695

Arg His Tyr Phe Ile  Ala Ala Val Glu Arg  Leu Trp Asp Tyr Gly
            1700                 1705                 1710

Met Ser Ser Ser Pro  His Val Leu Arg Asn  Arg Ala Gln Ser Gly
            1715                 1720                 1725

Ser Val Pro Gln Phe  Lys Lys Val Val Phe  Gln Glu Phe Thr Asp
            1730                 1735                 1740

Gly Ser Phe Thr Gln  Pro Leu Tyr Arg Gly  Glu Leu Asn Glu His
            1745                 1750                 1755

Leu Gly Leu Leu Gly  Pro Tyr Ile Arg Ala  Glu Val Glu Asp Asn
            1760                 1765                 1770

Ile Met Val Thr Phe  Arg Asn Gln Ala Ser  Arg Pro Tyr Ser Phe
            1775                 1780                 1785

Tyr Ser Ser Leu Ile  Ser Tyr Glu Glu Asp  Gln Arg Gln Gly Ala
            1790                 1795                 1800

Glu Pro Arg Lys Asn  Phe Val Lys Pro Asn  Glu Thr Lys Thr Tyr
            1805                 1810                 1815

Phe Trp Lys Val Gln  His His Met Ala Pro  Thr Lys Asp Glu Phe
            1820                 1825                 1830

Asp Cys Lys Ala Trp  Ala Tyr Phe Ser Asp  Val Asp Leu Glu Lys
            1835                 1840                 1845

Asp Val His Ser Gly  Leu Ile Gly Pro Leu  Leu Val Cys His Thr
            1850                 1855                 1860

Asn Thr Leu Asn Pro  Ala His Gly Arg Gln  Val Thr Val Gln Glu
```

-continued

```
                1865                1870                1875
Phe Ala Leu Phe  Phe Thr Ile Phe  Asp Glu Thr Lys  Ser Trp Tyr
        1880                1885                1890
Phe Thr Glu Asn  Met Glu Arg Asn  Cys Arg Ala Pro  Cys Asn Ile
        1895                1900                1905
Gln Met Glu Asp  Pro Thr Phe Lys  Glu Asn Tyr Arg  Phe His Ala
        1910                1915                1920
Ile Asn Gly Tyr  Ile Met Asp Thr  Leu Pro Gly Leu  Val Met Ala
        1925                1930                1935
Gln Asp Gln Arg  Ile Arg Trp Tyr  Leu Leu Ser Met  Gly Ser Asn
        1940                1945                1950
Glu Asn Ile His  Ser Ile His Phe  Ser Gly His Val  Phe Thr Val
        1955                1960                1965
Arg Lys Lys Glu  Glu Tyr Lys Met  Ala Leu Tyr Asn  Leu Tyr Pro
        1970                1975                1980
Gly Val Phe Glu  Thr Val Glu Met  Leu Pro Ser Lys  Ala Gly Ile
        1985                1990                1995
Trp Arg Val Glu  Cys Leu Ile Gly  Glu His Leu His  Ala Gly Met
        2000                2005                2010
Ser Thr Leu Phe  Leu Val Tyr Ser  Asn Lys Cys Gln  Thr Pro Leu
        2015                2020                2025
Gly Met Ala Ser  Gly His Ile Arg  Asp Phe Gln Ile  Thr Ala Ser
        2030                2035                2040
Gly Gln Tyr Gly  Gln Trp Ala Pro  Lys Leu Ala Arg  Leu His Tyr
        2045                2050                2055
Ser Gly Ser Ile  Asn Ala Trp Ser  Thr Lys Glu Pro  Phe Ser Trp
        2060                2065                2070
Ile Lys Val Asp  Leu Leu Ala Pro  Met Ile Ile His  Gly Ile Lys
        2075                2080                2085
Thr Gln Gly Ala  Arg Gln Lys Phe  Ser Ser Leu Tyr  Ile Ser Gln
        2090                2095                2100
Phe Ile Ile Met  Tyr Ser Leu Asp  Gly Lys Lys Trp  Gln Thr Tyr
        2105                2110                2115
Arg Gly Asn Ser  Thr Gly Thr Leu  Met Val Phe Phe  Gly Asn Val
        2120                2125                2130
Asp Ser Ser Gly  Ile Lys His Asn  Ile Phe Asn Pro  Pro Ile Ile
        2135                2140                2145
Ala Arg Tyr Ile  Arg Leu His Pro  Thr His Tyr Ser  Ile Arg Ser
        2150                2155                2160
Thr Leu Arg Met  Glu Leu Met Gly  Cys Asp Leu Asn  Ser Cys Ser
        2165                2170                2175
Met Pro Leu Gly  Met Glu Ser Lys  Ala Ile Ser Asp  Ala Gln Ile
        2180                2185                2190
Thr Ala Ser Ser  Tyr Phe Thr Asn  Met Phe Ala Thr  Trp Ser Pro
        2195                2200                2205
Ser Lys Ala Arg  Leu His Leu Gln  Gly Arg Ser Asn  Ala Trp Arg
        2210                2215                2220
Pro Gln Val Asn  Asn Pro Lys Glu  Trp Leu Gln Val  Asp Phe Gln
        2225                2230                2235
Lys Thr Met Lys  Val Thr Gly Val  Thr Thr Gln Gly  Val Lys Ser
        2240                2245                2250
Leu Leu Thr Ser  Met Tyr Val Lys  Glu Phe Leu Ile  Ser Ser Ser
        2255                2260                2265
```

```
Gln Asp Gly His Gln  Trp Thr Leu Phe Phe  Gln Asn Gly Lys Val
            2270                 2275                 2280

Lys Val Phe Gln Gly  Asn Gln Asp Ser Phe  Thr Pro Val Val Asn
            2285                 2290                 2295

Ser Leu Asp Pro Pro  Leu Leu Thr Arg Tyr  Leu Arg Ile His Pro
            2300                 2305                 2310

Gln Ser Trp Val His  Gln Ile Ala Leu Arg  Met Glu Val Leu Gly
            2315                 2320                 2325

Cys Glu Ala Gln Asp  Leu Tyr
            2330

<210> SEQ ID NO 3
<211> LENGTH: 1493
<212> TYPE: DNA
<213> ORGANISM: Homo sapiens
<220> FEATURE:
<221> NAME/KEY: sig_peptide
<222> LOCATION: (14)..(115)
<220> FEATURE:
<221> NAME/KEY: CDS
<222> LOCATION: (14)..(1084)
<220> FEATURE:
<221> NAME/KEY: mat_peptide
<222> LOCATION: (116)..(1084)

<400> SEQUENCE: 3
tgagcggggg atg atg gcg ccg cgg agg gtc agg tcg ttt ctg cgc ggg          49
           Met Ala Pro Arg Arg Val Arg Ser Phe Leu Arg Gly
               -30                 -25 ctc ccg gcg ctg cta ctg ctg ctg ctc ttc ctc ggg ccc tgg ccc gct         97
Leu Pro Ala Leu Leu Leu Leu Leu Leu Phe Leu Gly Pro Trp Pro Ala
        -20                 -15                 -10 gcg agc cac ggc ggc aag tac tcg cgg gag aag aac cag ccc aag ccg        145
Ala Ser His Gly Gly Lys Tyr Ser Arg Glu Lys Asn Gln Pro Lys Pro
    -5               -1  1                5                  10 tcc ccg aaa cgc gag tcc gga gag gag ttc cgc atg gag aag ttg aac        193
Ser Pro Lys Arg Glu Ser Gly Glu Glu Phe Arg Met Glu Lys Leu Asn
                 15                  20                  25 cag ctg tgg gag aag gcc cag cga ctg cat ctt cct ccc gtg agg ctg        241
Gln Leu Trp Glu Lys Ala Gln Arg Leu His Leu Pro Pro Val Arg Leu
         30                  35                  40 gcc gag ctc cac gct gat ctg aag ata cag gag agg gac gaa ctc gcc        289
Ala Glu Leu His Ala Asp Leu Lys Ile Gln Glu Arg Asp Glu Leu Ala
             45                  50                  55 tgg aag aaa cta aag ctt gac ggc ttg gac gaa gat ggg gag aag gaa        337
Trp Lys Lys Leu Lys Leu Asp Gly Leu Asp Glu Asp Gly Glu Lys Glu
     60                  65                  70 gcg aga ctc ata cgc aac ctc aat gtc atc ttg gcc aag tat ggt ctg        385
Ala Arg Leu Ile Arg Asn Leu Asn Val Ile Leu Ala Lys Tyr Gly Leu
75                  80                  85                  90 gac gga aag aag gac gct cgg cag gtg acc agc aac tcc ctc agt ggc        433
Asp Gly Lys Lys Asp Ala Arg Gln Val Thr Ser Asn Ser Leu Ser Gly
                 95                 100                 105 acc cag gaa gac ggg ctg gat gac ccc agg ctg gaa aag ctg tgg cac        481
Thr Gln Glu Asp Gly Leu Asp Asp Pro Arg Leu Glu Lys Leu Trp His
            110                 115                 120 aag gcg aag acc tct ggg aaa ttc tcc ggc gaa gaa ctg gac aag ctc        529
Lys Ala Lys Thr Ser Gly Lys Phe Ser Gly Glu Glu Leu Asp Lys Leu
        125                 130                 135 tgg cgg gag ttc ctg cat cac aaa gag aaa gtt cac gag tac aac gtc        577
Trp Arg Glu Phe Leu His His Lys Glu Lys Val His Glu Tyr Asn Val
```

```
ctg ctg gag acc ctg agc agg acc gaa gaa atc cac gag aac gtc att    625
Leu Leu Glu Thr Leu Ser Arg Thr Glu Glu Ile His Glu Asn Val Ile
155                 160                 165                 170 agc ccc tcg gac ctg agc gac atc aag ggc agc gtc ctg cac agc agg    673
Ser Pro Ser Asp Leu Ser Asp Ile Lys Gly Ser Val Leu His Ser Arg
                175                 180                 185 cac acg gag ctg aag gag aag ctg cgc agc atc aac cag ggc ctg gac    721
His Thr Glu Leu Lys Glu Lys Leu Arg Ser Ile Asn Gln Gly Leu Asp
            190                 195                 200 cgc ctg cgc agg gtc agc cac cag ggc tac agc act gag gct gag ttc    769
Arg Leu Arg Arg Val Ser His Gln Gly Tyr Ser Thr Glu Ala Glu Phe
        205                 210                 215 gag gag ccc agg gtg att gac ctg tgg gac ctg gcg cag tcc gcc aac    817
Glu Glu Pro Arg Val Ile Asp Leu Trp Asp Leu Ala Gln Ser Ala Asn
220                 225                 230 ctc acg gac aag gag ctg gag gcg ttc cgg gag gag ctc aag cac ttc    865
Leu Thr Asp Lys Glu Leu Glu Ala Phe Arg Glu Glu Leu Lys His Phe
235                 240                 245                 250 gaa gcc aaa atc gag aag cac aac cac tac cag aag cag ctg gag att    913
Glu Ala Lys Ile Glu Lys His Asn His Tyr Gln Lys Gln Leu Glu Ile
                255                 260                 265 gcg cac gag aag ctg agg cac gca gag agc gtg ggc gac ggc gag cgt    961
Ala His Glu Lys Leu Arg His Ala Glu Ser Val Gly Asp Gly Glu Arg
            270                 275                 280 gtg agc cgc agc cgc gag aag cac gcc ctg ctg gag ggg cgg acc aag    1009
Val Ser Arg Ser Arg Glu Lys His Ala Leu Leu Glu Gly Arg Thr Lys
        285                 290                 295 gag ctg ggc tac acg gtg aag aag cat ctg cag gac ctg tcc ggc agg    1057
Glu Leu Gly Tyr Thr Val Lys Lys His Leu Gln Asp Leu Ser Gly Arg
300                 305                 310 atc tcc aga gct cgg cac aac gaa ctc tgaaggcact ggggagccca          1104
Ile Ser Arg Ala Arg His Asn Glu Leu
315                 320 gcccggcagg gaagaggcca gcgtgaagga cctgggctct tggccgtggc atttccgtgg  1164
acagcccgcc gtcagggtgg ctggggctgg cacgggtgtc gaggcaggaa ggattgtttc  1224
tggtgactgc agccgctgcc gtcgcgacac agggcttggt ggtggtagca tttgggtctg  1284
agatcggccc agctctgact gaaggggctt ggcttccact cagcatcagc gtggcagtca  1344 ccacccagt gaggacctcg atgtccagct gctgtcaggt ctgatagtcc tctgctaaaa   1404
caacacgatt tacataaaaa atcttacaca tctgccaccg gaaataccat gcacagagtc  1464
cttaaaaaat agagtgcagt atttaaacc                                    1493
```

<210> SEQ ID NO 4
<211> LENGTH: 357
<212> TYPE: PRT
<213> ORGANISM: Homo sapiens

<400> SEQUENCE: 4

```
Met Ala Pro Arg Arg Val Arg Ser Phe Leu Arg Gly Leu Pro Ala Leu
                -30                 -25                 -20

Leu Leu Leu Leu Leu Phe Leu Gly Pro Trp Pro Ala Ala Ser His Gly
            -15                 -10                 -5

Gly Lys Tyr Ser Arg Glu Lys Asn Gln Pro Lys Pro Ser Pro Lys Arg
        -1   1               5                   10

Glu Ser Gly Glu Glu Phe Arg Met Glu Lys Leu Asn Gln Leu Trp Glu
15                  20                  25                  30
```

```
Lys Ala Gln Arg Leu His Leu Pro Pro Val Arg Leu Ala Glu Leu His
                35                  40                  45

Ala Asp Leu Lys Ile Gln Glu Arg Asp Glu Leu Ala Trp Lys Lys Leu
            50                  55                  60

Lys Leu Asp Gly Leu Asp Glu Asp Gly Glu Lys Glu Ala Arg Leu Ile
        65                  70                  75

Arg Asn Leu Asn Val Ile Leu Ala Lys Tyr Gly Leu Asp Gly Lys Lys
    80                  85                  90

Asp Ala Arg Gln Val Thr Ser Asn Ser Leu Ser Gly Thr Gln Glu Asp
95                 100                 105                 110

Gly Leu Asp Asp Pro Arg Leu Glu Lys Leu Trp His Lys Ala Lys Thr
               115                 120                 125

Ser Gly Lys Phe Ser Gly Glu Glu Leu Asp Lys Leu Trp Arg Glu Phe
               130                 135                 140

Leu His His Lys Glu Lys Val His Glu Tyr Asn Val Leu Leu Glu Thr
           145                 150                 155

Leu Ser Arg Thr Glu Glu Ile His Glu Asn Val Ile Ser Pro Ser Asp
       160                 165                 170

Leu Ser Asp Ile Lys Gly Ser Val Leu His Ser Arg His Thr Glu Leu
175                 180                 185                 190

Lys Glu Lys Leu Arg Ser Ile Asn Gln Gly Leu Asp Arg Leu Arg Arg
               195                 200                 205

Val Ser His Gln Gly Tyr Ser Thr Glu Ala Glu Phe Glu Glu Pro Arg
           210                 215                 220

Val Ile Asp Leu Trp Asp Leu Ala Gln Ser Ala Asn Leu Thr Asp Lys
       225                 230                 235

Glu Leu Glu Ala Phe Arg Glu Glu Leu Lys His Phe Glu Ala Lys Ile
   240                 245                 250

Glu Lys His Asn His Tyr Gln Lys Gln Leu Glu Ile Ala His Glu Lys
255                 260                 265                 270

Leu Arg His Ala Glu Ser Val Gly Asp Gly Glu Arg Val Ser Arg Ser
               275                 280                 285

Arg Glu Lys His Ala Leu Leu Glu Gly Arg Thr Lys Glu Leu Gly Tyr
           290                 295                 300

Thr Val Lys Lys His Leu Gln Asp Leu Ser Gly Arg Ile Ser Arg Ala
       305                 310                 315

Arg His Asn Glu Leu
           320

<210> SEQ ID NO 5
<211> LENGTH: 1424
<212> TYPE: PRT
<213> ORGANISM: Homo sapiens

<400> SEQUENCE: 5

Ala Thr Arg Arg Tyr Tyr Leu Gly Ala Val Glu Leu Ser Trp Asp Tyr
1               5                  10                  15

Met Gln Ser Asp Leu Gly Glu Leu Pro Val Asp Ala Arg Phe Pro Pro
            20                  25                  30

Arg Val Pro Lys Ser Phe Pro Phe Asn Thr Ser Val Val Tyr Lys Lys
        35                  40                  45

Thr Leu Phe Val Glu Phe Thr Asp His Leu Phe Asn Ile Ala Lys Pro
    50                  55                  60

Arg Pro Pro Trp Met Gly Leu Leu Gly Pro Thr Ile Gln Ala Glu Val
```

```
                65                  70                  75                  80
Tyr Asp Thr Val Val Ile Thr Leu Lys Asn Met Ala Ser His Pro Val
                        85                  90                  95
Ser Leu His Ala Val Gly Val Ser Tyr Trp Lys Ala Ser Glu Gly Ala
                    100                 105                 110
Glu Tyr Asp Asp Gln Thr Ser Gln Arg Glu Lys Glu Asp Asp Lys Val
                115                 120                 125
Phe Pro Gly Gly Ser His Thr Tyr Val Trp Gln Val Leu Lys Glu Asn
            130                 135                 140
Gly Pro Met Ala Ser Asp Pro Leu Cys Leu Thr Tyr Ser Tyr Leu Ser
145                 150                 155                 160
His Val Asp Leu Val Lys Asp Leu Asn Ser Gly Leu Ile Gly Ala Leu
                        165                 170                 175
Leu Val Cys Arg Glu Gly Ser Leu Ala Lys Glu Lys Thr Gln Thr Leu
                    180                 185                 190
His Lys Phe Ile Leu Leu Phe Ala Val Phe Asp Glu Gly Lys Ser Trp
                195                 200                 205
His Ser Glu Thr Lys Asn Ser Leu Met Gln Asp Arg Asp Ala Ala Ser
            210                 215                 220
Ala Arg Ala Trp Pro Lys Met His Thr Val Asn Gly Tyr Val Asn Arg
225                 230                 235                 240
Ser Leu Pro Gly Leu Ile Gly Cys His Arg Lys Ser Val Tyr Trp His
                        245                 250                 255
Val Ile Gly Met Gly Thr Thr Pro Glu Val His Ser Ile Phe Leu Glu
                    260                 265                 270
Gly His Thr Phe Leu Val Arg Asn His Arg Gln Ala Ser Leu Glu Ile
                275                 280                 285
Ser Pro Ile Thr Phe Leu Thr Ala Gln Thr Leu Leu Met Asp Leu Gly
            290                 295                 300
Gln Phe Leu Leu Phe Cys His Ile Ser Ser His Gln His Asp Gly Met
305                 310                 315                 320
Glu Ala Tyr Val Lys Val Asp Ser Cys Pro Glu Glu Pro Gln Leu Arg
                        325                 330                 335
Met Lys Asn Asn Glu Glu Ala Glu Asp Tyr Asp Asp Asp Leu Thr Asp
                    340                 345                 350
Ser Glu Met Asp Val Val Arg Phe Asp Asp Asp Asn Ser Pro Ser Phe
                355                 360                 365
Ile Gln Ile Arg Ser Val Ala Lys Lys His Pro Lys Thr Trp Val His
            370                 375                 380
Tyr Ile Ala Ala Glu Glu Glu Asp Trp Asp Tyr Ala Pro Leu Val Leu
385                 390                 395                 400
Ala Pro Asp Asp Arg Ser Tyr Lys Ser Gln Tyr Leu Asn Asn Gly Pro
                        405                 410                 415
Gln Arg Ile Gly Arg Lys Tyr Lys Lys Val Arg Phe Met Ala Tyr Thr
                    420                 425                 430
Asp Glu Thr Phe Lys Thr Arg Glu Ala Ile Gln His Glu Ser Gly Ile
                435                 440                 445
Leu Gly Pro Leu Leu Tyr Gly Glu Val Gly Asp Thr Leu Leu Ile Ile
            450                 455                 460
Phe Lys Asn Gln Ala Ser Arg Pro Tyr Asn Ile Tyr Pro His Gly Ile
465                 470                 475                 480
Thr Asp Val Arg Pro Leu Tyr Ser Arg Arg Leu Pro Lys Gly Val Lys
                        485                 490                 495
```

```
His Leu Lys Asp Phe Pro Ile Leu Pro Gly Glu Ile Phe Lys Tyr Lys
            500                 505                 510

Trp Thr Val Thr Val Glu Asp Gly Pro Thr Lys Ser Asp Pro Arg Cys
            515                 520                 525

Leu Thr Arg Tyr Tyr Ser Ser Phe Val Asn Met Glu Arg Asp Leu Ala
            530                 535                 540

Ser Gly Leu Ile Gly Pro Leu Leu Ile Cys Tyr Lys Glu Ser Val Asp
545                 550                 555                 560

Gln Arg Gly Asn Gln Ile Met Ser Asp Lys Arg Asn Val Ile Leu Phe
                565                 570                 575

Ser Val Phe Asp Glu Asn Arg Ser Trp Tyr Leu Thr Glu Asn Ile Gln
            580                 585                 590

Arg Phe Leu Pro Asn Pro Ala Gly Val Gln Leu Glu Asp Pro Glu Phe
            595                 600                 605

Gln Ala Ser Asn Ile Met His Ser Ile Asn Gly Tyr Val Phe Asp Ser
            610                 615                 620

Leu Gln Leu Ser Val Cys Leu His Glu Val Ala Tyr Trp Tyr Ile Leu
625                 630                 635                 640

Ser Ile Gly Ala Gln Thr Asp Phe Leu Ser Val Phe Phe Ser Gly Tyr
                645                 650                 655

Thr Phe Lys His Lys Met Val Tyr Glu Asp Thr Leu Thr Leu Phe Pro
            660                 665                 670

Phe Ser Gly Glu Thr Val Phe Met Ser Met Glu Asn Pro Gly Leu Trp
            675                 680                 685

Ile Leu Gly Cys His Asn Ser Asp Phe Arg Asn Arg Gly Met Thr Ala
            690                 695                 700

Leu Leu Lys Val Ser Ser Cys Asp Lys Asn Thr Gly Asp Tyr Tyr Glu
705                 710                 715                 720

Asp Ser Tyr Glu Asp Ile Ser Ala Tyr Leu Leu Ser Lys Asn Asn Ala
                725                 730                 735

Ile Glu Pro Arg Glu Ile Thr Arg Thr Thr Leu Gln Ser Asp Gln Glu
            740                 745                 750

Glu Ile Asp Tyr Asp Asp Thr Ile Ser Val Glu Met Lys Lys Glu Asp
            755                 760                 765

Phe Asp Ile Tyr Asp Glu Asp Glu Asn Gln Ser Pro Arg Ser Phe Gln
            770                 775                 780

Lys Lys Thr Arg His Tyr Phe Ile Ala Ala Val Glu Arg Leu Trp Asp
785                 790                 795                 800

Tyr Gly Met Ser Ser Ser Pro His Val Leu Arg Asn Arg Ala Gln Ser
                805                 810                 815

Gly Ser Val Pro Gln Phe Lys Lys Val Val Phe Gln Glu Phe Thr Asp
            820                 825                 830

Gly Ser Phe Thr Gln Pro Leu Tyr Arg Gly Glu Leu Asn Glu His Leu
            835                 840                 845

Gly Leu Leu Gly Pro Tyr Ile Arg Ala Glu Val Glu Asp Asn Ile Met
850                 855                 860

Val Thr Phe Arg Asn Gln Ala Ser Arg Pro Tyr Ser Phe Tyr Ser Ser
865                 870                 875                 880

Leu Ile Ser Tyr Glu Glu Asp Gln Arg Gln Gly Ala Glu Pro Arg Lys
                885                 890                 895

Asn Phe Val Lys Pro Asn Glu Thr Lys Thr Tyr Phe Trp Lys Val Gln
            900                 905                 910
```

-continued

```
His His Met Ala Pro Thr Lys Asp Glu Phe Asp Cys Lys Ala Trp Ala
        915                 920                 925

Tyr Phe Ser Asp Val Asp Leu Glu Lys Asp Val His Ser Gly Leu Ile
        930                 935                 940

Gly Pro Leu Leu Val Cys His Thr Asn Thr Leu Asn Pro Ala His Gly
945                 950                 955                 960

Arg Gln Val Thr Val Gln Glu Phe Ala Leu Phe Phe Thr Ile Phe Asp
        965                 970                 975

Glu Thr Lys Ser Trp Tyr Phe Thr Glu Asn Met Glu Arg Asn Cys Arg
        980                 985                 990

Ala Pro Cys Asn Ile Gln Met Glu Asp Pro Thr Phe Lys Glu Asn Tyr
        995                 1000                1005

Arg Phe His Ala Ile Asn Gly Tyr Ile Met Asp Thr Leu Pro Gly
        1010                1015                1020

Leu Val Met Ala Gln Asp Gln Arg Ile Arg Trp Tyr Leu Leu Ser
        1025                1030                1035

Met Gly Ser Asn Glu Asn Ile His Ser Ile His Phe Ser Gly His
        1040                1045                1050

Val Phe Thr Val Arg Lys Lys Glu Glu Tyr Lys Met Ala Leu Tyr
        1055                1060                1065

Asn Leu Tyr Pro Gly Val Phe Glu Thr Val Glu Met Leu Pro Ser
        1070                1075                1080

Lys Ala Gly Ile Trp Arg Val Glu Cys Leu Ile Gly Glu His Leu
        1085                1090                1095

His Ala Gly Met Ser Thr Leu Phe Leu Val Tyr Ser Asn Lys Cys
        1100                1105                1110

Gln Thr Pro Leu Gly Met Ala Ser Gly His Ile Arg Asp Phe Gln
        1115                1120                1125

Ile Thr Ala Ser Gly Gln Tyr Gly Gln Trp Ala Pro Lys Leu Ala
        1130                1135                1140

Arg Leu His Tyr Ser Gly Ser Ile Asn Ala Trp Ser Thr Lys Glu
        1145                1150                1155

Pro Phe Ser Trp Ile Lys Val Asp Leu Leu Ala Pro Met Ile Ile
        1160                1165                1170

His Gly Ile Lys Thr Gln Gly Ala Arg Gln Lys Phe Ser Ser Leu
        1175                1180                1185

Tyr Ile Ser Gln Phe Ile Ile Met Tyr Ser Leu Asp Gly Lys Lys
        1190                1195                1200

Trp Gln Thr Tyr Arg Gly Asn Ser Thr Gly Thr Leu Met Val Phe
        1205                1210                1215

Phe Gly Asn Val Asp Ser Ser Gly Ile Lys His Asn Ile Phe Asn
        1220                1225                1230

Pro Pro Ile Ile Ala Arg Tyr Ile Arg Leu His Pro Thr His Tyr
        1235                1240                1245

Ser Ile Arg Ser Thr Leu Arg Met Glu Leu Met Gly Cys Asp Leu
        1250                1255                1260

Asn Ser Cys Ser Met Pro Leu Gly Met Glu Ser Lys Ala Ile Ser
        1265                1270                1275

Asp Ala Gln Ile Thr Ala Ser Ser Tyr Phe Thr Asn Met Phe Ala
        1280                1285                1290

Thr Trp Ser Pro Ser Lys Ala Arg Leu His Leu Gln Gly Arg Ser
        1295                1300                1305

Asn Ala Trp Arg Pro Gln Val Asn Asn Pro Lys Glu Trp Leu Gln
```

-continued

```
                1310                1315                1320
Val Asp Phe Gln Lys Thr Met Lys Val Thr Gly Val Thr Thr Gln
    1325                1330                1335

Gly Val Lys Ser Leu Leu Thr Ser Met Tyr Val Lys Glu Phe Leu
    1340                1345                1350

Ile Ser Ser Ser Gln Asp Gly His Gln Trp Thr Leu Phe Phe Gln
    1355                1360                1365

Asn Gly Lys Val Lys Val Phe Gln Gly Asn Gln Asp Ser Phe Thr
    1370                1375                1380

Pro Val Val Asn Ser Leu Asp Pro Pro Leu Leu Thr Arg Tyr Leu
    1385                1390                1395

Arg Ile His Pro Gln Ser Trp Val His Gln Ile Ala Leu Arg Met
    1400                1405                1410

Glu Val Leu Gly Cys Glu Ala Gln Asp Leu Tyr
    1415                1420

<210> SEQ ID NO 6
<211> LENGTH: 41
<212> TYPE: DNA
<213> ORGANISM: Homo sapiens

<400> SEQUENCE: 6
aacgaagtcc ggagccaaga agcatcctaa aacttgggta c                    41

<210> SEQ ID NO 7
<211> LENGTH: 47
<212> TYPE: DNA
<213> ORGANISM: Homo sapiens

<400> SEQUENCE: 7
acgcatcaag cttctatctt ggttcaatgg cattgttttt actcagc              47

<210> SEQ ID NO 8
<211> LENGTH: 26
<212> TYPE: DNA
<213> ORGANISM: Homo sapiens

<400> SEQUENCE: 8
catgggcgcc tccatcgagg gtcggt                                     26

<210> SEQ ID NO 9
<211> LENGTH: 26
<212> TYPE: DNA
<213> ORGANISM: Homo sapiens

<400> SEQUENCE: 9
ccggaccgac cctcgatgga ggcgcc                                     26
```